United States Patent [19]

Kibblewhite et al.

[11] Patent Number: 5,216,622
[45] Date of Patent: Jun. 1, 1993

[54] ULTRASONIC DRIVE/SENSE CIRCUITRY FOR AUTOMATED FASTENER TIGHTENING

[75] Inventors: Ian E. Kibblewhite, Frazer, Pa.; Denis Downey, San Diego, Calif.; John Drummond, Dublin; John F. Butler, Naas, both of Ireland

[73] Assignee: SPS Technologies, Inc., Newtown, Pa.

[21] Appl. No.: 575,469

[22] Filed: Aug. 30, 1990

Related U.S. Application Data

[63] Continuation-in-part of Ser. No. 516,027, Apr. 27, 1990, abandoned.

[51] Int. Cl.$^5$ .................. G01N 29/00; G04F 10/00
[52] U.S. Cl. .................... 364/508; 364/569; 73/761
[58] Field of Search ............... 364/506, 507, 508, 569, 364/474.02, 474.34; 73/760, 761, 581

[56] References Cited

U.S. PATENT DOCUMENTS

| | | | |
|---|---|---|---|
| 4,014,208 | 3/1977 | Moore | 73/67.9 |
| 4,210,904 | 7/1980 | Renzel et al. | 364/507 X |
| 4,295,377 | 10/1981 | Couchman | 73/761 |
| 4,363,242 | 12/1982 | Heyman | 73/761 |
| 4,413,518 | 11/1983 | Jones | 73/615 |
| 4,471,657 | 9/1984 | Voris et al. | 73/761 |
| 4,598,375 | 7/1986 | Hiramatsu et al. | 364/569 |
| 4,602,511 | 7/1986 | Holt | 73/581 |
| 4,755,953 | 7/1988 | Geithman et al. | 364/507 |
| 4,760,740 | 8/1988 | Meisterling | 73/761 |
| 4,846,001 | 7/1989 | Kibblewhite | 73/761 |
| 4,899,591 | 2/1990 | Kibblewhite | 73/761 |
| 5,016,200 | 5/1991 | Passarelli | 364/567 |
| 5,018,988 | 5/1991 | Kibblewhite et al. | 73/761 X |

OTHER PUBLICATIONS

NASA CR-61354, "Fastener Load Analysis Method," Fred R. Rollins, Jr. Apr. 2, 1971.

Primary Examiner—Parshotam S. Lall
Assistant Examiner—Collin W. Park
Attorney, Agent, or Firm—John J. Simkanich

[57] ABSTRACT

An ultrasonic signal drive/sense circuitry is provided, which circuitry is adaptable to a variety of automated or manual fastener tightening operations. This circuitry operates for measuring tension in a fastener as a function of change in time of flight of an ultrasonic wave. A microcontroller directs the operation of circuit components to generate high amplitude, high repetition rate, drive pulses with these amplitude and repetition rate factors being electronically adjustable to compensate for fastening tool and fastener acoustical properties and tightening rates. Software driven timing circuitry calculates, calibrates and adjusts pulse echo detection window width and center location and also optimum echo detection threshold. This timing circuitry is implemented by digital techniques to measure pulse time of flight and incorporates analog interpolation of data between digital counts. Sampling rates of the echo pulses are adjusted to tool speed. An auto-calibration technique is implemented prior to each fastener tightening operation to overcome circuit errors and set detection window position and to optimize pulse voltage and echo threshold detection levels. Time of flight data is selectably calculable from the initial ultrasonic pulse to the primary echo or successive reflections thereof.

32 Claims, 30 Drawing Sheets

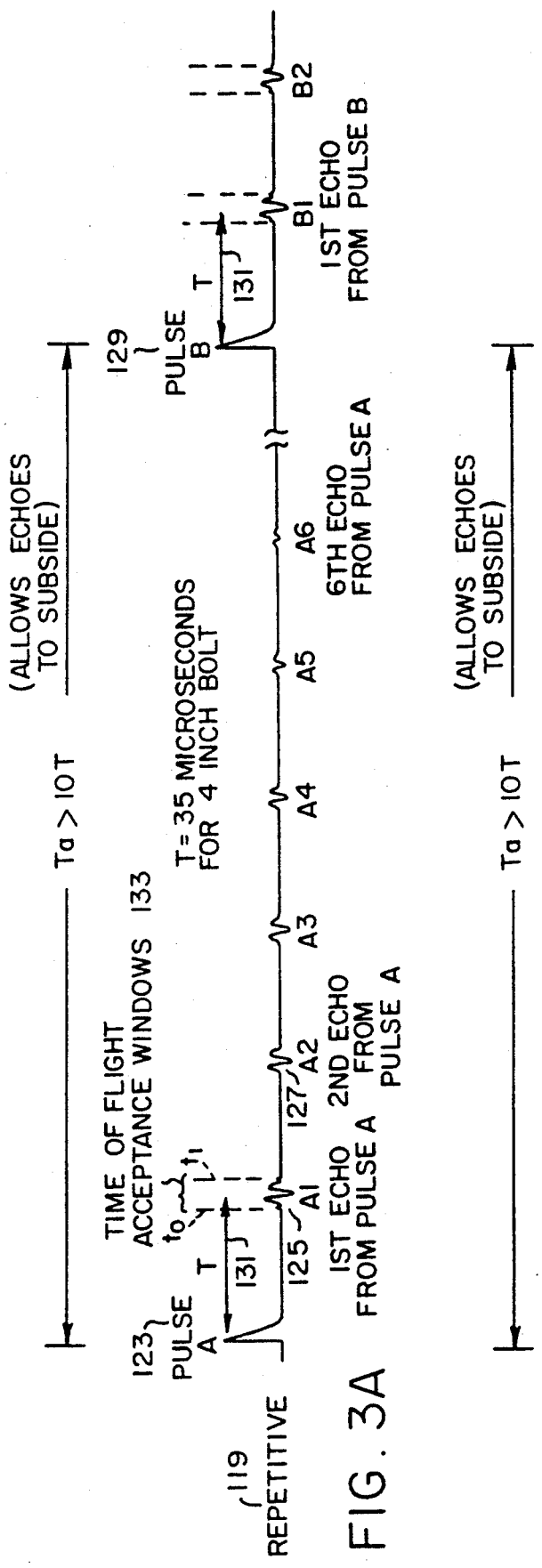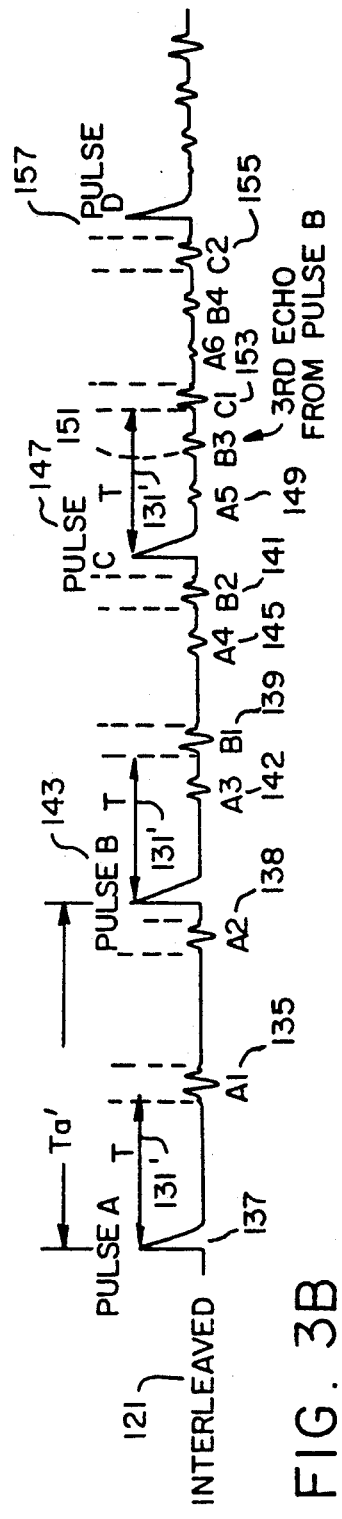

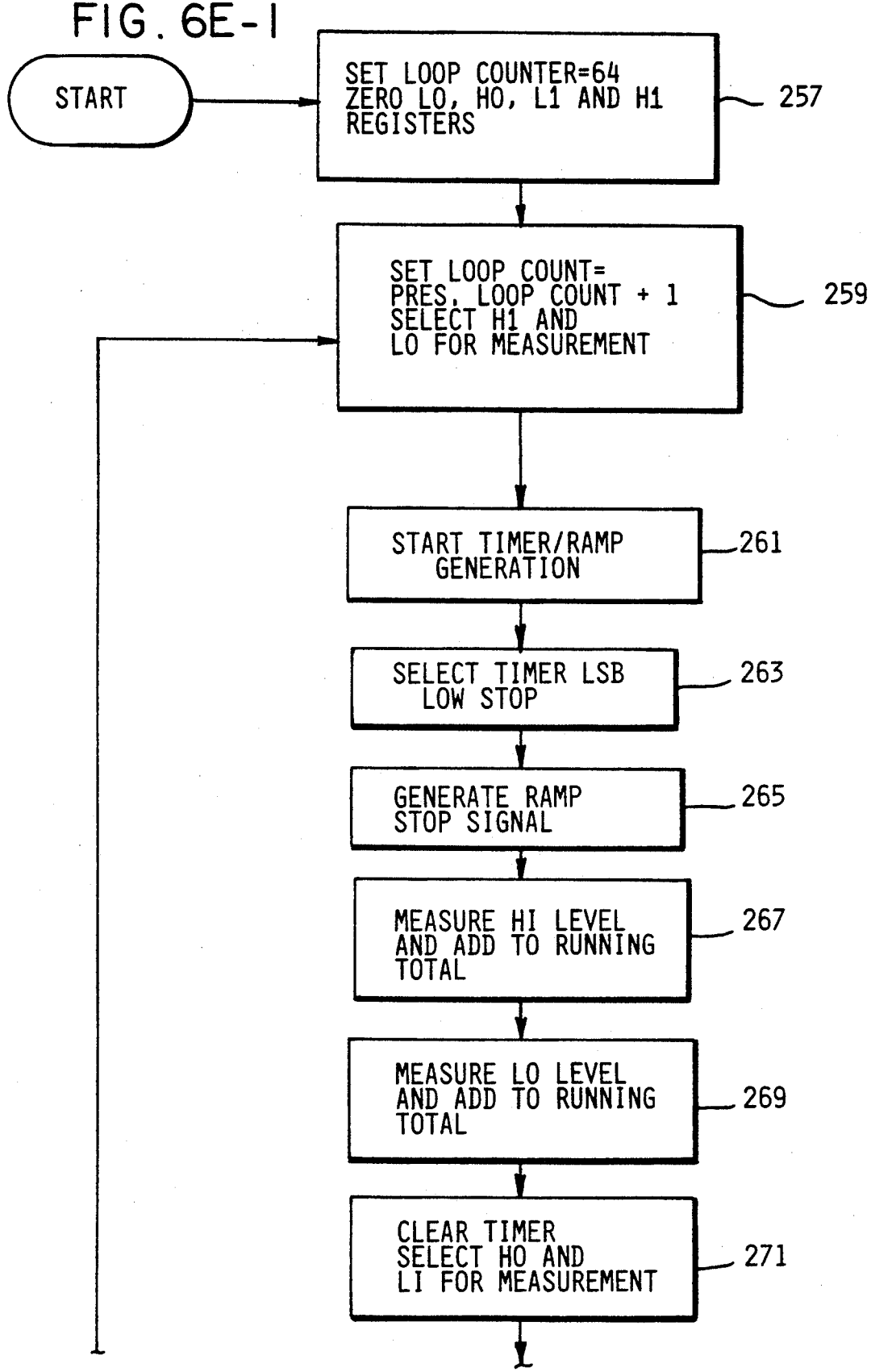

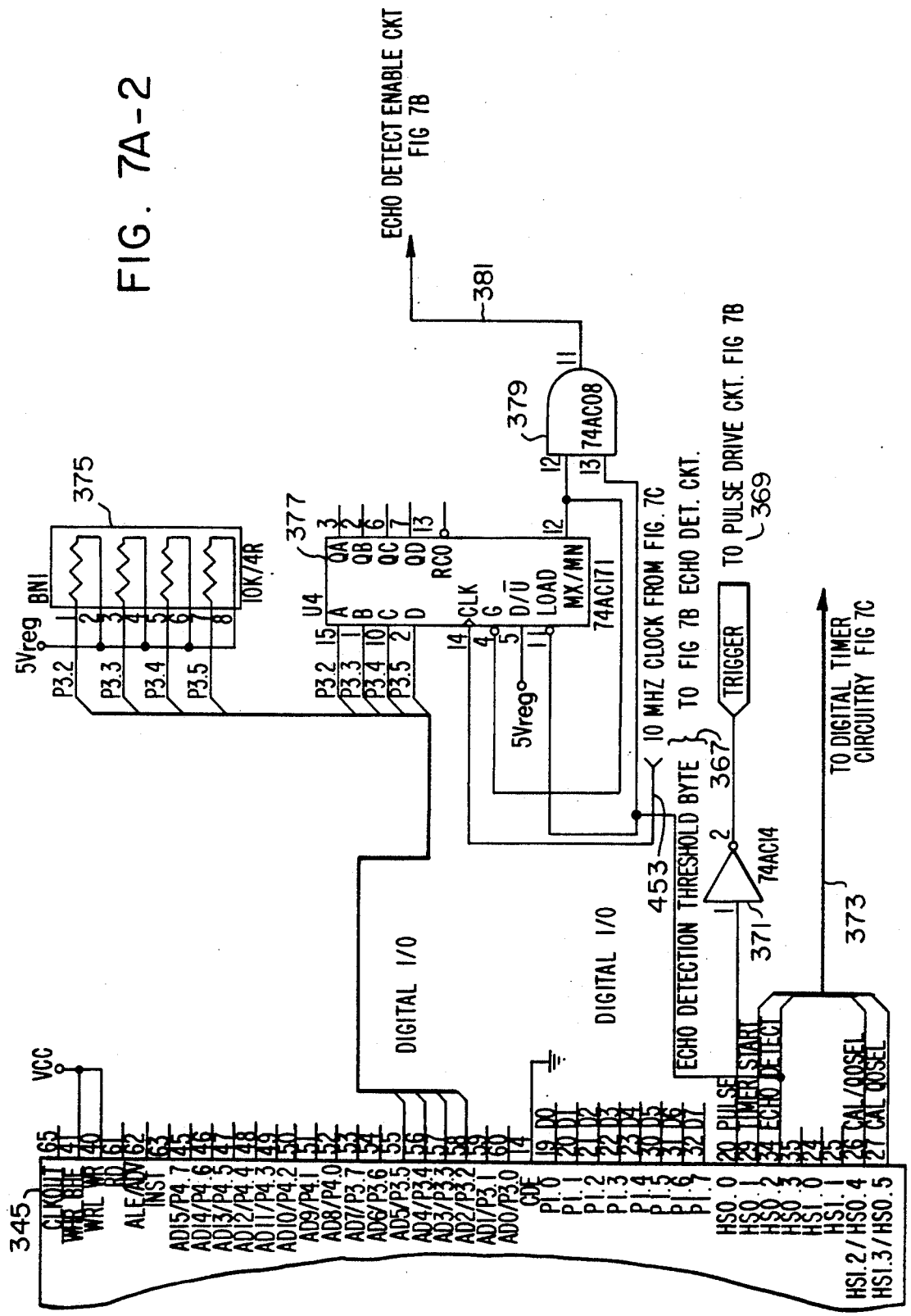

ULTRASONIC DRIVE/SENSE CIRCUITRY FOR AUTOMATED FASTENER TIGHTENING

This application is a continuation-in-part of application Ser. No. 516,027, filed Apr. 27, 1990, abandoned.

BACKGROUND OF THE INVENTION

This invention relates to electronic circuitry for generating ultrasonic signals and for sensing reflected ultrasonic echo signals; and more specifically to such electronic circuitry for use as ultrasonic tension control in manual or automated fastener tightening.

Ultrasonic signal processing has been used in the past to detect flaws in metal objects, such as fasteners, and to measure the elongation of a fastener during or after tightening. The procedure adopted has been to transmit electronically generated ultrasonic pulses down the length of a fastener and then to measure the time from pulse to echo, i.e. the reflected ultrasonic signal. This is the "time of flight" of the echo. The time of flight of the echo measures the distance to a fault, an inclusion or a fracture in a faulty fastener, and the length of a good fastener. However, the length of the fastener changes as tension is applied to the fastener. Therefore, a change in time of flight occurs as a function of axial tension.

Meisterling, U.S. Pat. No. 4,760,740, shows an extensometer unit coupled to an ultrasonic transducer which in turn is mounted to the head of a fastener. The Meisterling extensometer unit contains signal generating, signal receiving and signal processing circuitry of a general nature. An example of an extensometer circuit is shown by McFaul et al., U.S. Pat. No. 3,759,090.

Jones, U.S. Pat. No. 4,413,518, shows a bolt elongation measurement apparatus and a method of measuring bolts. The circuitry utilizes a microprocessor-based digital system including a binary counter which counts pulses generated by a high frequency oscillator during the time interval between the entry into the bolt of a first pulse and exit from the bolt of a second pulse derived from the reflection return of ultrasonic energy from the opposite end of the bolt. The count is applied to a computer for calculation of bolt length or of bolt stretch due to mechanical stress. The calculation also incorporates data input thereinto and corresponding to material velocity, stress correction factor, measurement temperature, and thermal correction factor. A digital filtering algorithm ensures an accurate and stable measurement. The receiver of the apparatus overcomes the problem of spurious ultrasonic reflection characteristics of threaded bolts by means of a dual characteristic echo sensing circuit to deal with stress-induced pulse distortion and a gain contour circuit to deal with spurious echo pulses that are characteristic of threaded bolts.

Couchman, U.S. Pat. No. 4,295,377, shows ultrasonic signal generation and detection circuitry which includes logic and timing circuits for generating an echo signal detection "window" This circuitry and detection technique of Couchman is also shown in his U.S. Pat. No. 4,294,122. The detection window establishes a time period when any signal received is taken as the desired echo pulse The time lapse between detection windows is adjustable and a function of the repetition rate of the primary ultrasonic pulses which Couchman provides at 100 to 2000 pulses per second.

Moore, U.S. Pat. No. 4,014,208, shows an ultrasonic device for measuring dimensional changes in a structural member. The device includes circuitry to double pulse a transducer to transmit an acoustic pulse into the member at one end for reflection from its other end with a period between paired pulses selected to cause the second echo received of the first pulse to coincide with the first echo of the second pulse. A voltage controlled oscillator is employed with a digital counter to time the period between paired pulses, the interval between successive paired pulses, and the time of a predetermined number of pulse pairs. The latter timing is used to alternatively shift the frequency of the voltage controlled oscillator to cause the first echo of the second pulse to be offset in phase from the coincidence position it might have at the central frequency. Phase detection and integration of the echo pulse coincidence during alternately high and low frequency offsets produces a phase-sensitive feedback signal to the voltage controlled oscillator to drive its central frequency toward precise coincidence.

Kibblewhite, U.S. Pat. No. 4,846,001, shows a fastener with an ultrasonic transducer affixed thereto. Electronic source pulses are applied to the transducer and electrical echoes produced by reflected ultrasonic waves are sensed. Kibblewhite measures a change in mechanical stress in the fastener by measuring a change in bolt stretch as a function of change in time of flight of echo measurement. Three time of flight measurement schemes are discussed. These are (1) a direct timing technique, (2) an indirect timing technique, and (3) a double pulsing technique.

A direct timing technique involves the measurement of the time interval between a source pulse (drive pulse) and the received echo. An indirect timing technique involves timing from the first echo to the second echo of a particular source pulse. In a double pulsing technique, two source pulses are transmitted, one after another. The time interval between these two pulses is adjusted so that the second echo from the first of the two source pulses coincides with the first echo from the second of the two source pulses.

Kibblewhite also discusses various echo detection techniques which can reduce the delay time of waiting for echoes of the previous pulse to die down. These detection techniques include (a) a fundamental frequency detection technique, (b) an acoustic impedance detection technique, (c) a harmonic resonance frequency detection technique and (d) a phase detection technique.

While the above-cited devices and methods can provide reliable information about a fastener, they have limitations in use. These techniques rely on averaging techniques to achieve their accuracy Therefore, they are capable of either high accuracy or high measurement rate and are generally used for taking measurements before and after tightening.

What is desired is an intelligent drive/sense ultrasonic signal circuit for measuring time of flight of pulse-echo time with greater accuracy.

What is secondly desired is ultrasonic signal drive/sense circuitry which achieves both high accuracy and high measurement rate and hence is useful for the control of ultrasonic measured tension during tightening.

What is further desired is ultrasonic signal drive/sense circuitry which does not require an extended delay time between transmitted pulses.

What is also desired is such drive/sense circuitry which uses a window for detecting an echo pulse and which can automatically select an optimum echo detection threshold for detecting an echo pulse.

What is further desired is such drive/sense circuitry which can automatically adjust the time position window for echo detection.

What is additionally desired is such drive/sense circuitry which automatically adjusts pulse drive voltage to compensate for variations in ultrasonic transducer electrical and acoustic efficiency and in fastener geometry.

What is even further desired is such drive/sense circuitry which can operate in an interleaved pulsing mode where pulse time is chosen so that echoes from the previous pulses fall outside the time acceptance window of the current measurement.

What is additionally desired is such drive/sense circuitry which can be adjusted to measure time of flight from a pulse to its echo, or from a pulse to its successive echo (reflections) or from its echo to a successive echo of that echo.

What is further additionally desired is such drive/sense circuitry which can operate with pulse repetition rates up to 10 KHz.

SUMMARY OF THE INVENTION

The objects of the present invention are realized in ultrasonic signal drive/sense circuitry, which is connectable to a fastener through an ultrasonic transducer, for calculating instantaneous tension in the fastener as measured by change in reflected pulse-times of flight.

A 16-bit software driven microcontroller sequences and times the operations of circuit components peripheral to it; and also provides time of flight calculations, calibration calculations, detection threshold calculations, sampling rate calculations and pulse amplitude calculations based on statistical data sampled and input thereinto. The selection of a microcontroller is for economy of manufacture and size. The microcontroller functions can be implemented by alternate types of circuitry.

Read only memory (ROM), random access memory (RAM) and an universal asynchronous receiver transmitter unit (UART) are each connected to the microcontroller or provided integrated with the microcontroller.

The microcontroller controls the output level of a high voltage signal generator through the use of pulse width modulation and feedback provided by an analog to digital converter. The microcontroller, thereafter, generates source pulses from the high voltage signal through the control of pulse drive circuitry interfaced thereto by a programmable high speed input/output buffer circuit. These source pulses are applied to a fastener through an ultrasonic transducer.

Received echo pulses, including successive reflections, are sensed from the ultrasonic transducer by a tuned pulse amplifier which inturn feeds echo detection circuitry. This echo detection circuitry includes programmable thresholding, setable from the microcontroller through a programmable input/output buffer circuit as well as, a digital to analog circuit within the echo detection circuitry.

Timing circuitry using both analog and digital techniques receives detection signals from the echo detection circuitry and provides digital timing information as well as two 180 degree out of phase analog ramp signals (anti-phase signals) to the microcontroller through the analog to digital converter circuit, the programmable input/output buffer circuit and a digital counter.

The source pulses sent to the ultrasonic transducer exceed 15 volts peak to peak, and are preferably in the 15 to 400 volt d.c. range, with pulse widths in the 50 to 100 nanosecond range. Pulse leading edge (fall or rise) times are preferably less than 10–20 ns. However, these fall or rise times must be less than 100 ns when an ultrasonic transducer with a fundamental resonant frequency of 10 MHz is used. Pulse periods are preferably in the 100 microsecond to 100 millisecond range.

Recalibration of the analog time measurement circuitry occurs on request. Optimization of the pulse voltage and the echo detection circuitry occurs for each fastener prior to tightening.

A time measurement algorithm is implemented in microcontroller software which averages incoming signal measurements. This algorithm includes the following steps:

a) Take and store the first measurement and set an acceptance window at this time +/− the echo waveform period (i.e. not echo/echo period) divided by 2. This is 50 ns for a 10 MHz signal.

b) Take the remaining (n−1) measurements checking that each lies within the acceptance window. If a measurement is outside this window, discard the measurement. If a measurement is within the window, add it to time-sum and add the modulus of the deviation from the first reading to deviation-sum.

c) If n divided by 4 measurements are discarded because they are outside the acceptance window, abort and restart measurement process.

d) Calculate the average scatter as deviation-sum divided by (n−1). If this exceeds the specified scatter limit, abort and restart measurement process.

e) Calculate the average time of flight time-sum divided by n.

f) If no valid time of flight measurement has been made when a request for data is received, a fault message such as uncoupled, scatter, trigger, will be transmitted.

The software contained in memory operates the hardware to generate high voltage pulses for an optimum drive voltage for the environment. The detection threshold for echo detection is likewise programmably set for optimum echo detection. The invention will accept changes to program parameters through the UART "port".

Ultrasonic time of flight is measured using the two anti-phase reference ramp signals; with calibration values for generating these ramp signals being periodically re-determined.

The drive/sense circuitry operates in reference to the two anti-phase overlapping ramp signals and to two timing pulse trains, one operating at 5 MHz and the second operating at 10 MHz. This enables the circuitry to generate and detect ultrasonic pulses at rates as high as 10 KHz and measure ultrasonic pulse to echo times to a resolution of 200 picoseconds.

The circuitry utilizes these two anti-phase ramp signals as well as the 5 MHz and 10 MHz clock pulses (reference pulse trains) to detect the time of flight between the source pulse and the first echo, or between pre-selected echoes (e.g. first and third).

If an interleaving mode of operation is selected, these operations are conducted according to an algorithm which uses this information to provide a subsequent source pulse which is out of phase with the echoes, thereby permitting the taking a new measurement of time of flight immediately after completing the prior measurement. This technique is called "interleaving".

DESCRIPTION OF THE DRAWINGS

The features, operation and advantages of the present invention will be readily understood from a reading of the following Detailed Description of the Invention in conjunction with the attached drawings in which like numerals refer to like elements and in which:

FIGS. 3A and 3B show pulse time plot for regular (repetitive) mode of operation for the drive/sense circuitry and a pulse time plot for interleaved mode of operation;

FIGS. 6A-1, 6A-2, 6B-1, 6B-2, 6C-1, 6C-2, 6D-1, 6D-2, 6E-1, 6E-2, 6F, 6G-1, and 6G-2 are program flow charts for the software subroutines resident in the programmable microcontroller of FIGS. 7A-1 and 7A-2; and FIGS. 7A-1, 7A-2, 7B-1, 7B-2, 7B-3, 7B-4, 7C-1, 7C-2, 7D-1, and 7D-2 show a detailed circuit implementation for the block diagram shown in FIG. 1.

DETAILED DESCRIPTION OF THE INVENTION

Figure 1:
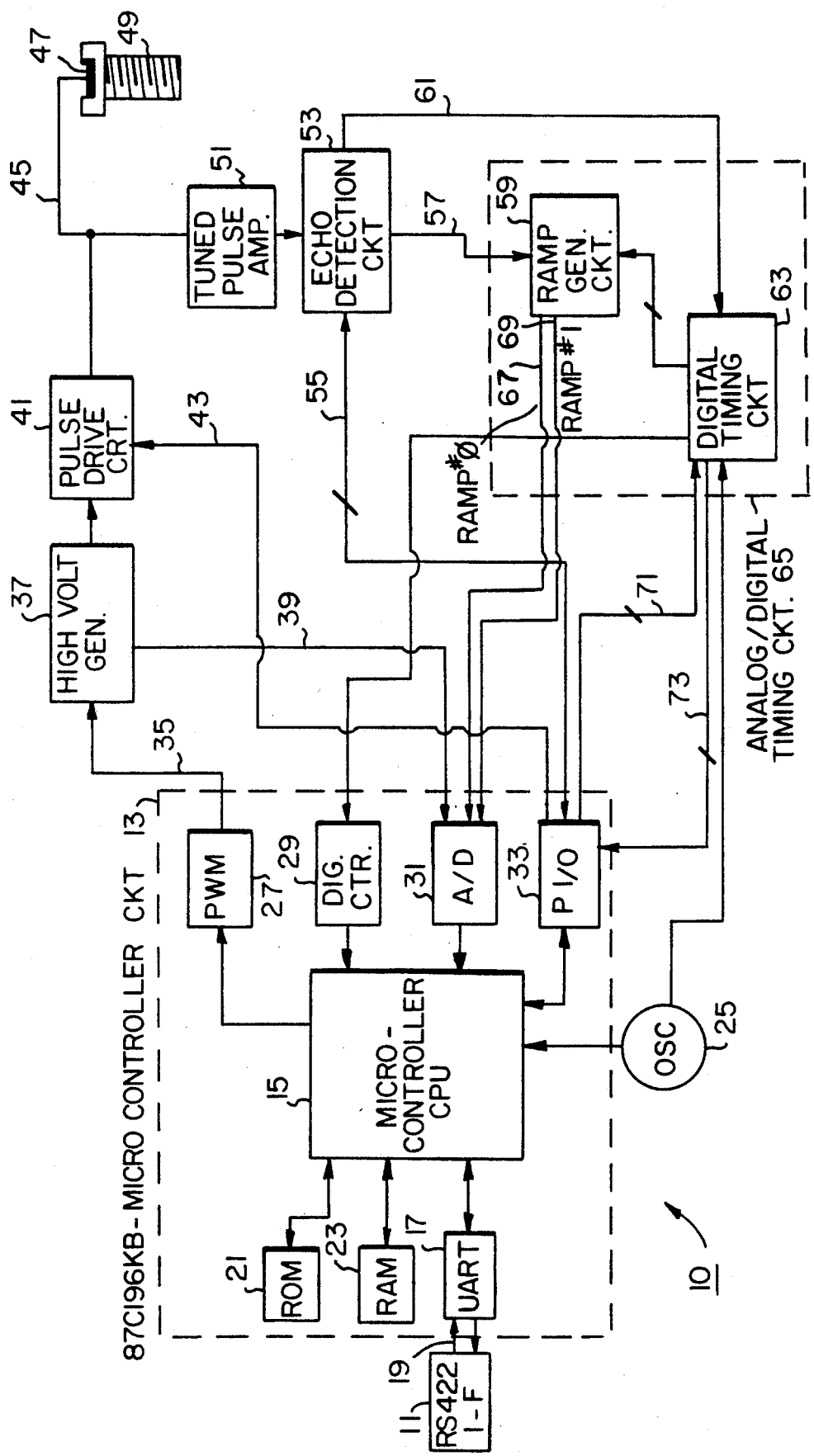
FIG. 1 is a general block diagram for the drive/sense circuitry.
Figure 2A:
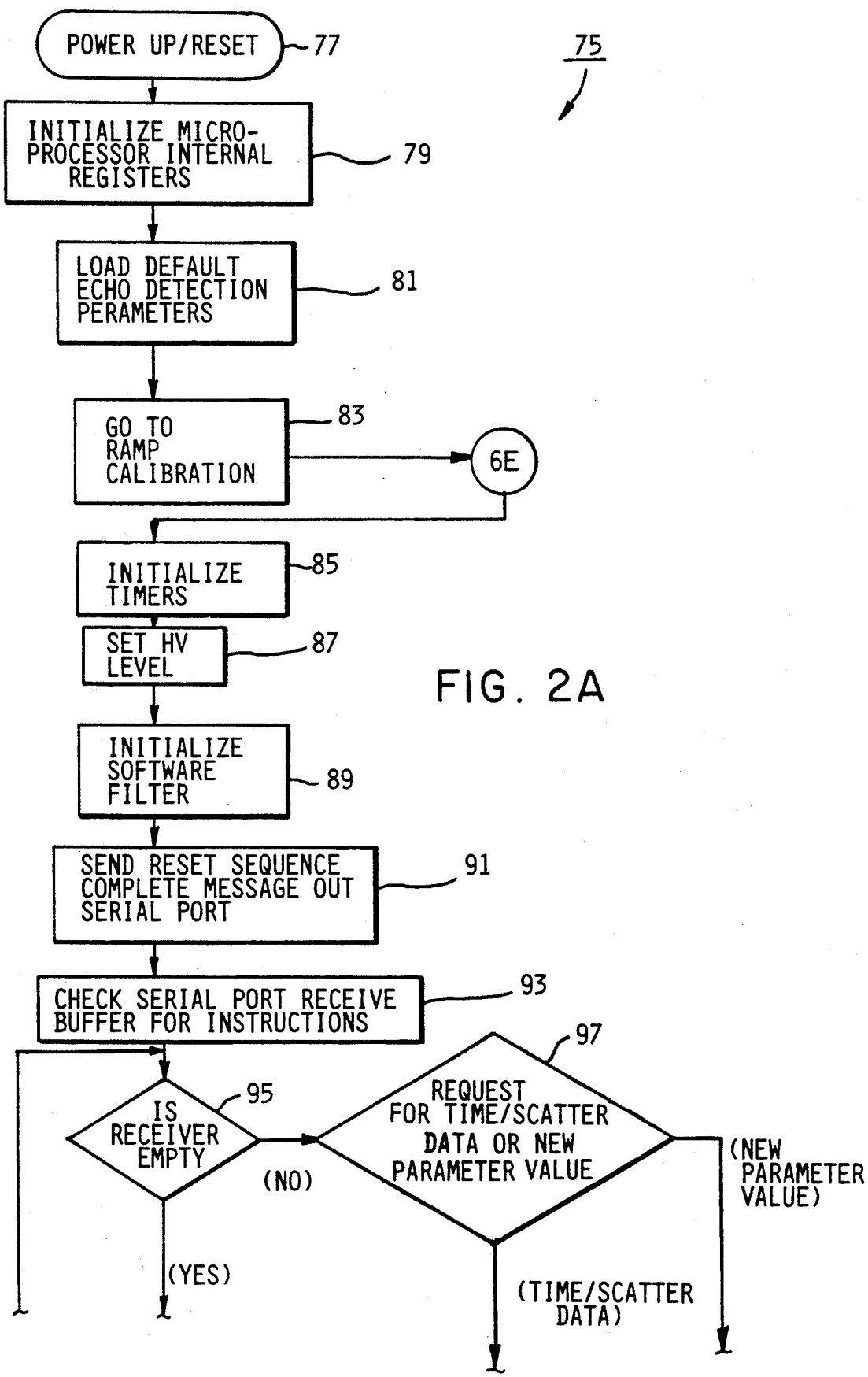
FIGS. 2A and 2B show a program flow chart for the initialization and main program for the programmable microcontroller of FIG. 1.
Figure 2B:
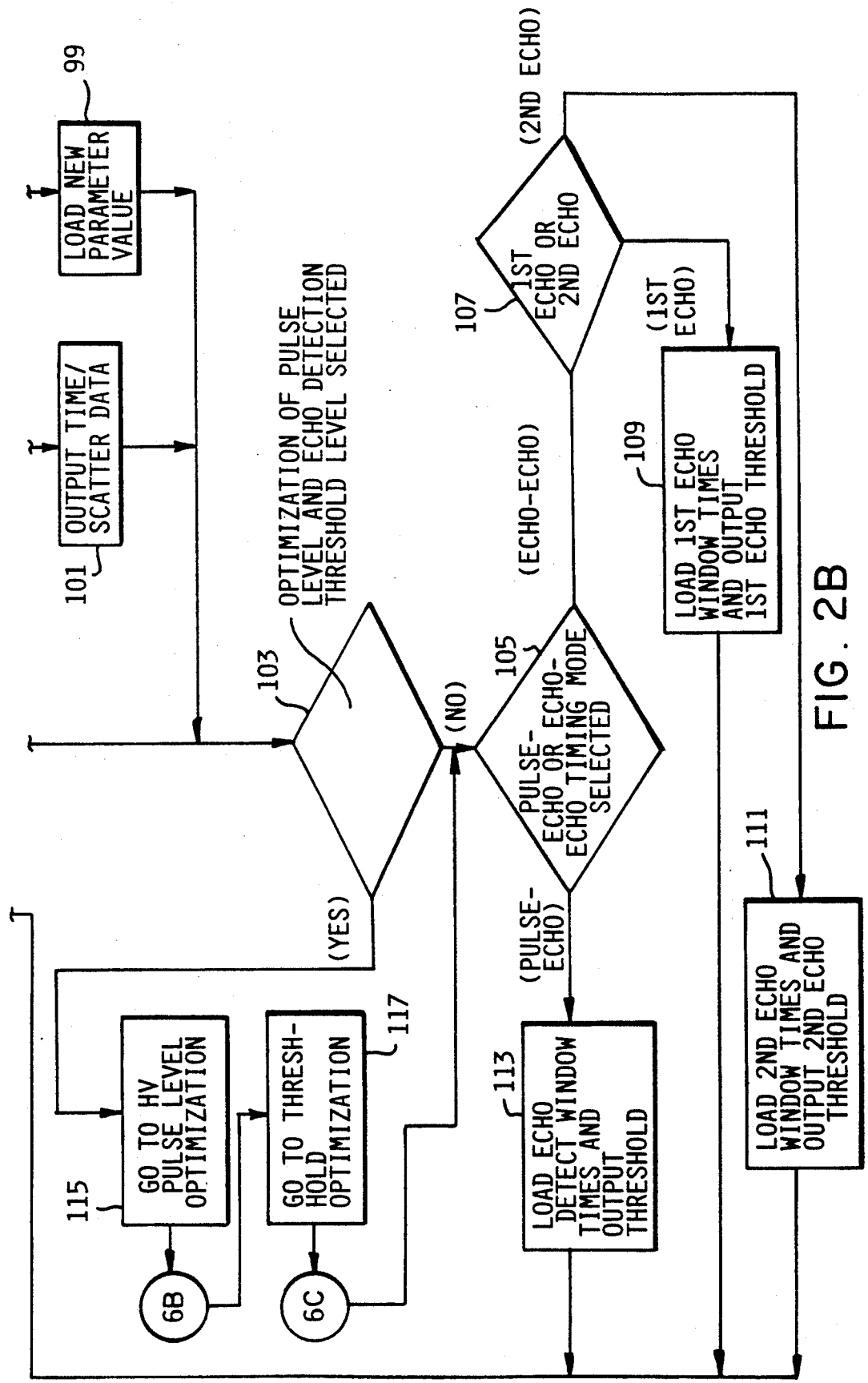

The ultrasonic pulse drive/sense circuitry 10 of the present invention is shown in FIG. 1. An operator, or other source of input or output data, is provided access to this circuitry through an RS422 interface port 11. A microcontroller circuit 13 is implemented by a model 87C196KB Intel Corporation microcontroller circuit 13. Within this microcontroller circuit 13 is constructed a programmable central processing unit (CPU) 15. This CPU 15 has a two way connection to a universal asynchronous receiver transmitter (UART) circuit 17. UART 17 is connected through two way transmission bus 19 to the RS422 port 11.

CPU 15 has associated therewith, either internally or externally, a programmable read only memory, ROM 21 and a programmable random access memory, RAM 23. Resident within ROM 21 is an initialization and main software program for controlling the operation of the circuit 10. The RAM 23 is used for storing data, program variables, and other program software.

The microcontroller circuit 13, and specifically the CPU 15, is driven from an external 10 MHz oscillator 25. This oscillator 25 also provides timing pulses to a digital timing circuit to be described below.

Connected on an output from CPU 15 is a pulse width modulation circuit 27 which receives instruction signals from the CPU 15. A digital counter 29 receives count pulses from the circuitry described below and inputs this count into the CPU 15. An analog/digital converter circuit 31 receives analog signals from circuitry described below and converts these into digital input signals sent to the CPU 15, while a programmable input/output circuit 33 provides a two way interface between the circuitry described below and the CPU 15.

A switching control signal 35, from the pulse width modulator 27, is sent to a high voltage generator 37 which generates a d.c. voltage variable from 15 volts d.c. to 400 volts d.c. A status line 39 is connected from the output of the high voltage generator 37 to the CPU 15 through the A/D converter 31. The output from the high voltage generator 37 is also connected to a pulse drive circuit 41.

Pulse drive circuit 41 is operated under control signals 43 provided to it from the CPU 15 through the programmable I/O circuit 33. Pulse drive circuit 41 provides the source (or drive) pulses through an electrical connection 45 to an ultrasonic transducer 47 positioned on a fastener 49. The ultrasonic transducer 47 is a bi-directional device, therefore reflection pulses (echoes) likewise appear on the line 45.

A tuned pulse amplifier circuit 51 senses the echoes or reflection pulses on the line 45, as well as the source pulses on that line, and provides an amplified signal to an echo detection circuit 53.

Echo detection circuit 53 has threshold values and sampling times (windows) programmably set by instructions and sent via a parallel connection 55 from the CPU 15 via the I/O circuit 33. A first output 57 from the echo detection circuit 53 is connected as an input into a ramp generator circuit 59. A second output 61 from the echo detection circuit 53 is connected as an input into a digital timing circuit 63. The ramp generator circuit 59 and the digital timing circuit 63 form a analog/digital timing circuit 65.

The ramp generator circuit 59 provides two outputs, on their own dedicated connection lines, the first being a first ramp signal 67 and the second being a second ramp signal 69. The ramp signals 67, 69 are connected into the CPU 15 through the A/D converter circuit 31. As was made reference above, the digital timing circuit 63 is connected to the oscillator 25 and receives 10 MHz timing pulses therefrom. The digital timing circuit 63 has a bi-directional connection 71, 73 with the CPU 15 through the programmable I/O circuit 33.

Figures 1, 6A:
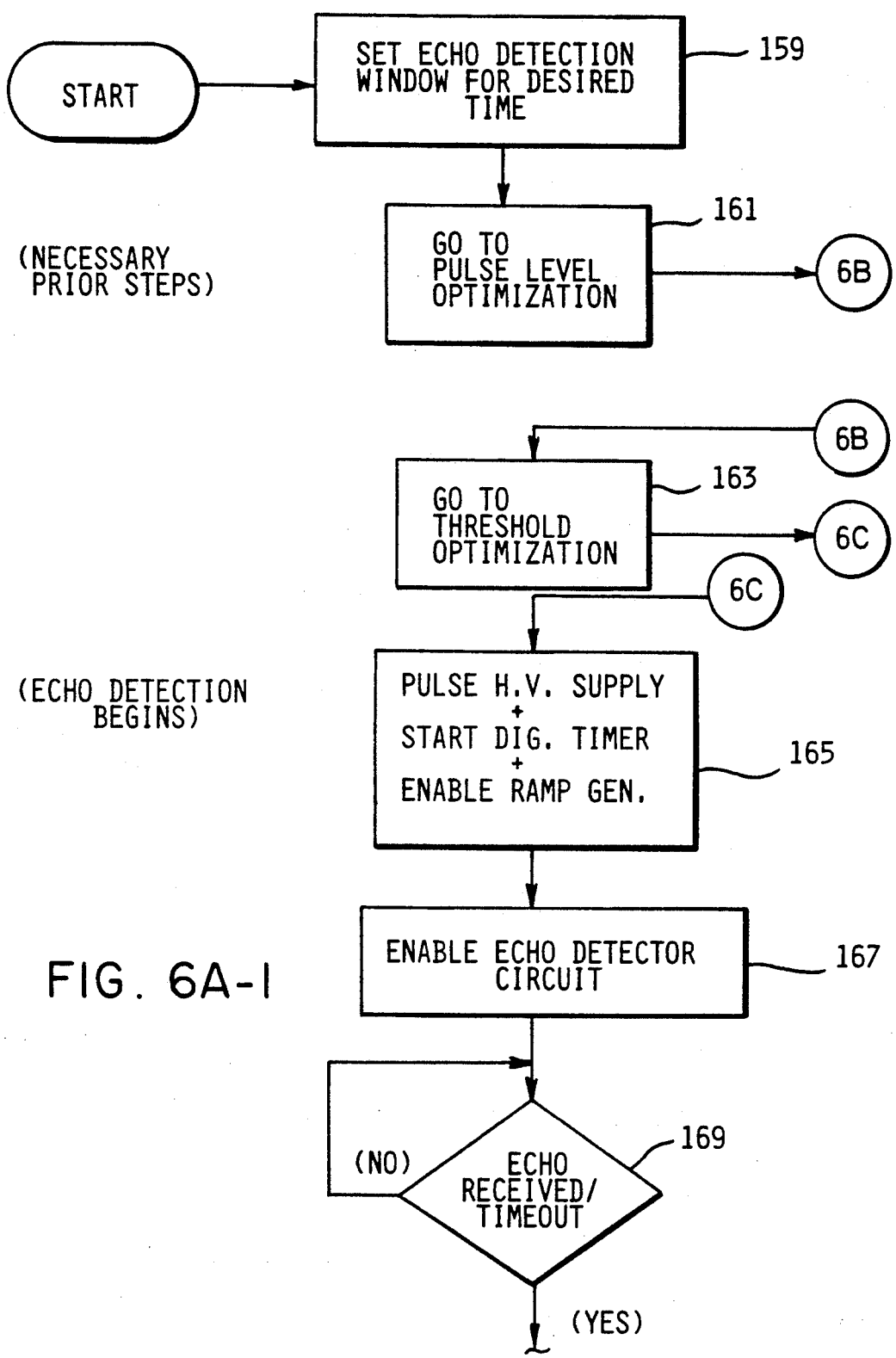
Figures 2, 6A:
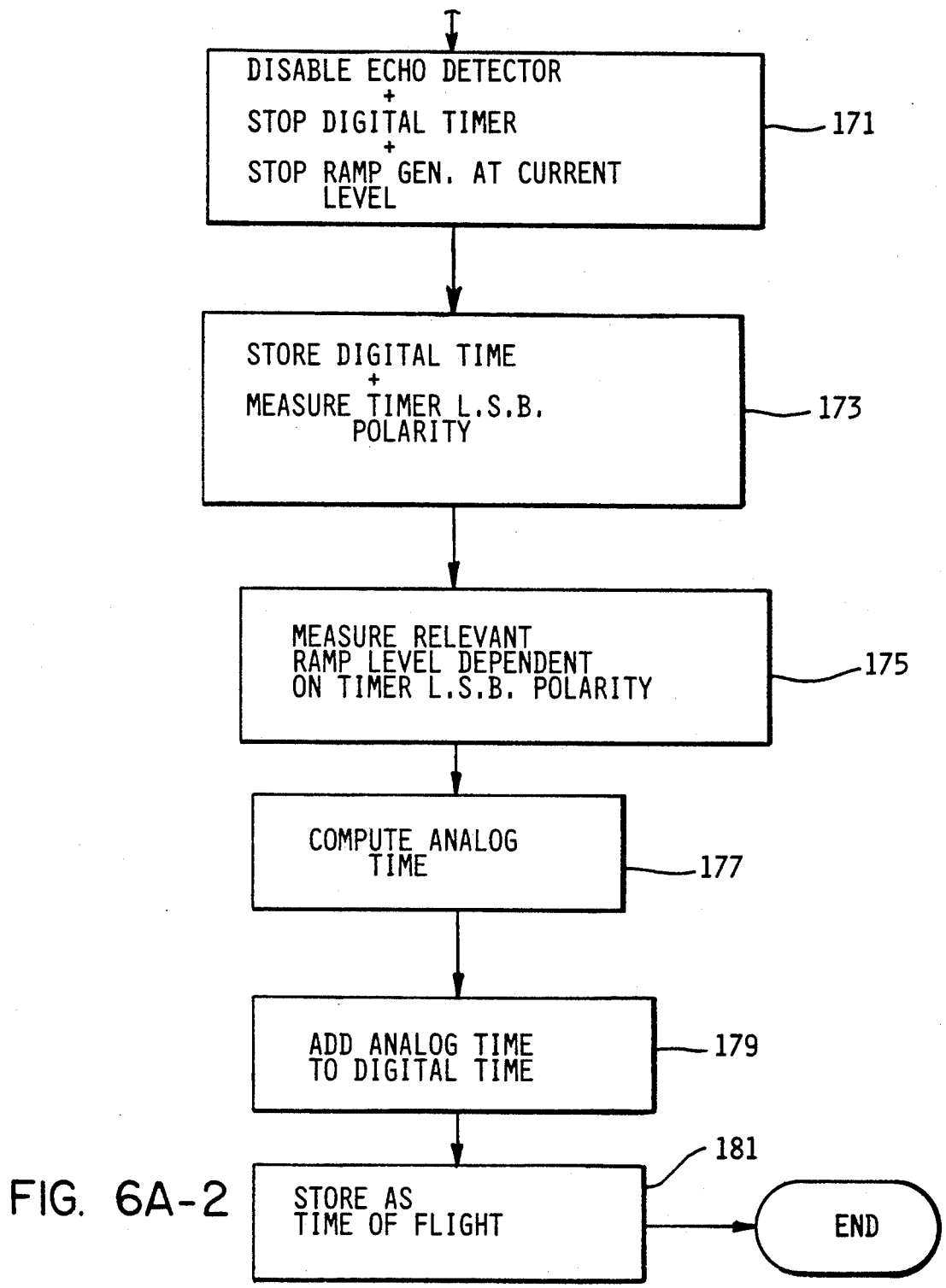

Contained within the memory associated with the central processing unit 15 is an initialization and main program computer software which is represented by the program flow chart 75 of FIG. 2. When the circuitry 10 of FIG. 1 is powered-up, it automatically goes through a reset sequence 77. Thereafter, the microprocessor 15 has its internal registers initialized, step 79. Next, default echo detection parameters are loaded 81 into the registers of the microcontroller circuit. Following this, the circuitry goes through a ramp calibration routine 83. Here the software routine described below in connection with FIG. 6e is conducted.

After this step, the internal timers within the microcontroller are initialized, step 85. Thereafter, the high voltage level is set, step 87. Following this, the software filter circuitry is initialized, step 89. Thereafter, a reset sequence complete message is sent out of the serial port 11, step 91. Then the serial port receive buffer is checked for instructions, step 93. This completes the initialization portion of the program shown in FIG. 2. The various circuit components and program components recited will be discussed further below.

Next, the software directs the circuitry 10 into the main program loop which continuously loops around until the power is removed from the circuitry 10.

The first step in the main program loop is to check whether the receiver buffer is empty, step 95. If it is not empty, the registers are checked for a request for either time/scatter data or new parameter values. If a new parameter value or command is requested, the new parameter value or command is loaded into the microcontroller 13 circuitry, step 99. If, in step 97, time/scatter data is requested, this time/scatter data is output to the circuitry in step 101.

If the receiver is empty in step 95, or after the steps 99, 101 are performed, the circuitry looks to determine whether optimization of pulse level and echo detection threshold level is selected, step 103. If there is no such selection, the circuit registers are interrogated, step 105, to determine whether a pulse-echo or an echo-echo timing mode is selected. If an echo-echo timing mode is selected, the circuitry is interrogated to determine whether a first echo or a second echo has been designated, step 107. If a first echo has been designated, then first echo window times and output of first echo threshold data is loaded into the circuitry in step 109. If a second echo has been determined to be designated by step 107, the second echo window times and output second echo threshold data are loaded into the circuitry in step 111.

On the other hand, if as a result of interrogation step 105, a pulse-echo mode has been selected, the echo detection window times and output threshold data for this mode are loaded into the circuitry in step 113.

In interrogation step 103, if it has been determined that pulse level and echo detection threshold levels have been selected, then the program in step 115 is directed into high voltage pulse level optimization. This is a program routine described further in connection with FIG. 6b below. Following the operation of this routine of FIG. 6b, the program returns to the direction step 117 where in it goes to a threshold optimization routine described below in connection with FIG. 6c. Following the performance of this routine, the program returns to interrogation step 105.

Upon the completion of any of the steps 109, 111 or 113, the program is directed back to interrogation step 95 where the receiver is interrogated to determine if it is empty. This portion of the program continues to loop, indefinitely, until the power is removed from the circuitry 10.

The main concern of the circuitry 10 is the measurement of longitudinal tension applied to the fastener 49 during tightening. It has been previously determined by empirical data that as the fastener 49 is tightened and the longitudinal tension thereon increases, the time of flight of an echo, i.e. the elapsed time between the application of a source/drive pulse to the head of the fastener 49 through the ultrasonic transducer 47 and the receiving of the reflection from the end of the fastener, i.e. the echo, is the time of flight of that pulse. Moreover, as the fastener 49 goes through incremental changes in length with incremental changes in tightening, the successive measurement of time of flight changes.

Figures 1, 7A:
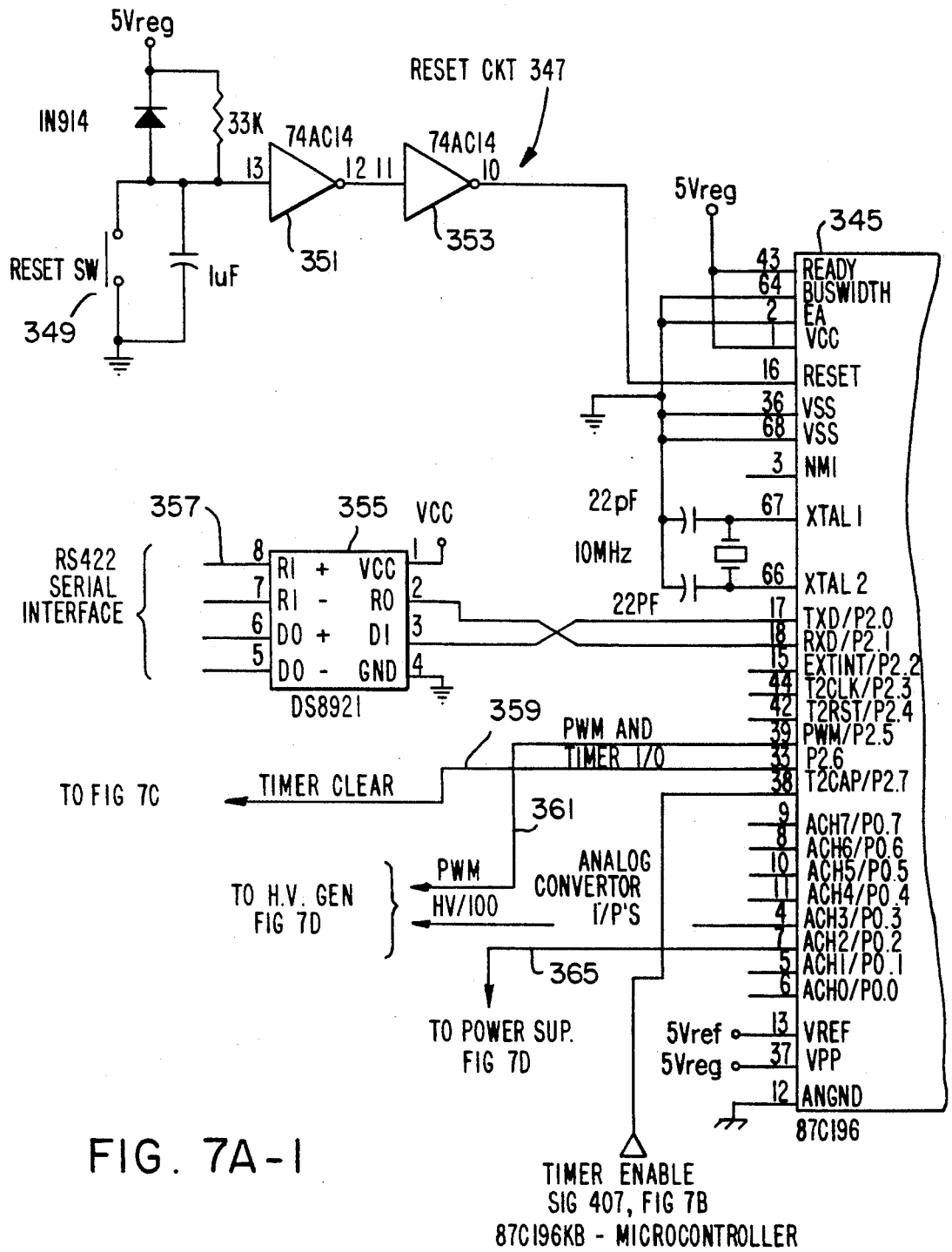
Figures 1, 7B:
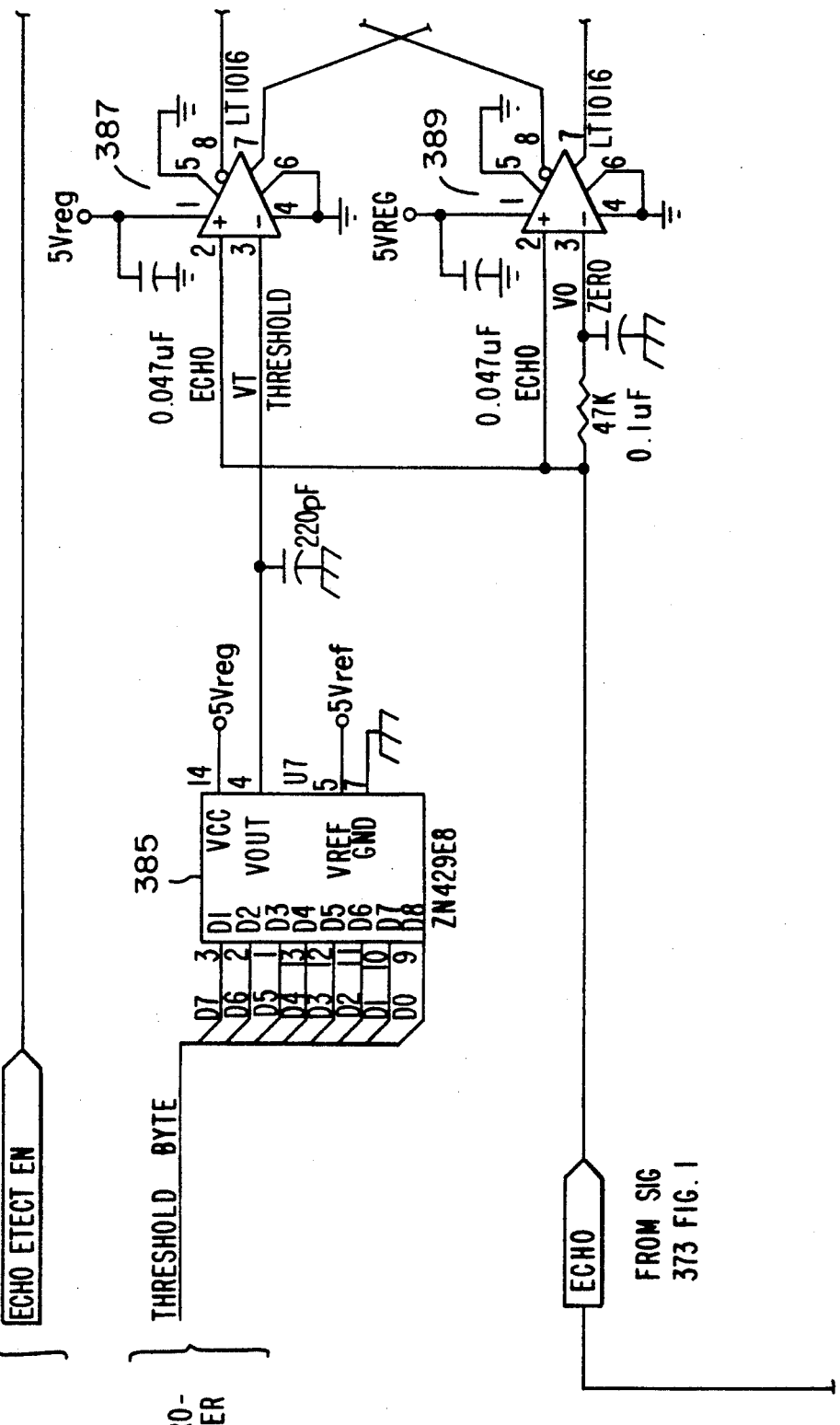
Figures 2, 7B:
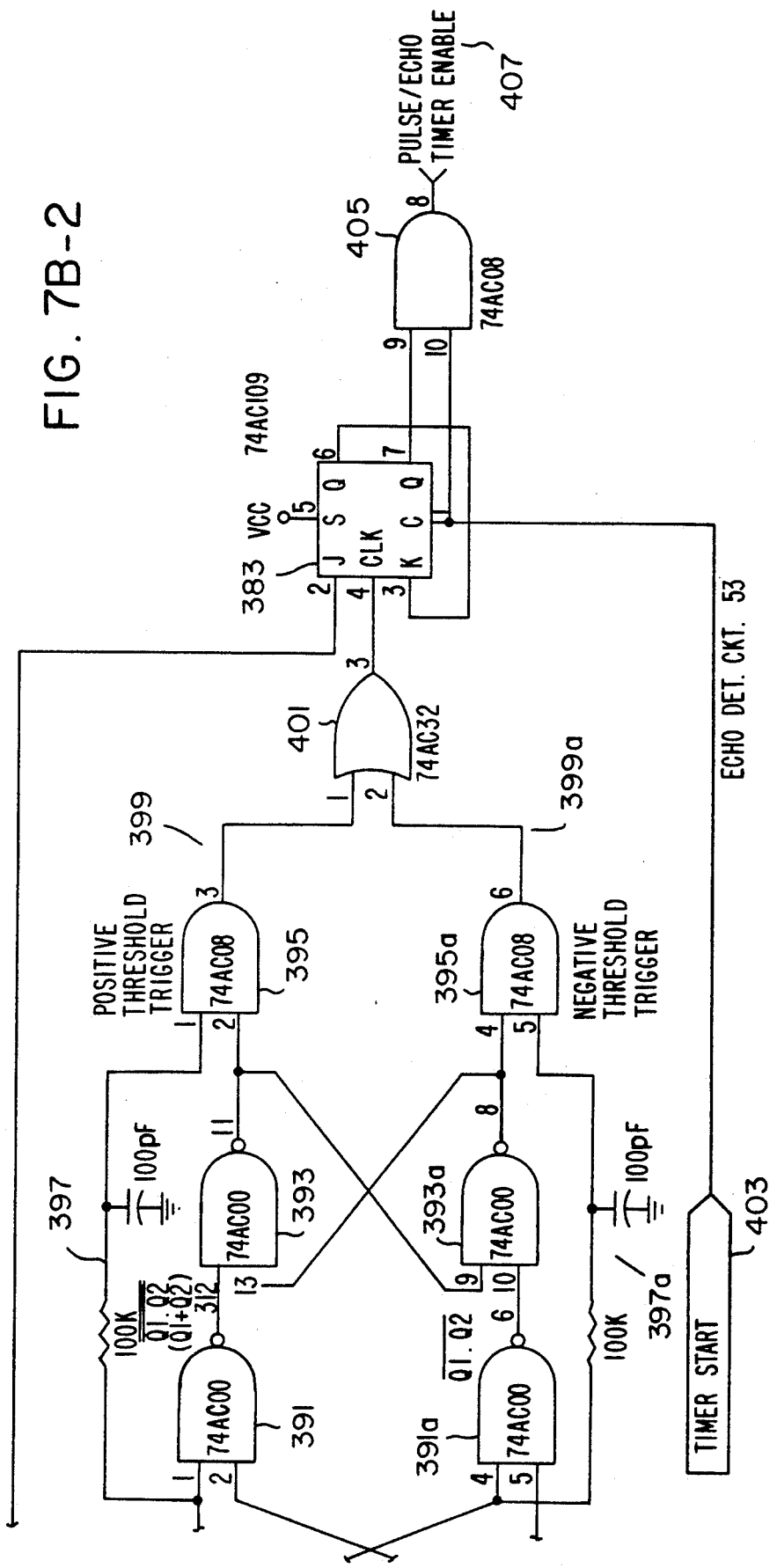
Figures 3, 7B:
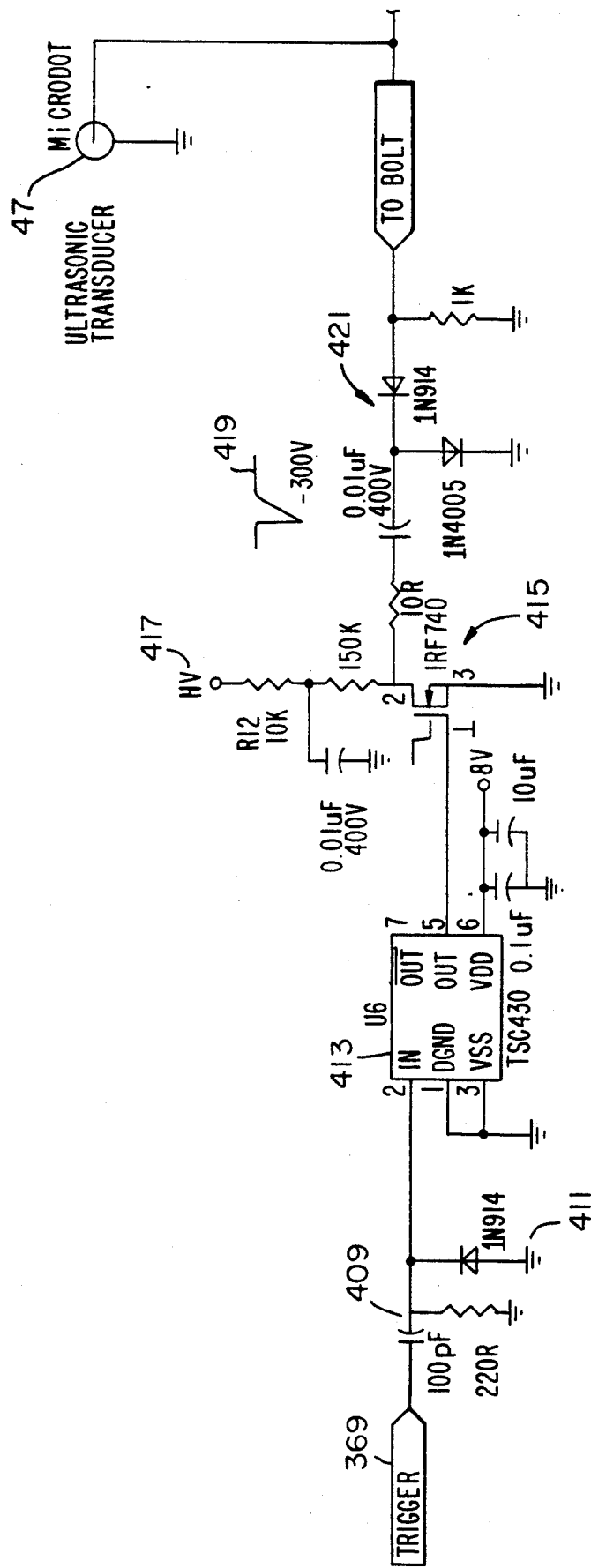
Figures 4, 7B:
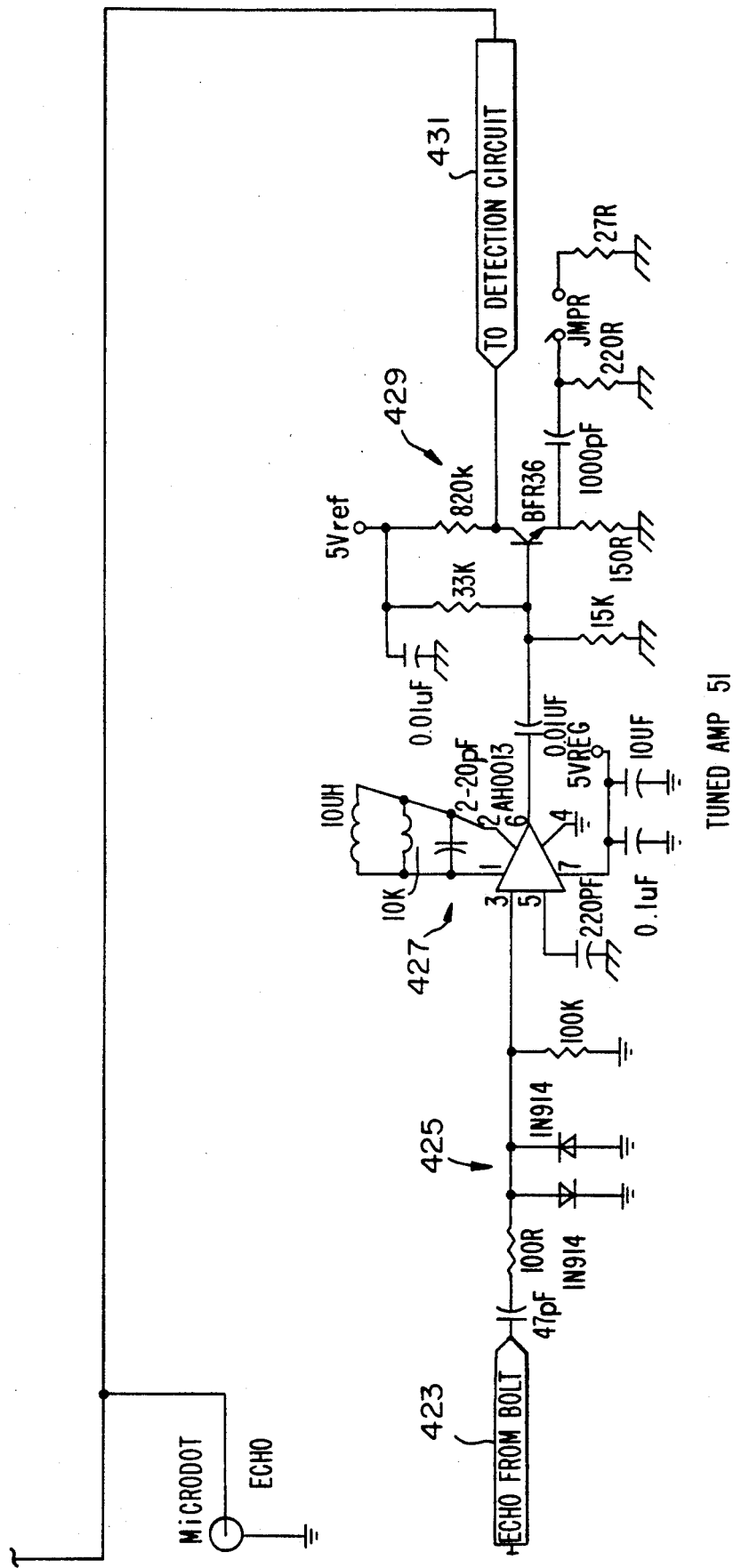

FIG. 3 shows pulse time plots for regular (repetitive) mode of operation for the drive sense circuitry 10 and a pulse time plot for an interleaved mode of operation for this circuitry 10. The repetitive mode 119 operates with a plurality of pulses that are separated by a time period Ta. This time period Ta is preferably greater than 10T, where T is the time of flight for an echo. This period between source/drive pulses allows echoes to subside so that successive reflections do not coincide with other echoes to give false readings. A time of flight for a four inch bolt is typically about 35 microseconds.

In the repetitive mode 119 a first source/drive pulse 123 is applied to the ultrasonic transducer 47 and the time of flight TOF is measured to the first echo 125. This time of flight 131 is then stored in the circuitry of the microcontroller 13.

As part of this measurement, an acceptance window 133 is established for the echo 125. This acceptance window determines when the circuitry begins to look for the echo at time $T_0$ and when it stops looking for the echo at time $T_1$. Once the recessive echoes from source/drive pulse 123 subside sufficiently, i.e. at the tenth echo, a second source/drive pulse 129 is applied to the ultrasonic transducer 47.

In the interleaved mode of operation 121, successive source/drive pulses are not applied to the ultrasonic transducer 47 on regular intervals established at 10T, i.e. beyond the tenth echo of the predecessor pulse. In the interleaved mode of operation 121, successive source/drive pulses are generated to the transducer 47 and interleaved between primary reflections of the predecessor source/drive pulse. This interleaving takes into consideration the instantaneous position of dominant echoes from predecessor pulse source/drive pulses and places new source/drive pulses on a time scale in-between these echoes so as not to create a coincidence of reflections, i.e. echoes from predecessor pulses coinciding so that a false reading is obtained.

In any given instance of time, the time placement of an echo can be statistically determined. This time placement of the expected occurrence of an echo, whether that echo be the first echo, the second echo, the third echo, or on through the tenth echo, is reasonably statistically determinable.

In the interleave mode of operation 121, a first source/drive pulse 137 generates a first echo 135 which occurs at a time of flight T 131' which would be the same time of flight for the repetitive mode 119. An elapsed time period is calculated for each new source/drive pulse generated in the interleaved mode 121. This period Ta' establishes when a second source/drive pulse 143 is applied to the ultrasonic transducer 47. This second source/drive pulse 143 creates its first echo 139 which occurs at interleaved times with echoes 138, 142 and 145 from the first source/drive pulse 137.

Again, in the second cycle, the time of flight 131, between the primary echo 139 and the source/drive pulse 143 is the measurement being made. This process is repeated for successive cycles.

In the third cycle, a source/drive pulse is applied in-between the echoes of the two previous pulses, for example, before the occurrence of the fifth echo 149 from the first source/drive pulse 137 and the third echo 151 from the second source/drive pulse 143. The time of flight 131' between the first echo 153 and the third source/drive pulse 147 is measured. First and second echoes 153, 155 occur in-between further echoes from the first and second source/drive pulses 137, 143. This process is repeated for a fourth cycle where a fourth source/drive pulse 157 is applied to the ultrasonic transducer 47 prior to the occurrence of additional echoes from the first, second, and third source/drive pulses 137, 143, 147.

In the interleaved mode of operation 121, this accounting procedure continues up through ten source/drive pulses. As with the repetitive mode 119, echoes beyond the tenth echo of any given source/drive pulse have subsided to an amplitude level which is beyond interfering with the accuracy of the circuitry, and therefore do not have to be accounted for in the interleaving mode 121 calculations.

While the pulses shown in FIG. 3 are positive going pulses, the circuitry can be designed to operate on negative going pulses. In fact, the detailed circuitry discussed below in connection with FIGS. 7a-7d operates with negative going pulses.

Figure 4:
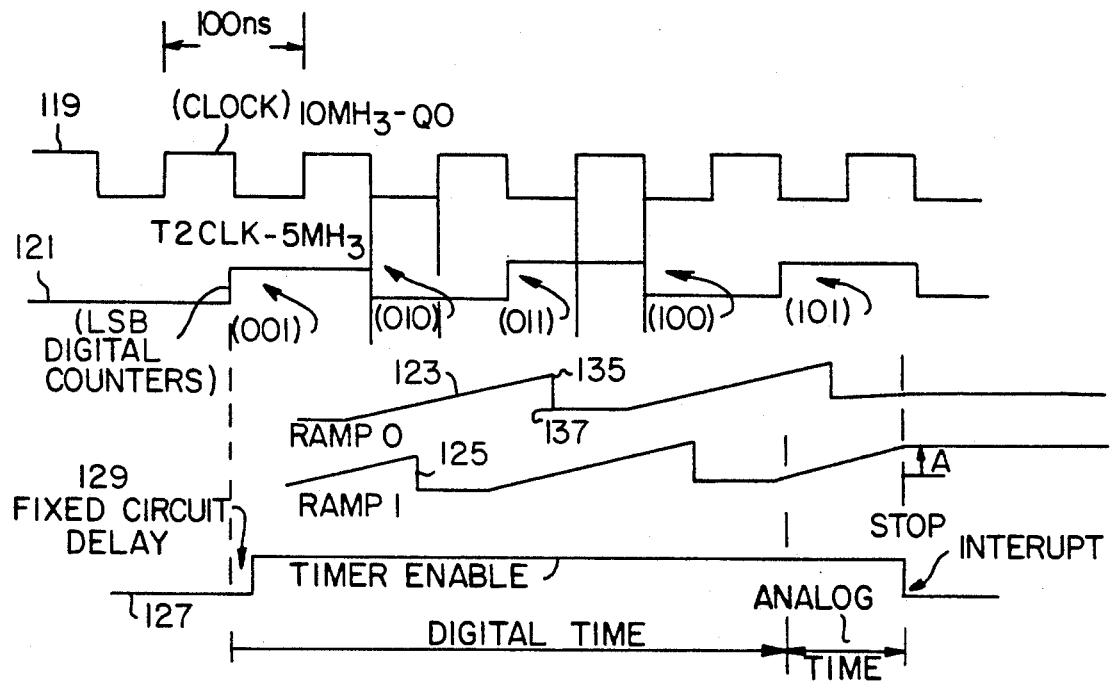
FIG. 4 shows typical time plots for the 10 MHz and 5 MHz reference signals and the two anti-phase ramp signals used in analog interpolation for establishing echo windows.

FIG. 4 shows the 10 MHz clock signal 119 provided by the oscillator 25 of FIG. 1. This clock signal has a period of 100 ns and is designated as signal $Q_0$ in the time of flight calculation performed within the CPU 15 of the microcontroller circuit 13.

The least significant bit (LSB) of the digital counter 29 of FIG. 1 flip-flops (changes) at a 5 MHz rate. The signal indicative of the state of this LSB of digital counter 29 is shown as signal 121 in FIG. 4. This signal 121 is indicated as symbol T2CLK in the calculation of time of flight carried out by the CPU 15.

The zero ramp signal 67 of FIG. 1 is plotted as ramp plot 123 on FIG. 4. Likewise, the one ramp signal 69 of FIG. 1 is plotted as ramp plot 125 on FIG. 4.

A timer enable signal 127 is generated by the CPU 115. This timer enable signal 127 is used by the echo detection circuit 5 of FIG. 1 in detecting echoes, and in particular in enabling echo detection windows such as those illustrated in FIG. 3. Also shown in FIG. 4 are the numeric state of the three least significant bits of the digital time count, for successive times along the 10 MHz and 5 MHz reference signals. The timer enable signal 129 goes positive when the counter state is "001". This occurs on the falling edge of the 10 MHz clock signal 119.

The time of flight calculation performed within CPU 15 is as follows:

$$T = (\text{digital time}) + (\text{analog time})$$

Where analog time is a fraction of the digital timing period. More specifically:

$$T = ((2 \times \text{T2CLK count} + Q_0) + (A-L)/(H-L)) \times 100 \text{ ns}$$

Where A is the ramp amplitude at the end of the timing period and L and H are predetermined ramp calibration values, L0 and H0, respectively when using ramp 0 to calculate analog time; and L1 and H1, respectively, when using ramp 1 to calculate analog time.

Figure 4B:
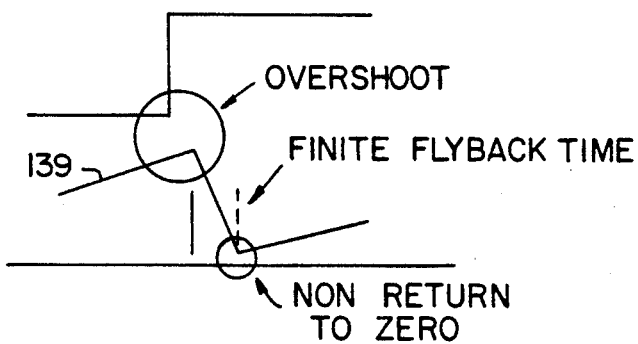
FIG. 4B shows a plot of sources of error for ramp analog time interpolation which errors are corrected for by the circuitry under program instructions.
Figure 4A:
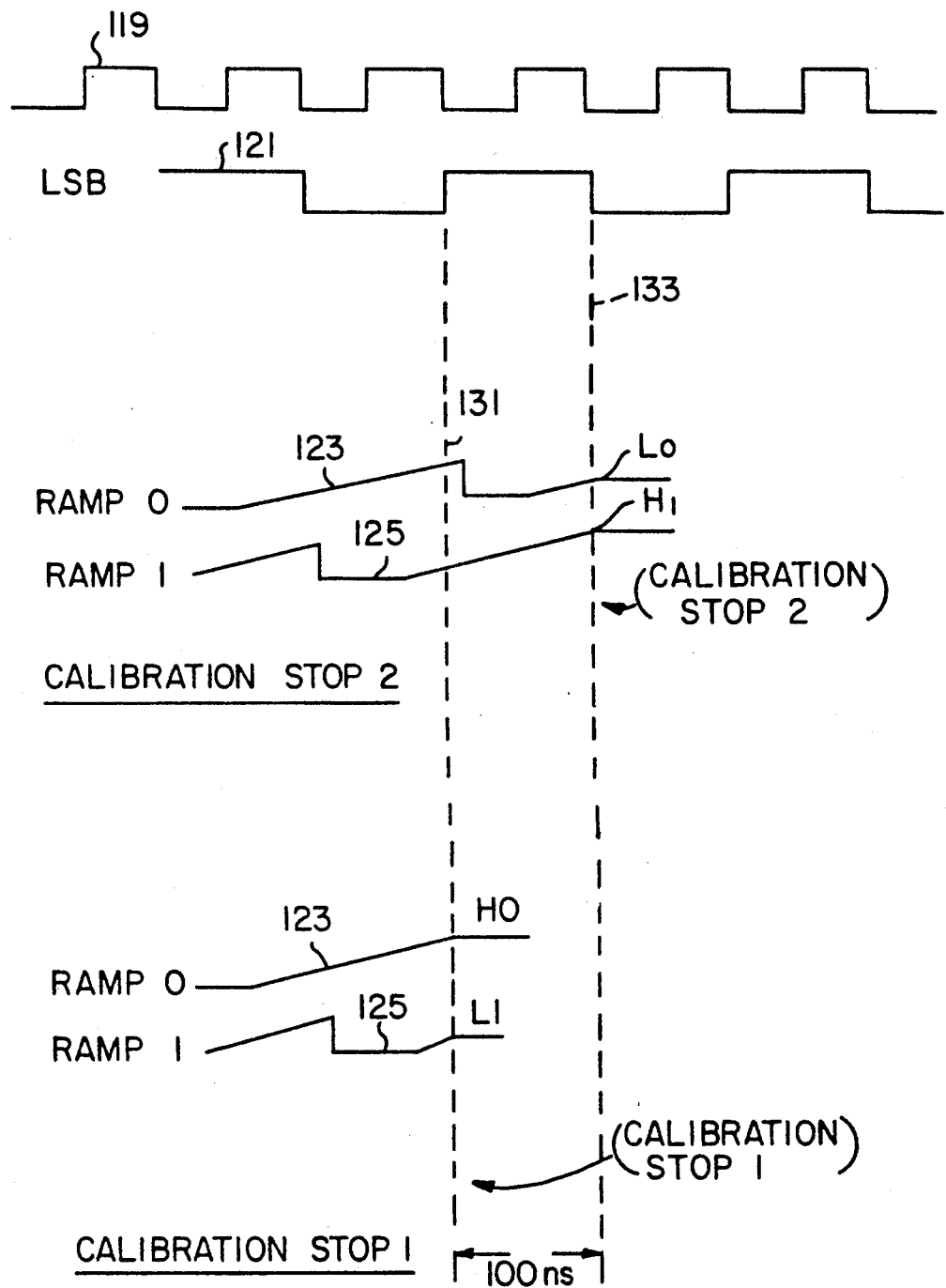
FIG. 4A shows a plot of calibration timing with respect to anti-phase ramp signals for analog time interpolation carried out by the circuitry under program instructions.

FIG. 4a illustrates calibration of analog timing ramps 67, 69, FIG. 1. Shown is the least significant bit (LSB) 121 of digital timing circuit 63 and the first ramp (ramp 0) signal 123 and the second ramp (ramp 1) signal 125, all of which are set running and remain so until operated upon.

A first calibration stop "time" 131 is generated producing a stop near the beginning of ramp 1, signal 125, and near the end of ramp 0, signal 123.

A second calibration stop "time" 133 is generated producing a stop near end of ramp 1, signal 125, and near the beginning of ramp 0, signal 123.

These first and second stop "times" 131, 133 are precisely 100 ns apart.

At the two stop "times" 131, 133 each ramp value of ramps 123, 125 is read. These readings provide four calibration data points, H0, L1, H1, L0, which are used in the analog time scaling calculations recited above and further described below.

FIG. 4b shows that in generating the analog timing ramps, one of which is shown as sawtooth wave 139, certain sources of error occur. These errors therefore contribute to ramp analog time interpolation errors. These errors include overshoot, finite flyback time and none-return-to zero. These errors are typical of high speed analog circuitry. The circuitry of the present invention is designed to compensate for these sources of error which naturally occur in analog circuitry through a calibration technique on request.

The echo detection circuit 53 of FIG. 1 places a "window" at a proper time position for looking for a particular echo. The echo detection circuit 53 has within it program registers for establishing the time-position of this "window".

The pulse level optimization software program, mentioned above and described below, establishes the amplitude of a source/drive pulse which therefore establishes the signal level of the first echo from that pulse and each successive echo thereof, FIGS. 3, 5.

The threshold optimization software program, mentioned above and described below, identifies and establishes the amplitude of the largest face of exposure 141, FIG. 5, of the echo. It also establishes the signal level for the positive threshold 143 or the negative threshold 145 for detecting the principal lobe (phase) 147 of a particular echo.

The threshold crossover point 149 for positive threshold, or 151 for negative threshold, is used to arm a timer stop circuit of the echo detection circuit 53. Threshold crossover is the point where an echo waveform crosses an established threshold level.

A stop signal 160 is generated at a predetermined zero crossover of the echo waveform following the threshold crossover point 149 used to arm the timer circuitry. Preferably, this is the very next zero crossover following the particular threshold crossover point 149 used to arm the timer stop circuitry.

The advantage to timing to a zero crossing rather than to a threshold value, as was previously done, is to eliminate the effect of echo signal variations and electrical and ultrasonic noise on time of flight measurements during tightening.

Figure 5:
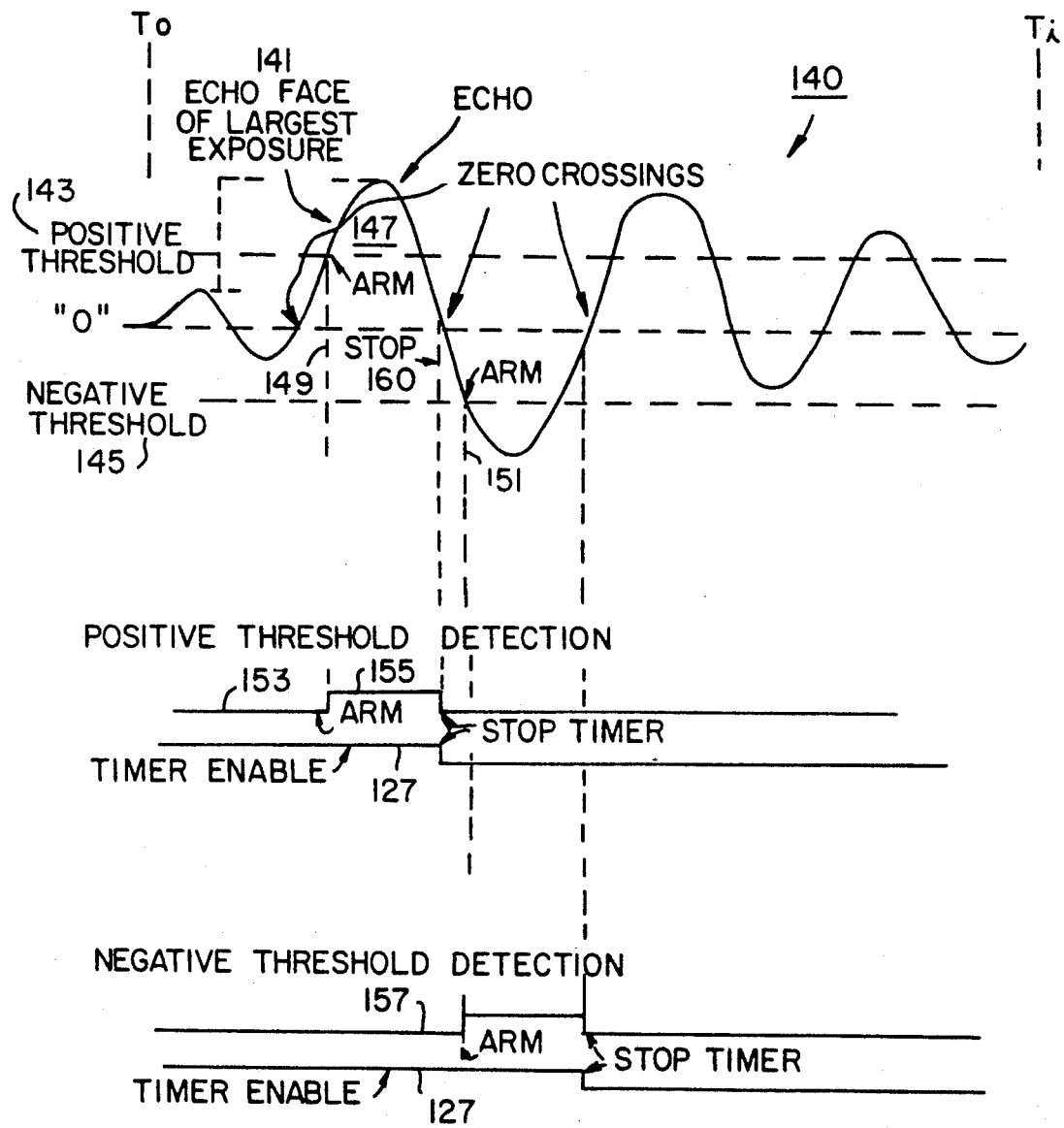
FIG. 5 shows a time plot of circuit enable signals for echo detection circuit timing for threshold and zero crossover.

The stop circuitry arming signal 153, 157 and timer enable signal 127 for positive threshold detection or for negative threshold detection are also shown in FIG. 5.

The operational features illustrated in FIGS. 3, 4, 4a and FIG. 5 are carried out within the circuitry 10 under the direction of computer software programs. These programs include the echo detection routine illustrated by the flow chart of FIG. 6a. Once this routine is started, an echo detection window for a desired time is set, step 159. Following this step, the program directs itself 161, to the pulse level optimization routine illustrated by the flow chart shown as FIG. 6b. After this routine is conducted, the program directs itself 163, to the threshold optimization routine illustrated by the flow chart in FIG. 6c.

Once this threshold optimization is completed, the initialization of the echo detection routine is completed and the program pulses the high voltage supply, starts the digital timer and enables the ramp generator circuit, step 165. Thereafter the echo detector circuit is enabled, 167. Following this step an interrogation is made to determine whether an echo is received or a time out exists, 169. A time out is an absence of an echo. This step 169 is continually repeated until there is a reception or time out.

When there is a reception, the echo detector is disabled, the digital timer is stopped and the ramp generator is stopped and held at its current level, step 171. Thereafter the digital time is stored and the timer lowest significant bit polarity i measured, step 173.

Thereafter, a measurement of the relevant ramp level dependent on the timer lowest significant bit polarity is made, 175. Next, analog time is computed 177, and thereafter, analog time is added to digital time 179. This summation value is stored as time of flight 181 and the program routine is exited thereafter.

Figures 1, 6B:
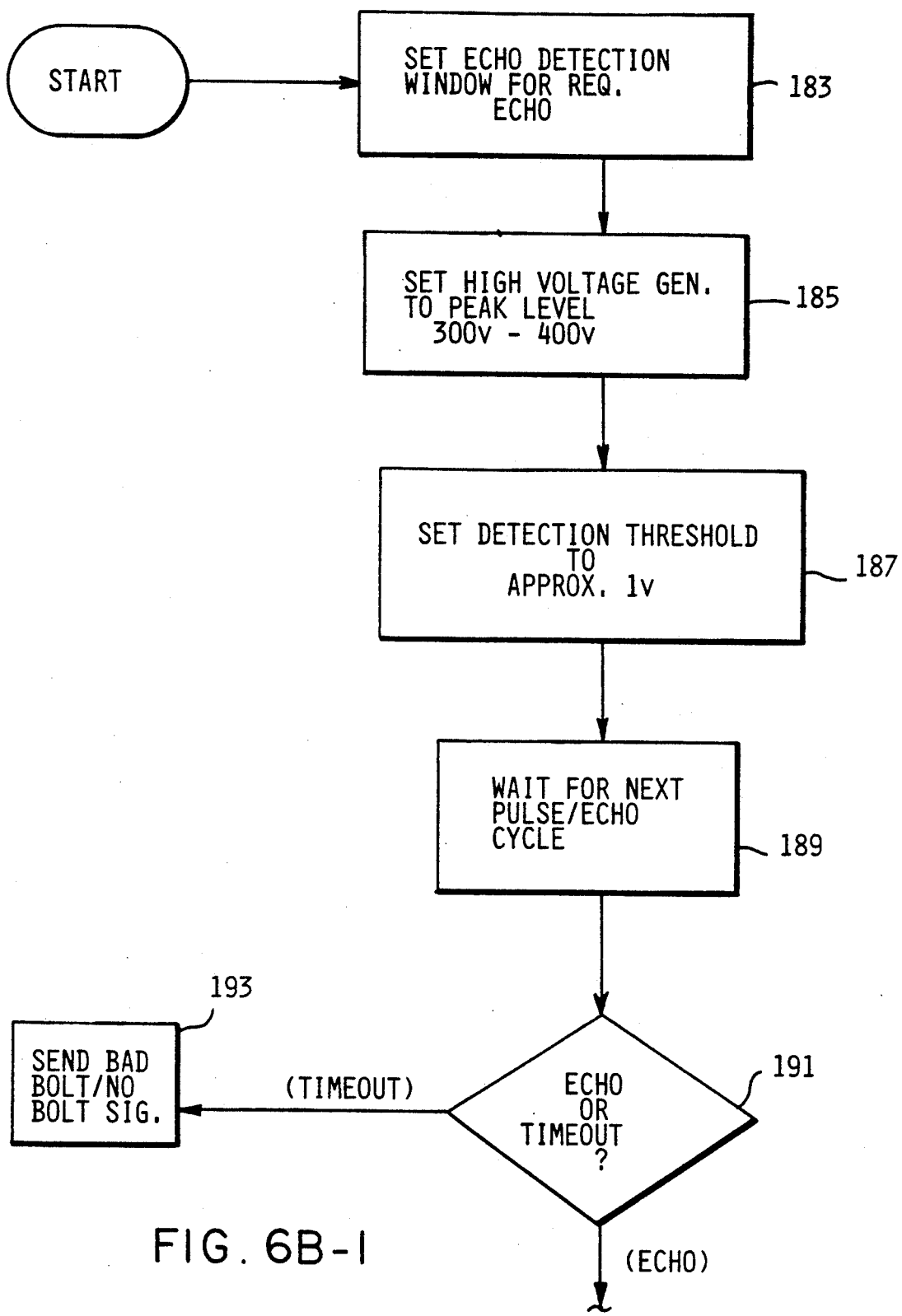
Figures 2, 6B:
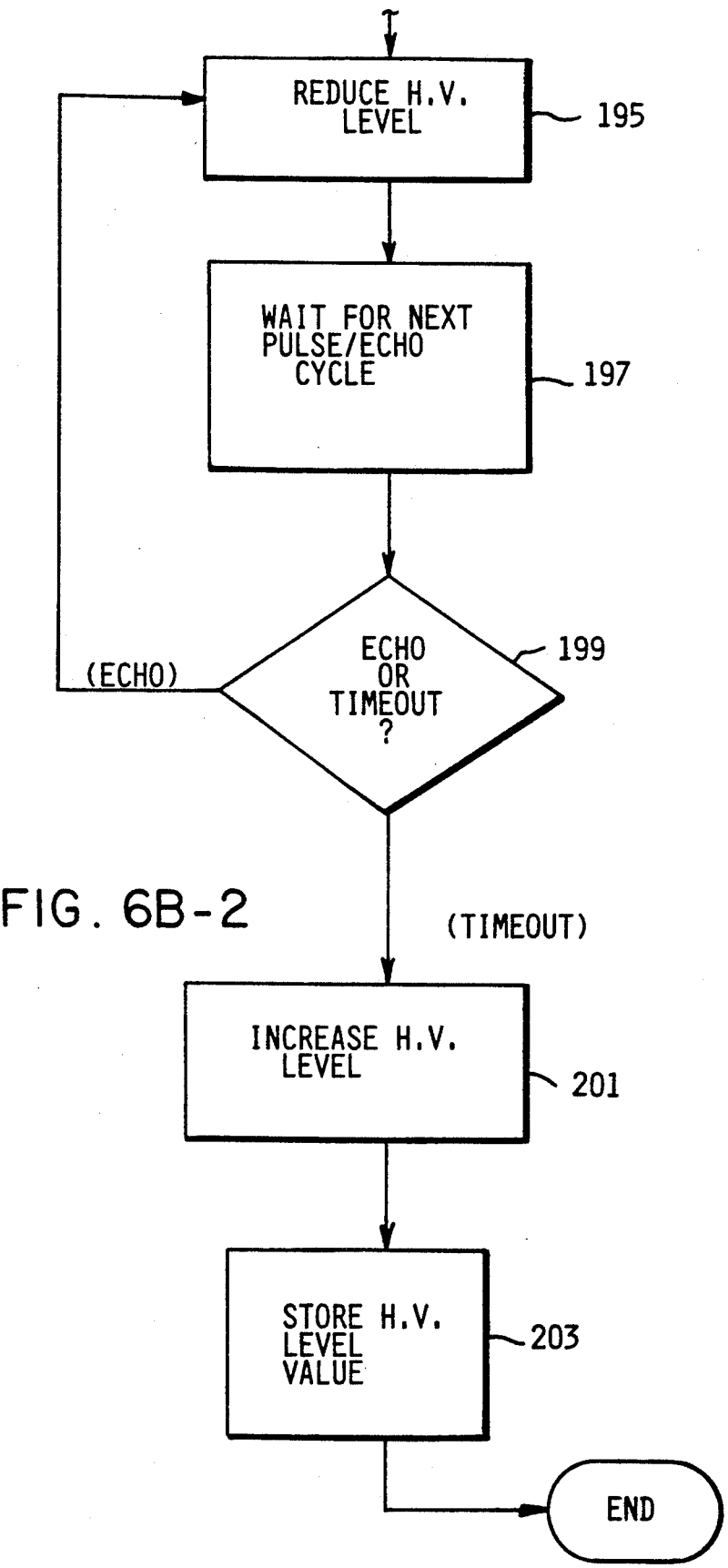

The pulse level optimization software program is illustrated in the flow chart shown as FIG. 6b. When the program is started, the first step is to set the echo detection window for a required echo 183. Next, the high voltage generator is set to its peak level 185. The peak level of this high voltage generator is typically between 300 and 400 volts d.c.

Following this step 185, the detection threshold for the echo detector is set to approximately 1 volt, step 187. After this, the program waits for the next pulse echo cycle 189.

An interrogation is made for a valid detection of an echo or a time out 191. If a time out is received a signal indicating a bad bolt or no bolt signal, i.e. bad transducer or bad transducer connections, is sent to the operator via the RS422 interface port 11, FIG. 1, step 193.

If an echo is received in step 191, the high voltage level for the generator is reduced, step 195. Then, the program waits for the next pulse echo cycle, step 197. With this next pulse echo cycle, the program looks for a valid echo detection or a time out 199. If an echo is received, the program loops back to reducing the high voltage level, step 195. This loop continues until a time out is received in step 199.

When a time out is received as a function of interrogation step 199, the high voltage level is incrementally increased, step 201, and that new level is stored as the optimum high voltage level value, step 203. Thereafter, the routine ends.

Figures 1, 6C:
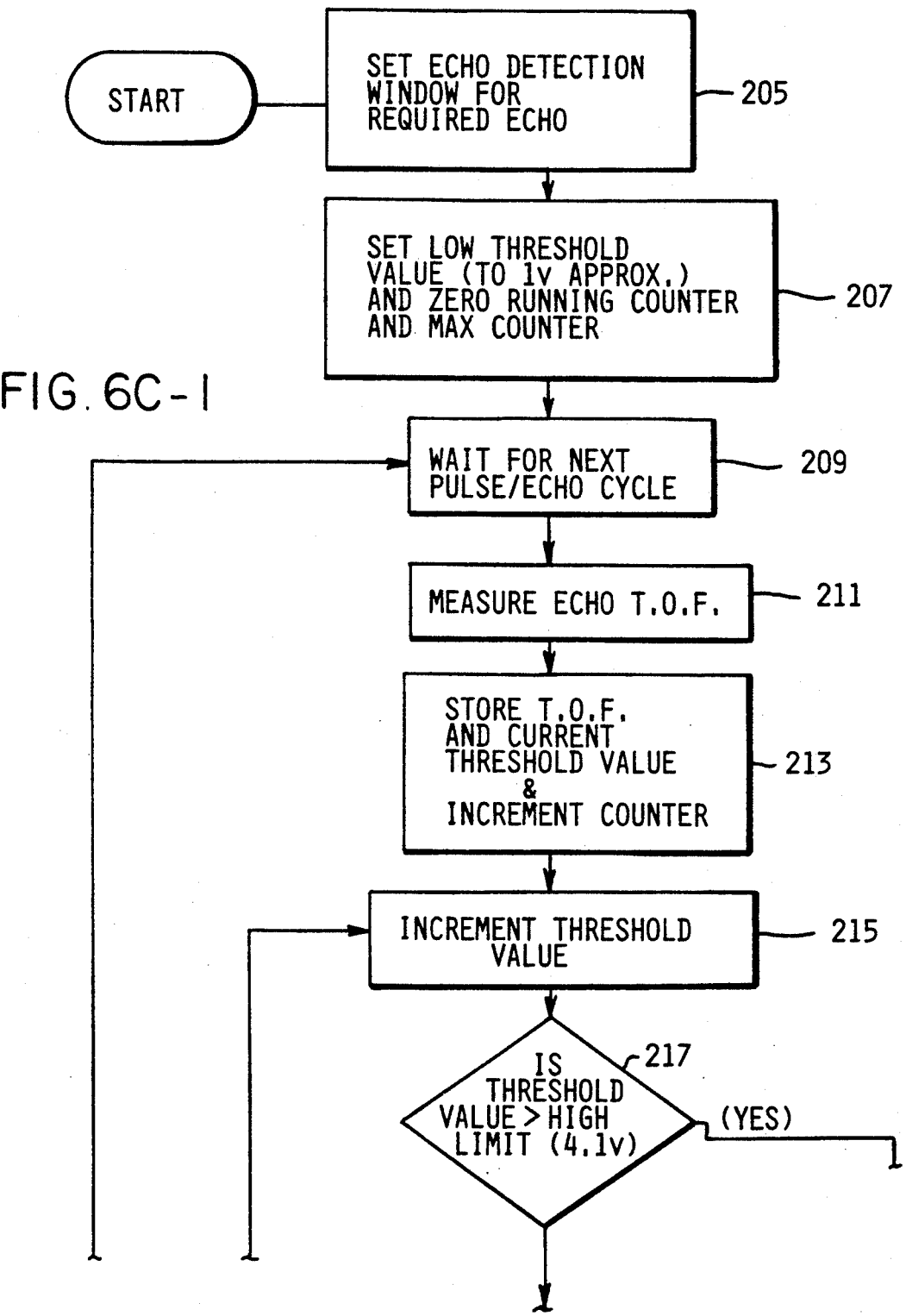
Figures 2, 6C:
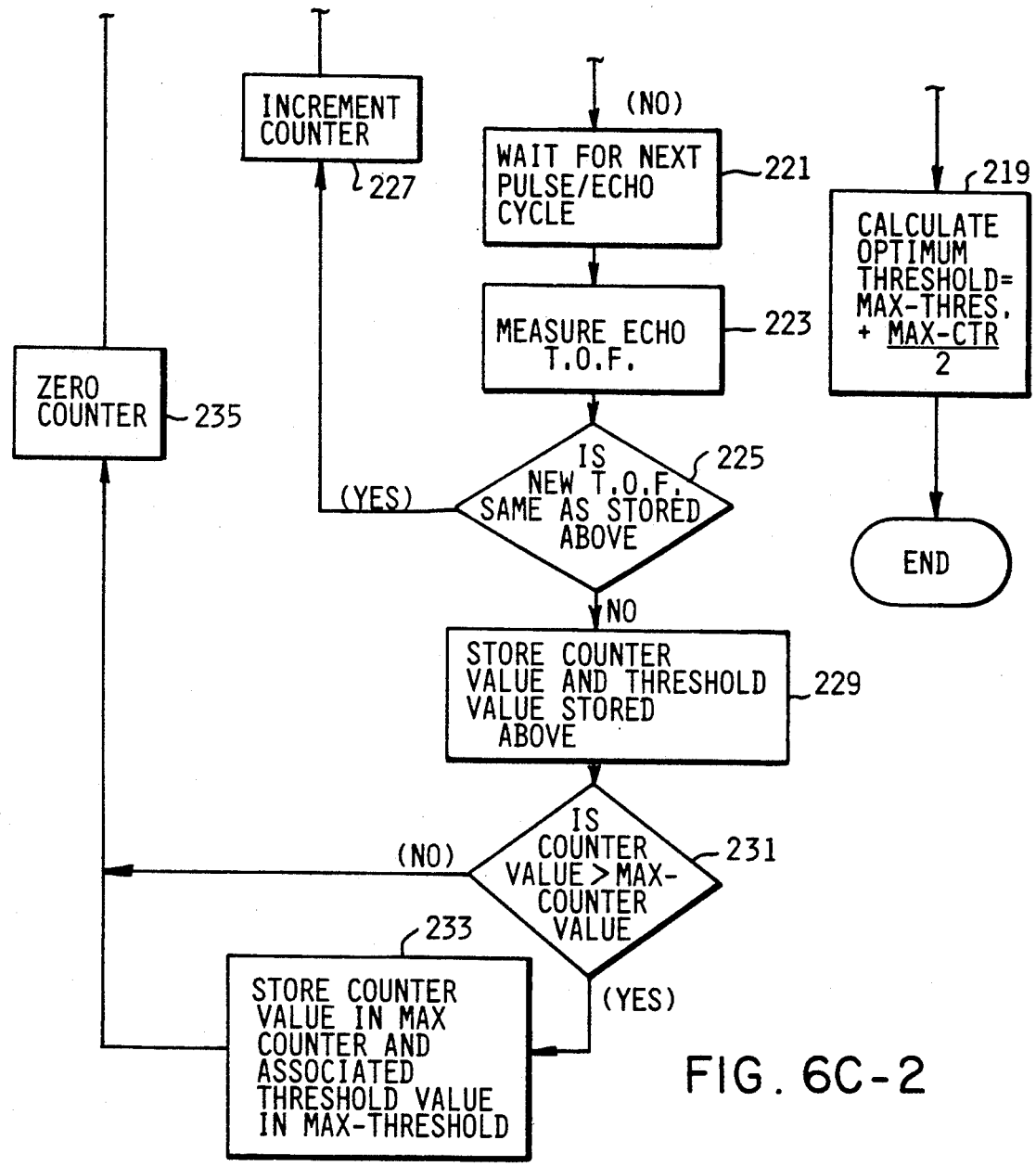

A threshold optimization routine, implemented in program software, is illustrated in FIG. 6c as a flow chart. Here, once the routine has started an echo detection window for the required echo is set, step 205. Then a low threshold value approximately 1 volt and a running counter and max. counter value are set to 0, step 207. Following that step 207, the program waits for the next pulse/echo cycle, step 209.

Upon the next pulse/echo cycle the routine measures echo time of flight step 211, and then stores time of flight and current threshold value and increments the running counter, step 213. Following this step 213, the threshold value is incremented, step 215.

Next the routine inquires whether the threshold value is greater than the high limit, typically 4.1 volts, step 217. If the threshold value is above the high limit value, then a calculation of optimum threshold equal to the MAX_THRES register value plus the MAX_COUNT register value, this second quantity being divided by 2, is calculated, step 219. Following this calculation, the routine exits.

However, if the threshold value does not exceed the high limit in step 217, the program continues to wait for the next pulse/echo cycle, step 221. Upon the next pulse/echo cycle, the routine measures the time of flight of that echo, step 223. Once this time of flight is calculated, it is compared in step 225 with the previous time of flight value stored. If the new time of flight calculated in step 223 does in fact compare with the previous stored time of flight value in step 225, then the counter is incremented, step 227 and the routine thereafter loops back to increment the threshold value by repeating step 215.

If the new time of flight is different from the previously stored time of flight as determined by step 225, then the running counter value and threshold value previously stored are now stored in the microcontroller circuit, step 229. Next, the running counter value is interrogated to determine whether it is greater than the max. counter value, step 231. If this is so, then the counter value in the max. counter and the associated threshold value in the max. threshold register are stored, step 233. Following this step 233, or if the counter value does not exceed the max counter value, the routine operates to zero the running counter step 235 and to loop back into the routine to wait for the next pulse/echo cycle at step 209.

Figures 1, 6D:
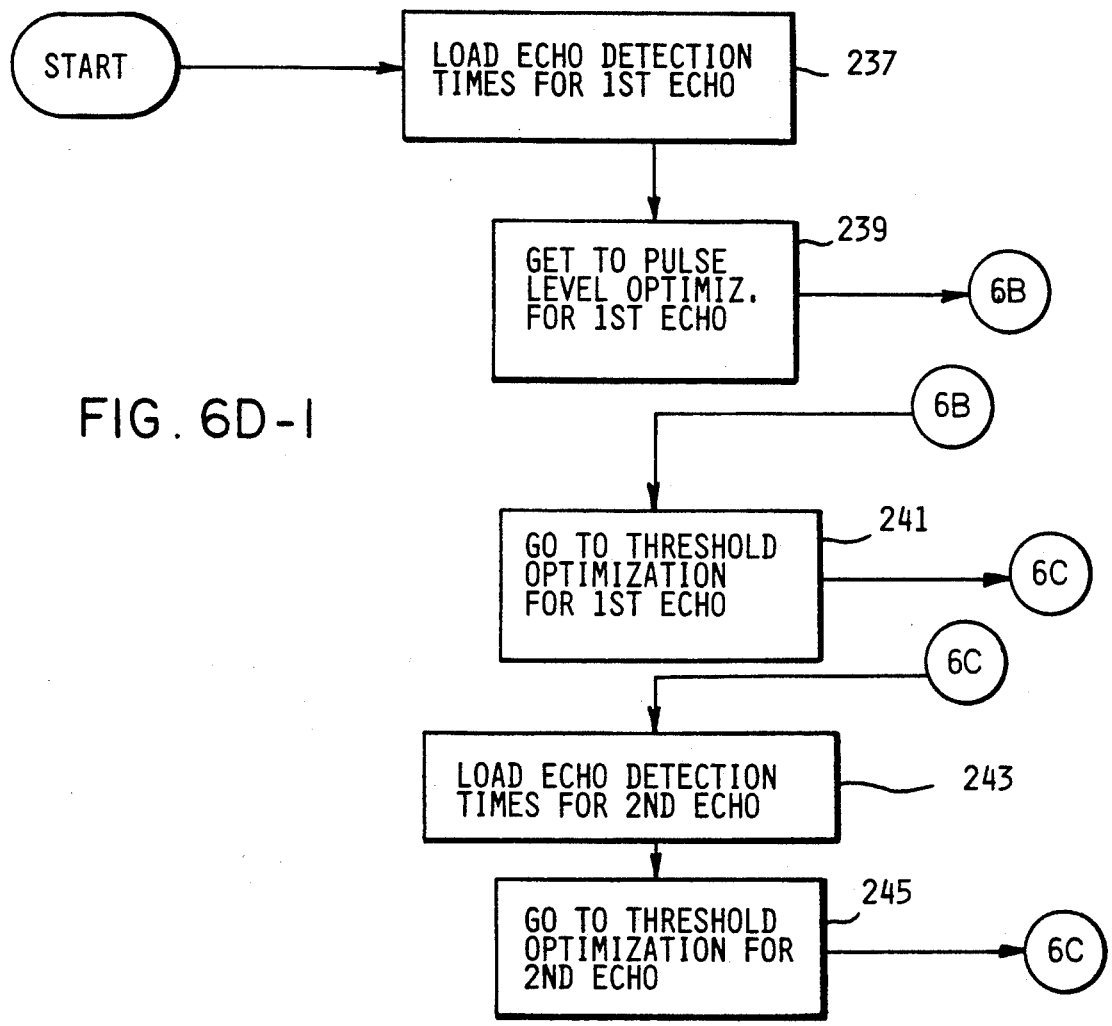
Figures 2, 6D:
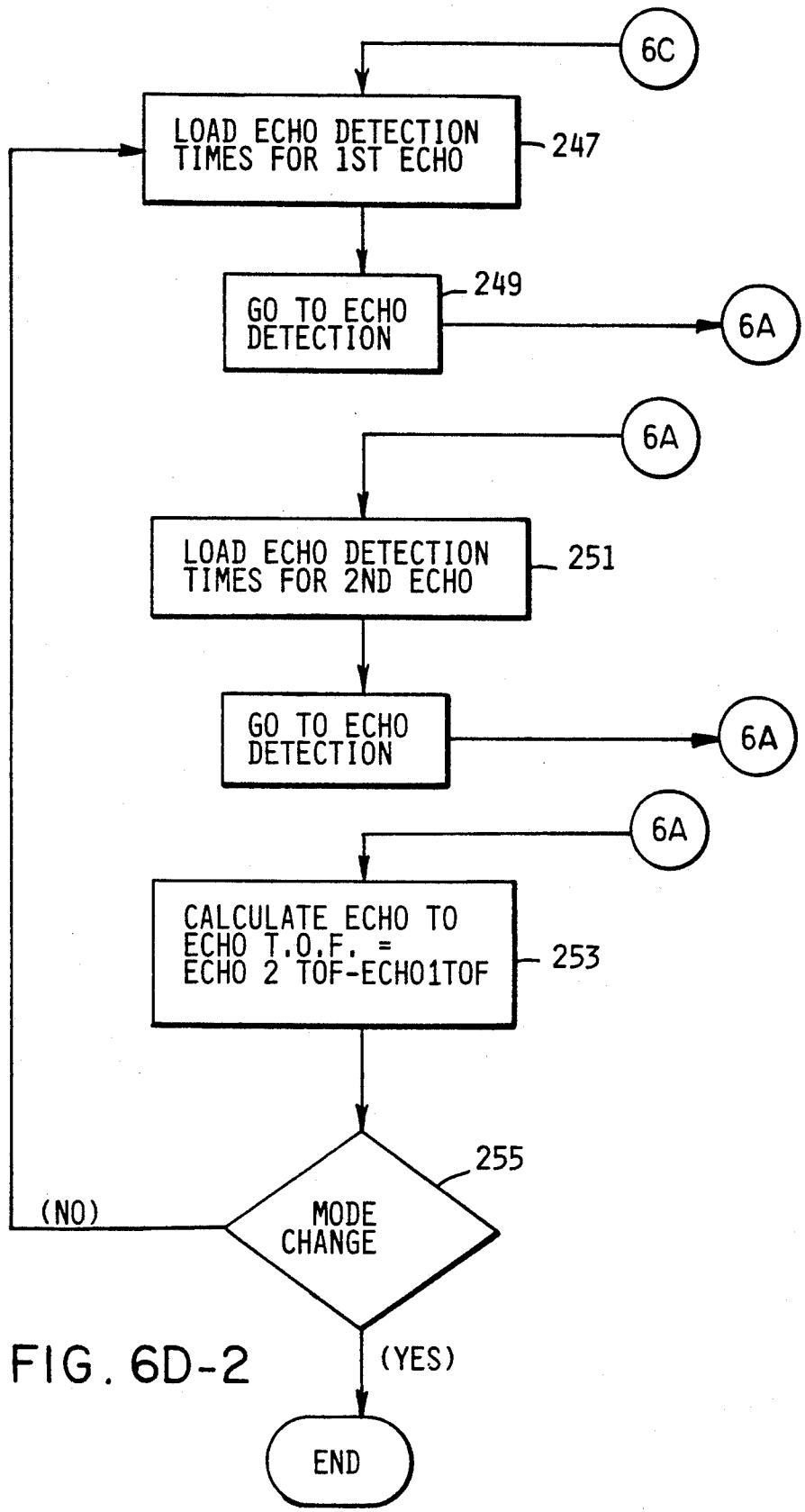
Figures 2, 6E:
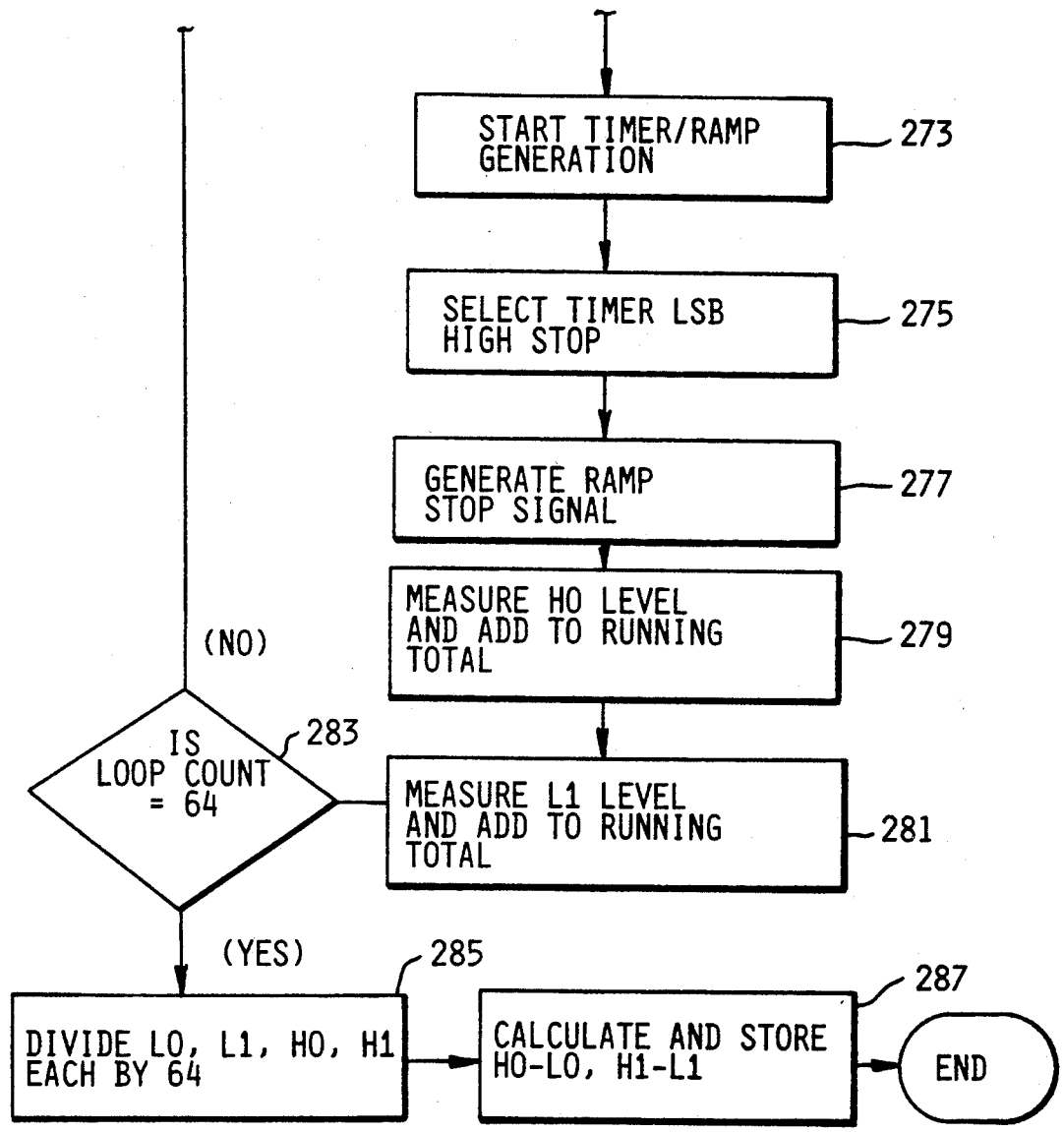

Echo to echo detection, as illustrated in FIG. 3, is conducted by program software illustrated by the flow chart shown in FIG. 6d. Once this routine starts, echo detection times for the first echo are loaded, step 237. Then the routine directs itself to pulse level optimization for this first echo and exits to the routine of FIG. 6b, step 239. Following the performance of this other routine, the program then directs itself to threshold optimization for the first echo, step 241, and exits to the routine illustrated in FIG. 6c. After the operation of this program routine, FIG. 6c the echo to echo detection routine continues with the loading of detection times for a second echo, step 243.

Thereafter, the routine directs itself to call the threshold optimization routine of FIG. 6c, step 245.

Once this threshold optimization routine is performed for the second echo, this routine again loads echo detection times for the first echo, step 247.

Having done this step 247 the routine directs itself to the echo detection routine FIG. 6a, step 249. After the echo detection routine is completed, this routine continues and loads echo detection times for a second time for the second echo, step 251. Then, again, the routine goes to echo detection for this second echo, this being the routine of FIG. 6a. Having completed this, this routine then calculates echo to echo time of flight which equals the time of flight of the second echo minus the time of flight of the first echo, step 253. Having done this step 253, interrogation is made as to whether a repeat is required, step 255. The program loops back to step 247 until otherwise directed.

Ramp calibration is carried out by a program routine illustrated by the flow chart of FIG. 6e. When this routine is called, a loop counter is set to the number 64 and the L0, H0, L1 and H1 registers are set to 0, step 257. Following this step 257, the loop counter count is set to the present count plus 1, step 259. Further, as part of this step 259, the H1 value and the L0 value are selected for measurement.

Following this step, the timer and ramp generation operations are started 261. Then the timer lowest significant bit (LSB) low stop is selected, step 263. Thereafter, a ramp stop signal is generated 265.

Next, an H1 level is measured and added to the running total in the H1 register, step 267. Following this, the L0 level is measured and added to its running total, 269. Then, the timer is cleared and the H0 value and the L1 value is selected for measurement, step 271. With these values, the timer and ramp generation is again started 273. Thereafter, the timer lowest significant bit (LSB) high stop is selected 275.

After this step 275, a ramp stop signal is again generated 277. Thereafter a H0 level is selected and added to its running total 279. Following this, the L1 level is measured and added to its running total, 281.

Following this last step 281, the program interrogates if loop count is equal to 64, step 283. If it is not equal to 64 then the program loops back to step 259 wherein the loop count is set to the present count plus 1 and the remaining processing steps are repeated. If the loop count is equal to 64, then the program divides the L0, L1, H0 and H1 values each by 64, step 285 and thereafter calculates and stores the following values: H0 minus L0 and H1 minus L1, step 287. After this calculation is complete the routine is exited.

Figure 6F:
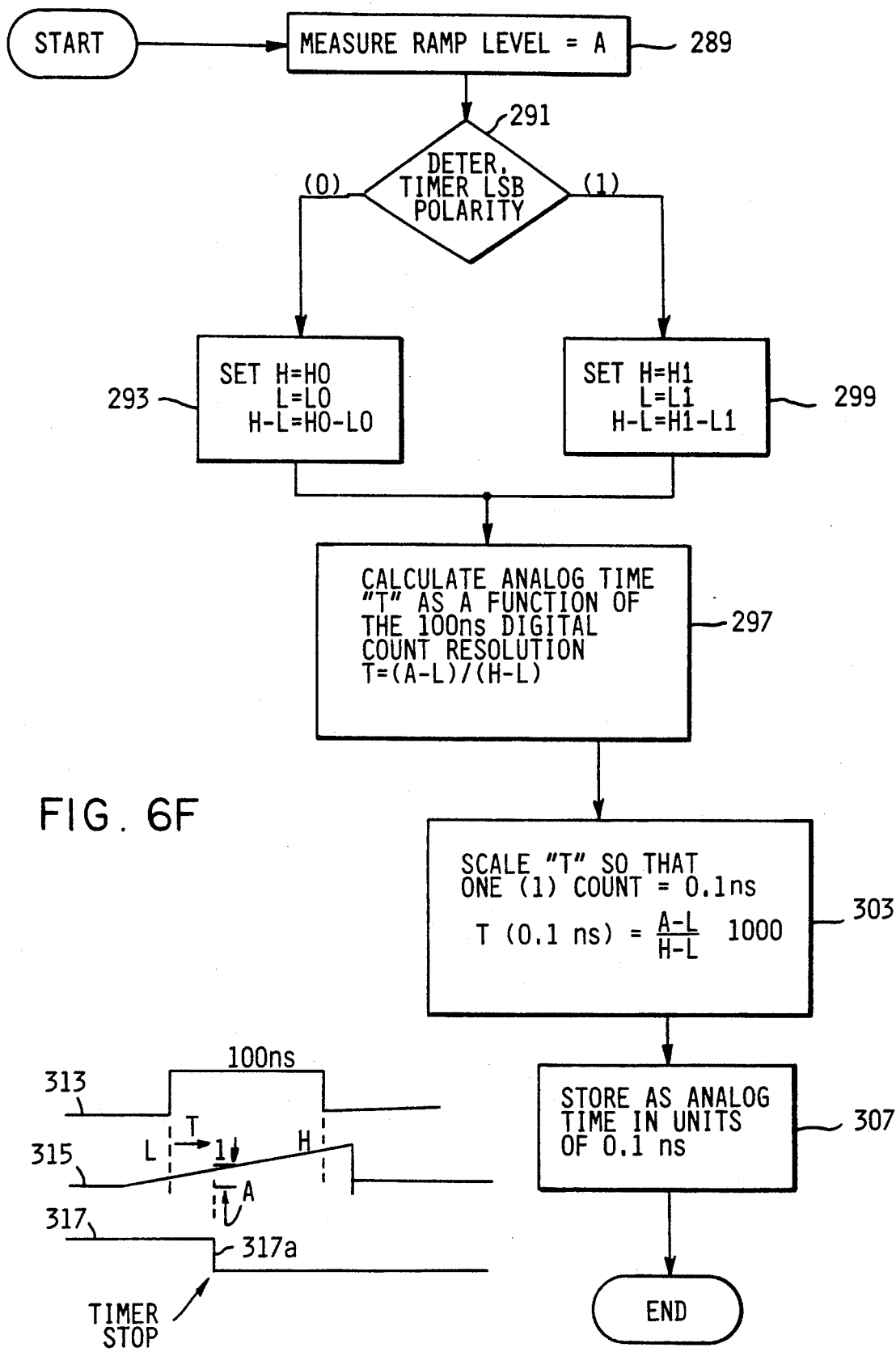

Analog interpolation of ramp level is carried out by a software routine illustrated by the flow chart of FIG. 6f. When this routine is called, the ramp level is measured and set equal to A, step 289. Then the timer lowest significant bit (LSB) polarity is determined 291. If the polarity is "0" (a low), the H register is set equal to H0, L register is set equal to L0 and the value H minus L is calculated equal to H0 minus L0, step 293.

In step 291, if the timer lowest significant bit (LSB) polarity is a "1" (high), the H register is set equal to H1, the L register is set equal to L1, and H minus L is calculated equal to H1 minus L1, step 299.

We now calculate the analog time, "T", according to the formula: T=A−L/H−L, step 297. This is then scaled so that one (1) count is equal to 0.1 nanoseconds, step 303.

Also shown in FIG. 6f is the 10 MHz clock pulse 313 having a pulse width of 100 ns, the ramp 315 and the timer stop signal 317. The timer stop signal 317 is represented by the falling edge 317a which occurs according to the equation values recited above.

Figures 1, 6G:
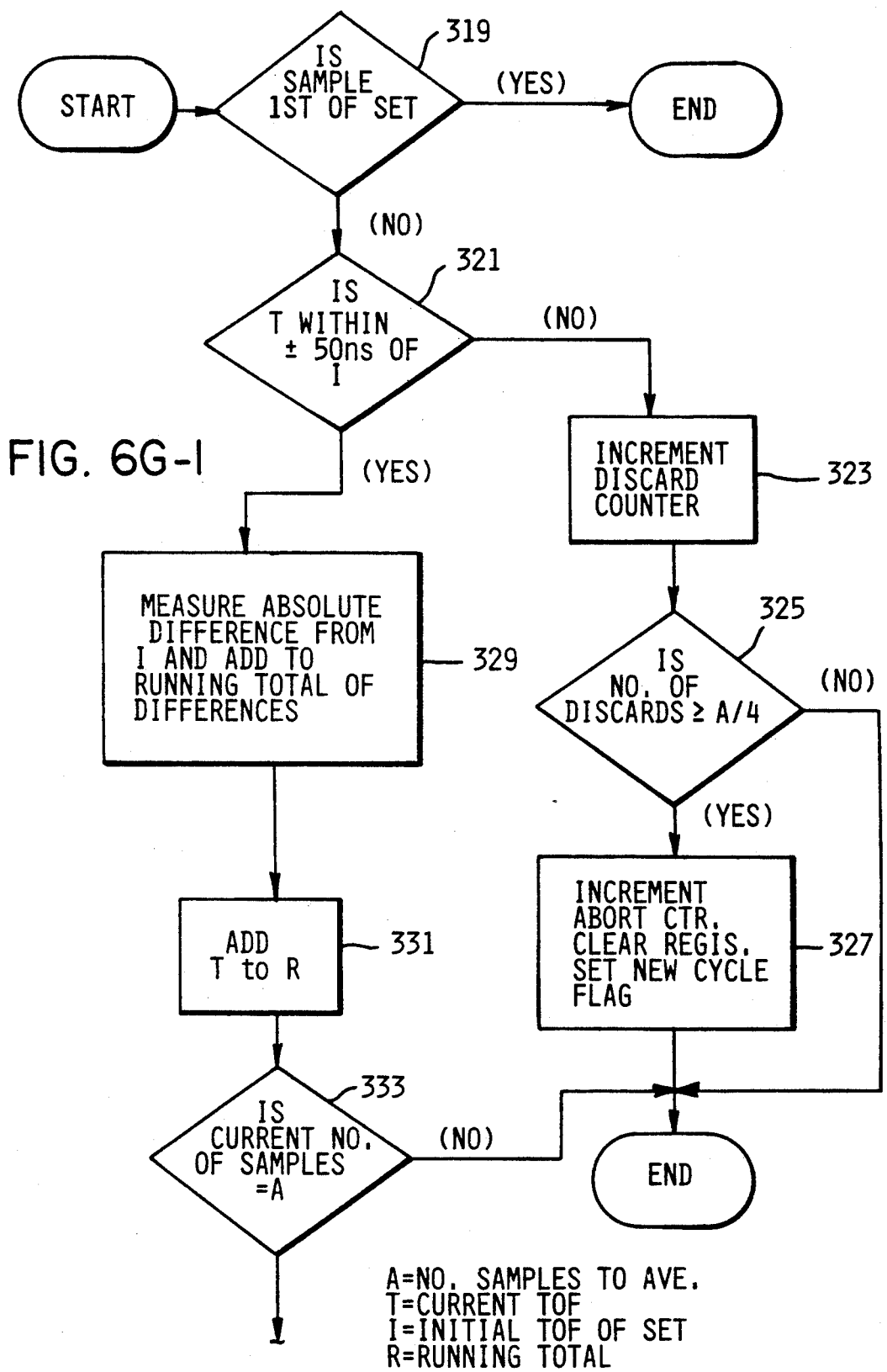
Figures 2, 6G:
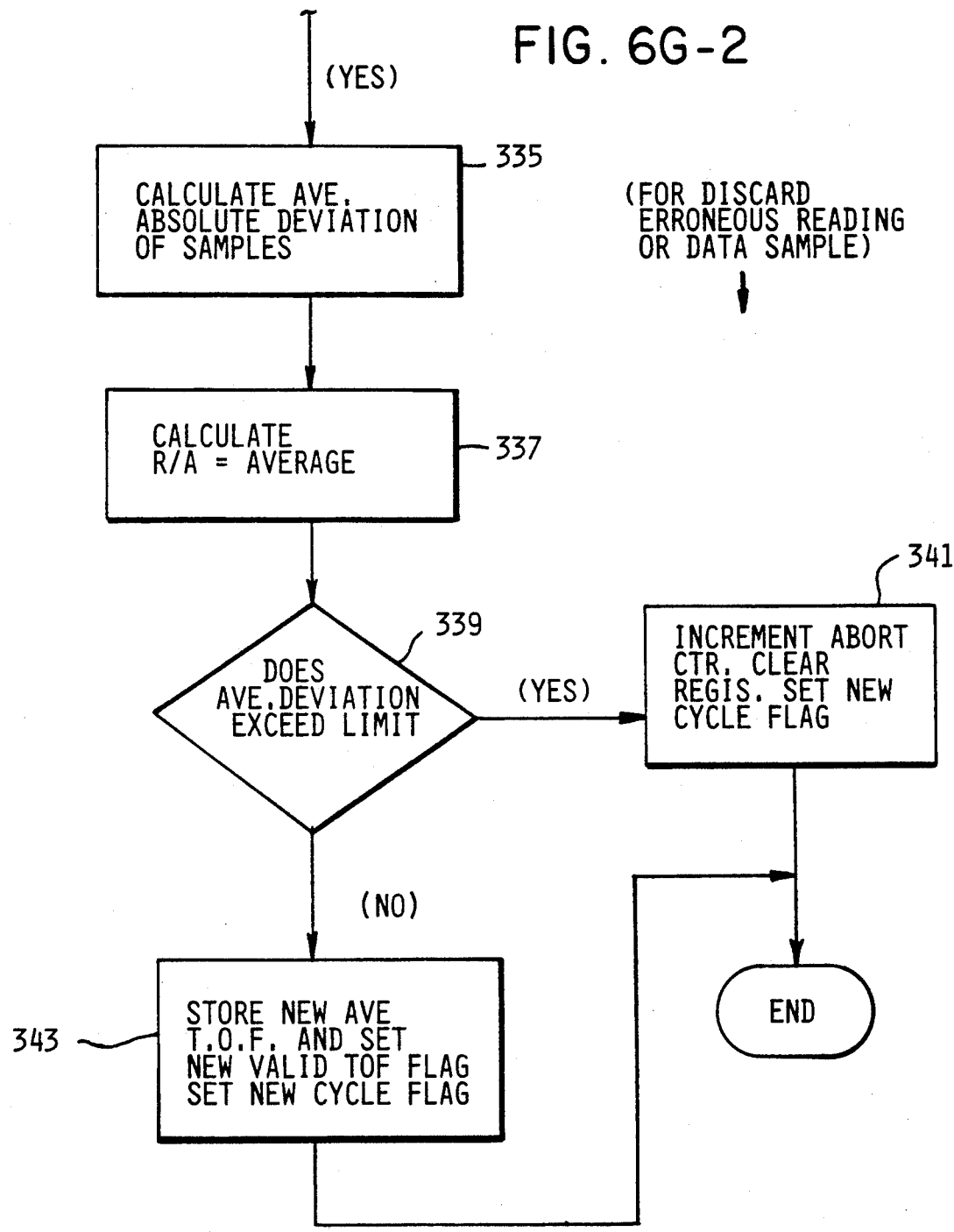

The software resident in the invention also performs digital averaging and filtering according to a program routine illustrated by the flow chart of FIG. 6g. Here the value "A" equals the number of samples to average; the value "T" equals the current time of flight (TOF) the value "I" equals the initial TOF of the "A" samples; and the value "R" is the running total of values.

Once this routine is initiated, its first step 319 is to determine if a sample value read is a first of a set. If this sample is the first of a set then the routine ends. If it is not the first of a set then an interrogation is made to determine if T is within plus or minus 50 ns of I, step 321. If it is not, a discard counter is incremented 323 and then an interrogation, step 325, is made to determine if the number of discards is equal to or greater than A divided by 4.

If this number is not greater than A divided by 4 then the routine ends. If it is greater than 4, an abort counter is incremented, other registers are cleared and a new cycle flag is set, step 327. After step 327 is performed the routine ends.

Referring back to step 321, if it is determined that T is indeed within plus or minus 50 ns of I, then the absolute difference from I is measured and added to the running total of differences, step 329. Following this step of 329, the value T is added to R, step 331. Then, an interrogation is made, step 333, to determine if the current number of samples equals A. If it does not, then the routine ends. If it does, then the average absolute deviation of samples is calculated 335. After this calculation step 335, the value R divided by A equal to an average time of flight is calculated, step 337.

Step 337 provides an average value for readings of time of flight. Following this step 337, an interrogation of the value of the average deviation is made to determine if it exceeds a predetermined limit, step 339. If the average deviation exceeds the limit allowable, then the abort counter is incremented and the registers are cleared and a new cycle flag is set 341. Following this step 341 the program exits the routine.

If in interrogation step 339 the average deviation calculated does not exceed the limit, then the new average time of flight is stored and a new valid time of flight flag is set as well as a new cycle flag being set, step 343. Thereafter, the program exits the routine.

Software code for the program of the flow charts shown in FIG. 2 and in FIGS. 6A–6G can be seen in Table 1.

The circuitry shown in FIG. 1 can be further implemented as shown in FIGS. 7A–7D. Referring to FIG. 7A, the microcontroller circuit 13 of FIG. 1 including its CPU 15 and attendant peripheral components 17, 21, 23, 27, 29, 31 and 33 can be implemented on board the Intel Corporation model 87C196 LSI (large scale integration) chip 345. A reset circuit 347, principally comprising a switch 349 and a pair of serially connected invertor amplifiers 351, 353 is connected into the reset pin of the chip 345.

An RS422 serial interface module 355 is connected between an RS422 interface bus 357 and appropriate pins of the chip 345. It should be stated that the chip 345 is connected according to the manual supplied by the manufacturer for the functions desired.

Figures 1, 7C:
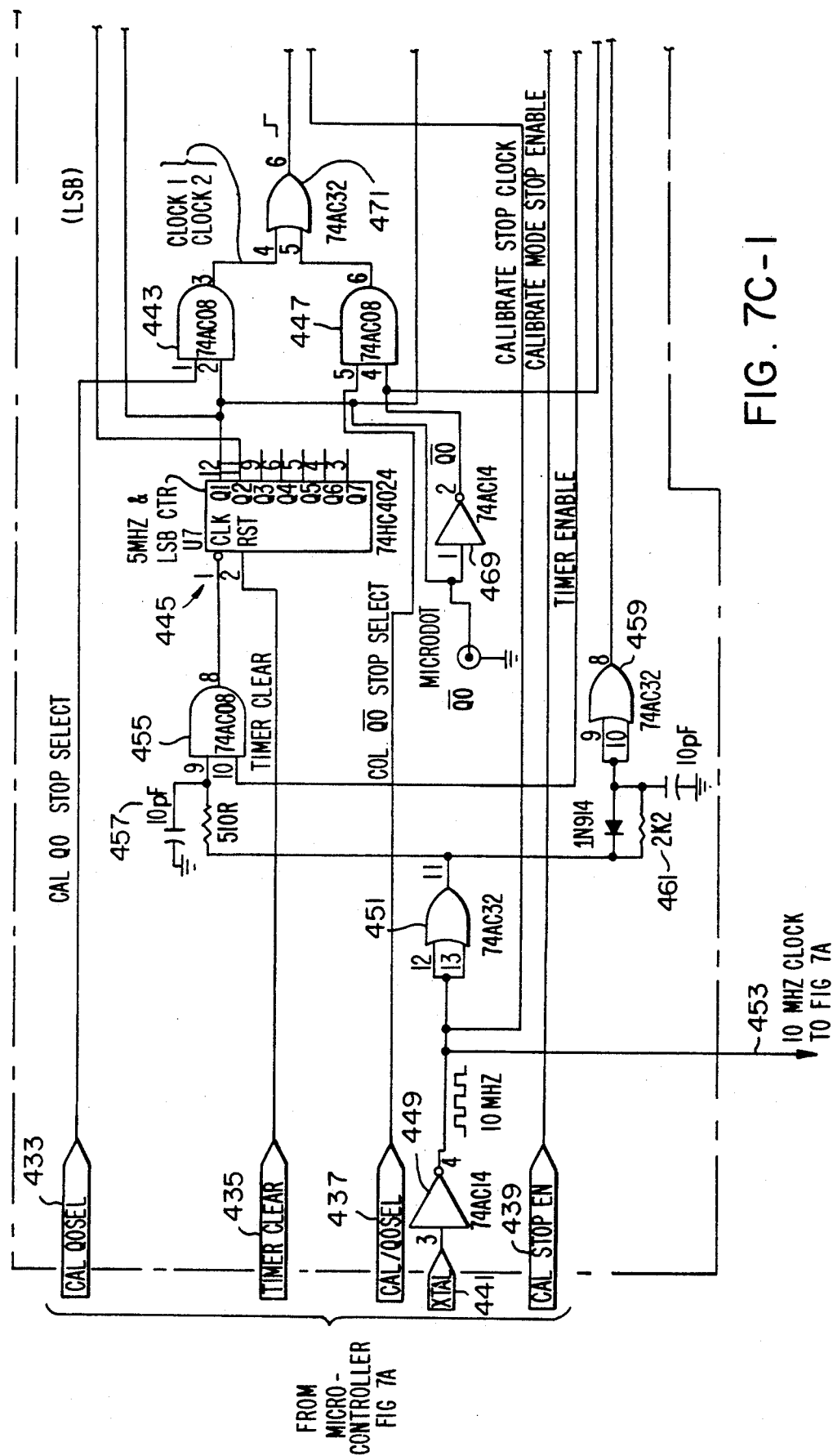
Figures 2, 7C:
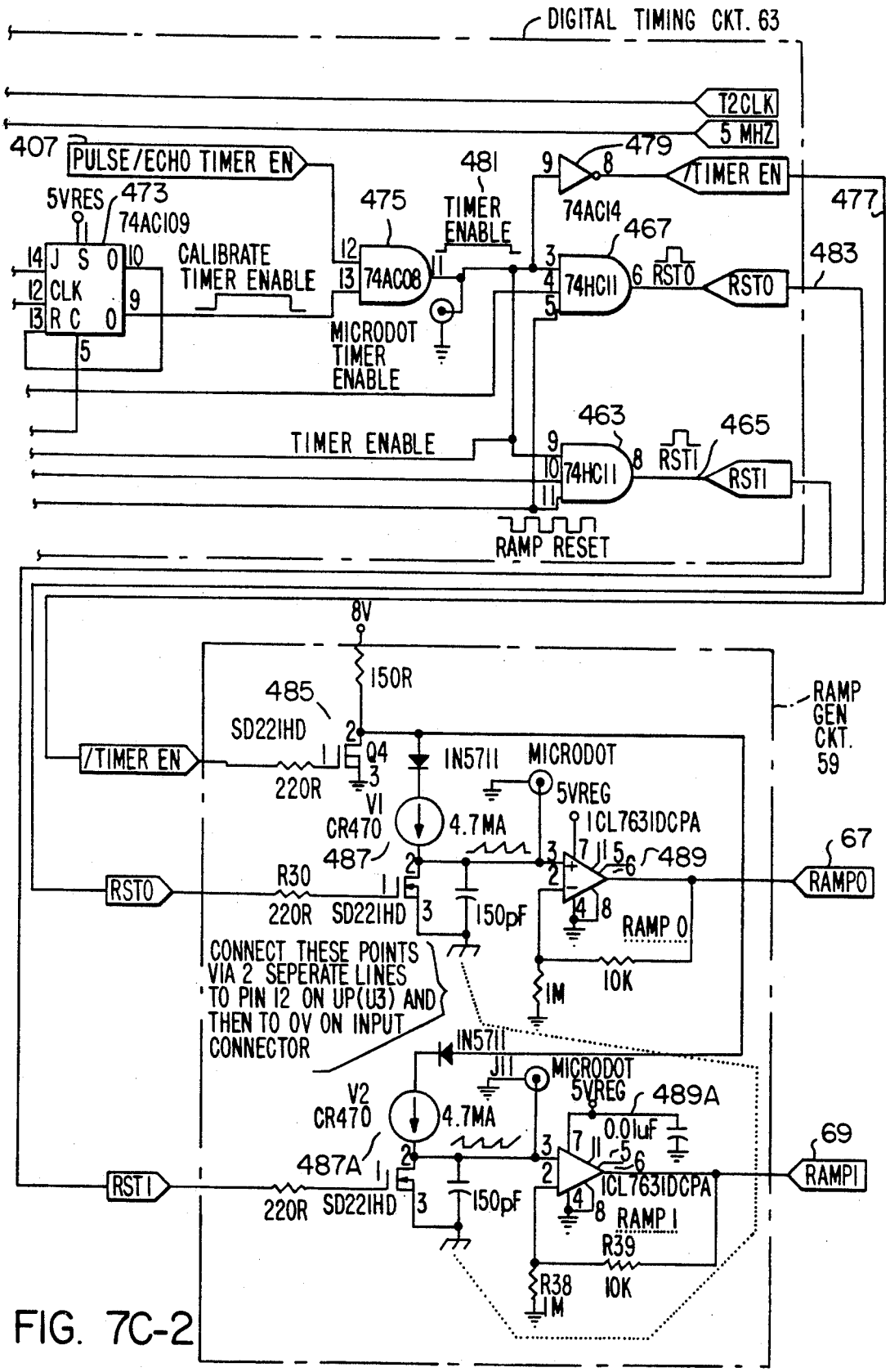
Figures 1, 7D:
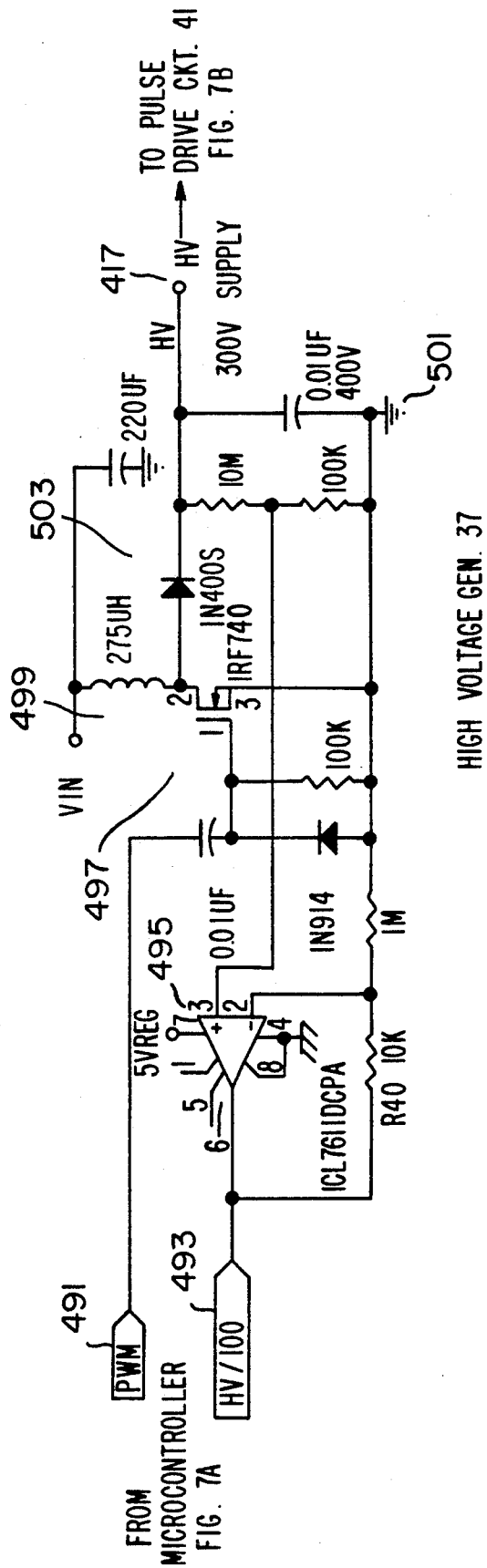
Figures 2, 7D:
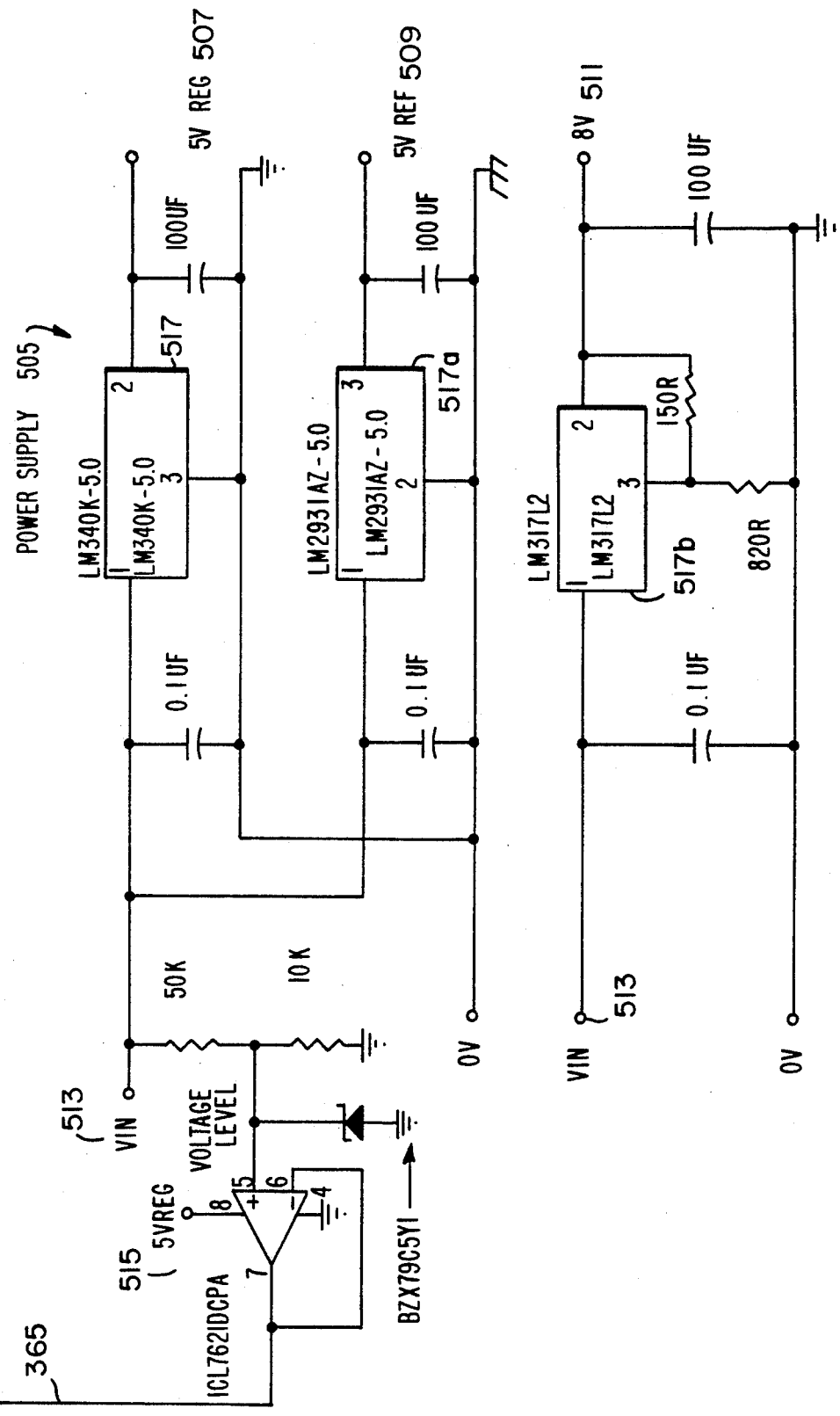

The chip 345 includes a timer clear connection 359 to the circuitry of FIG. 7C, a pulse width modulation connection 361 and a high voltage signal circuit connection 363 to the high voltage generator circuit of FIG. 7D. Further connections from the chip 345 include a power supply connection 365 to the circuitry of FIG. 7D and an echo detection threshold byte connection 367 to the echo detection circuit shown in FIG. 7B.

A pulse trigger signal 369 from the chip 345 is passed on to the pulse drive circuit of FIG. 7B after passing through an invertor amplifier 371. A plurality of signals including timer start echo detection and calibration signals are connected via a bus 373 from the chip 345 to the digital timer circuitry shown in FIG. 7C.

As seen from figure 7A, not all of the digital I/O terminals of chip 345 are utilized. A portion of these terminals are connected to a resister bank 375 and to a digital counter circuit 377. This digital counter circuit 377 has its overflow bit "anded" with an echo detection signal from the chip 345 in an AND gate 379. The output 381 from AND gate 379 is sent to the echo detection enable circuit of FIG. 7B.

FIG. 7B shows an implementation for the echo detection circuit 53 of FIG. 1, the pulse drive circuit 41 of FIG. 1 and the tuned pulse amplifier 51 of FIG. 1. The output 381 from FIG. 7A is an echo detect enable signal which is input to a JK-type flip-flop 383. The bus circuit connection 367, comprising the echo detection threshold byte, is input into a digital to analog convertor circuit 385. The output from this convertor circuitry 385 provides a threshold signal input to a first comparator circuit 387. This first comparator circuit 387 is matched with a second or referenced comparator circuit 389 which has its input as the echo pulse detected from the ultrasonic transducer 47 and then amplified through the tuned amplifier 51.

The outputs from the comparators 387, 389 are connected through two parallel circuits each comprising various connections of these to input NAND gates 391, 393, AND gate 395, NAND gates 391a, 393a, AND gate 395a, respectively. These two parallel NAND-/AND gate paths are cross-connected on a corresponding input of each NAND/AND gate as shown in FIG. 7B.

Each circuit leg output AND gate 395, 395a has one of its inputs connected directly from its own respective comparator 387 output through a RC filter 397, 397a. The output from the AND gate 395 is the positive threshold trigger signal 399, while the output from the AND gate 395a is the negative threshold trigger signal 399a. These two signals 399, 399a are "or'ed" through OR gate 401 to clock the JK flip-flop 383.

JK flip-flop 383 is reset by the timer start signal 403 which is one of the bits in the signal bus 373 from chip 345 of FIG. 7A. The inverse output terminal of the JK flip-flop 383 is connected to an AND gate 405. This AND gate 405 has its second input connected to receive a timer start signal 403. The output from this AND gate 405 is the pulse/echo timer enable signal 407 which is connected back to the chip 345 of FIG. 7A. Pulse/echo timer enable 407 is also connected to an input of AND gate 475 of the digital timing circuit as shown in FIG. 7C.

Pulse drive circuit 41 shown on FIG. 7B receives the trigger pulse signal 369 from FIG. 7A. This pulse signal 369 is A.C. coupled to a pulse drive circuit 413 through a RC-diode circuit 409. The RC-diode circuit 409 output is input into a pulse drive circuit 413. The output from the pulse drive circuit 413 triggers a field effect transistor switching circuit 415. This field effect transistor switching circuit 415 is powered from the high voltage supply 417 provided as a output from the high voltage generator 37 of FIG. 1. This provides a high voltage spike which becomes the source/drive pulse 419 after it is shaped through another filter and diode clamping circuit 421. This source/drive pulse 419 is sent to the ultrasonic transducer 47.

The echo from the ultrasonic transducer circuit 47 is input to the tuned amplifier circuit 51 implemented as shown in FIG. 7B. The echo 423 is first passed through an RC-diode clamping circuit 425; and then passed through a tuned amplifier circuit 427 which is tuned according to standard specifications to the median resident frequency of the reflected waves (echoes) for the ultrasonic transducer 47 connected the bolt 49 under examination. The output from this tuned amplifier 427 is passed through a second amplifier circuit 429 to provide an output signal 431 which is a cleaned up version of the original echo signal 423 without the attendant noise and clutter on that original echo signal 423. The output echo signal 431 is connected to the echo detection circuit 53 inputs to its paired comparators 387, 389, FIG. 7B.

A calibration Q0 stop select signal 433, FIG. 7C, a timer clear signal 435, a calibration "not" Q0 stop select signal 437, a calibration mode stop enable signal 439 and an external clock signal 441 are all received by the digital timing circuit 63 of FIG. 7C from the bus 373 shown on FIG. 7A.

The input signal 433 is connected to an AND gate 443 while the input signal for the timer clear 435 is connected to a 5 MHz and lowest significant bit (LSB) counter 445. The input signal 437 for calibrate inverse stop select is connected to another AND gate 447. The external clock signal 441 is passed through an inverter amplifier 449 to both inputs of an OR circuit 451. The output of amplifier 449 becomes a 10 MHz clock signal 453 to the counter 337 of FIG. 7A.

The clock input of the counter 445, FIG. 7C, is connected from the output of the OR gate 451 through an AND gate 455. AND gate 455 has an RC delay circuit 457 on its input. The output of OR gate 451 is also input to both inputs to another OR gate 459 with an intermediate delay circuit 461 being in place on the inputs of OR gate 459. The output of OR gate 459 becomes a ramp reset clock pulse signal which is sent to two three input AND gates 463 and 467. The outputs of AND gates 463 and 467 are the reset pulses 465 and 483 which are sent on to the ramp generator circuit 59.

AND gate 447 also receives an input from a 5 MHz output of the 5 MHz and LSB counter 445. This input is sent to the AND gate 443 directly and to another AND gate 467 directly and to the AND gate 447 through an inverting amplifier 469.

The output from AND gates 443 and 447 are the first and second clock pulses which are or'd through OR gate 471 to the J input of another JK-type flip-flop 473. This JK flip-flop is clocked from the output of the inverter amplifier 449 and is reset from the input signal 439. The inverted output from this flip-flop 473 is input to another AND gate 475. AND gate 475 also receives a pulse echo timer enable signal, 407 of FIG. 7B.

The inverting amplifier 479 has its input connected to the output of the AND gate 475. The signal produced by the inverting amplifier 479 is the inverse timer enable signal 477 which is connected to one input of the ramp generator circuit 59, shown in detail of FIG. 7C. The output from AND gate 467, which is a reset signal 483, is likewise sent to the ramp generator 59. This reset signal 483 is the "0" state reset signal. The "1" state reset signal 465 is also sent on to the ramp generator circuit 59 of FIG. 7C.

Ramp generator circuit 59 as shown in FIG. 7C has two parallel operating legs. The inverse timer enable signal 477 is input into a transistor switching circuit 485, which is then connected to two parallel operating sawtooth generators 487, 487a, one in each leg of the ramp generator circuit 59.

The output from the transistor switching circuit 485 is input into a sawtooth generator circuit 487 of the first ramp generator side and a second sawtooth generator circuit 487a of the second ramp generator leg. The first ramp generator leg 487, 489 provides as an output the "ramp 0" signal 67 shown in FIG. 1, while the second ramp generator leg 487a, 489a provides the "ramp 1" signal 69 shown in FIG. 1. These signals 67, 69 are outputs of the respective operational amplifiers 489, 489a. Each of these operational amplifiers 489, 489a has attendant circuit connections to create the ramp signals 123, 125 shown in FIG. 4 from the sawtooth waves input into each amplifier. The generation of the "ramp 0" signal 67 and the "ramp 1" signal 69 offset to one another is created as a function of the difference in the time occurrence of "0" state reset signal 483 and the "1" state reset signal 465.

The high voltage generator 37 is shown in FIG. 7D. Here a pulse width modulation input signal 491 and a high voltage output divided by a 100 signal 493 are connected to the microcontroller chip 345 of FIG. 7A. Input signal 493 is really a feedback signal from the output of an operational amplifier 495 which is sent back to the microcontroller chip 345 to monitor the state of the high voltage generator 37.

This high voltage generator 37 as shown in FIG. 7D is really a semi-regulated power supply which is pulsed on and off as a function of the presence of the signal 491 fed to a transistor switch circuit 497. The transistor switch circuit 497 is connected to the output of an inductor 499 which transforms the voltage into the desired output voltage 417 sent to the pulse drive circuit 41 of FIG. 7D. In this case, a voltage anywhere between 15 volts d.c. and 400 volts d.c. may be selected by microcontroller 345 of FIG. 7A.

A power supply circuit 505 of reasonably standard design, FIG. 7D, provides a 5 volt regulated voltage 507, a 5 volt reference voltage 509 and an 8 volt reference voltage 51; for use by the rest of the circuitry. The connection 365 from the chip 345 to the power supply 505 is really a sense line for the chip 345 to monitor the level of the voltage in 513, this being the external voltage supplied to the invention. This is done through a scaling amplifier 515. Each leg of the power supply 505 includes its own individual scaling circuit 517, or 517A or 517B to set the voltage 507, 509, 511 output provided.

Functional Operation

The functional operation of the invention takes many factors into consideration. Many different bolt 49/ultrasonic transducer 47 configurations are possible, thereby demanding a wide range of high voltage source pulse level and detector amplifier 51 gain combinations in order to provide consistently valid echo detection throughout a tightening operation. By designing flexibility into the high voltage generator circuitry 37, a fixed gain detection amplifier 51 solution is possible. This tends to reduce the complexity of the amplifier 51 design.

High voltage levels are generated by the pulse width modulation driven step-up switching regulator (generator 37). The microcontroller chip 345 of FIG. 6A internally generates the pulse width modulation signal and sets the correct duty-cycle for a desired high voltage level which is measured by the chip 345 (controller 13, FIG. 1) with its on board A/D converter. Ultrasonic pulses are generated in the bolt 49 by pulsing the transducer 47 with the high voltage level pulses of short duration.

As previously indicated, the program software determines the optimum voltage level for a particular bolt being tightened. The pulse drive circuitry 41 switches on in less than 10 ns; and at the pulsing time the digital timer circuitry 63 is enabled. The timer circuitry 63 in conjunction with the analog timing circuitry provided by ramp generator circuit 59 operates with a resolution of about 200 ps.

This resolution of about 200 ps is the resolution attainable by the timing circuitry in a single time of flight measurement. Because of "averaging", the resolution internal to microcontroller 345 is 100 ps.

Echo signals received from the bolt mounted transducer 47 are filtered and amplified by the tuned amplifier 51 to a level of approximately 3.5 volts, peak to peak.

Because echo waveforms can vary in amplitude and are subject to electrical and ultrasonic noise during tightening, it is preferable to use an echo waveform zero crossover point to generate a stop signal for time measurement rather than a threshold point used in state of the art devices. The present invention uses threshold crossover to "arm" the stop circuitry and a following zero crossover detection point to generate a stop command (signal).

In setting the threshold level, the circuitry seeks the location on the echo waveform which is most immune to noise and pulse amplitude variations. This point is, typically, in the middle (mid-point) of the largest "face" (lobe) of an echo waveform. This can generally be a level established as the mid-point value between the peak value of the largest lobe and the peak value of the previous lobe.

The echo detection circuitry 53 will cause an echo returning in a valid time window, which is set by the microcontroller software, to generate a stop signal shown in FIGS. 4 and 5 to the timing circuitry 65 ramp generator circuit 59. The echo return time is processed in the program software by the filtering and averaging routine of FIG. 6G to generate a valid "time of flight" (TOF) representing the current bolt 49 length. This information may be communicated, upon request, through the RS422 serial interface 11. The RS422 interface allows for the exchange of data between the invention and various external devices including a tightening drive unit.

Time of flight (TOF) measurement is determined within the microprocessor chip 15 from the digital count in counter 29, the LSB from digital timing circuit 63, and the analog timing information from ramp generation circuit 59 which create values which are combined to generate TOF as a composite value at "stop". The "stop" signal, therefore, establishes a "freeze" on the current state of information from counter 29, LSB from timing circuit 63, and analog information from ramp generation circuit 59, to determine TOF.

As a timing resolution of 200 ps is required for the invention, a digital counter, such as counter 29, providing this accuracy would demand a clock frequency of 5 GHz. At this frequency it would be necessary to use ECL or GaAs integrated circuits which are extremely power hungry, very expensive and require very careful mounting and layout in order that they work properly. Such an implementation is not a realistic option. Therefore, a technique to provide timing accuracy beyond that available from a straight forward digital count is employed. This requires the circuitry to interpolate the time between digital counts. Two anti-phase ramp signals synchronous with the digital clock 25 is generated. Then the fractional time between clock edges is determined by measuring the height of one of the ramps with an A/D converter as shown in FIGS. 4A and 6F. The resolution of the interpolation is dependent only on the number of bits used in the conversion.

The dual or two phase ramp signals 123, 125, FIG. 4A, are employed so that there is always a valid ramp signal for time measurement. At any instance of time selected, a ramp signal may be chosen from the two signals 123, 125 which is not undergoing reset transition and therefore a valid value is obtainable.

As indicated above, the present invention utilizes four signals, a 10 MHz clock 119, a 5 MHz clock 121 and two anti-phase ramps 123, 125, FIG. 4. By using the two ramp signals 123, 125 a linear portion between edges of the 5 MHz signal 119 is ensured. A digital count is taken from the 5 MHz signal 121 shown in FIG. 4 and the polarity of the 5 MHz signal is used to decide which of the ramp signals 123, 125 is to be used to make an analog measurement. Prior calibration of the ramps, i.e. measurement of the L0, L1, H0 and H1 values allows for an accurate time interpolation calculation to be made.

The software shown by the flow charts of FIGS. 2 and 6A–6G is held in the internal 8K program memory of the microcontroller. This software manages and controls the circuitry 37 associated with high voltage (HV) generation, the HV pulsing 41 and echo detection 53 circuitry and the analog ramp generation circuitry 59. Timers and A/D converters internal to the microcontroller perform time and voltage level measurement functions.

The software is written in MCS-96 assembly language and is shown in Table 1 below.

The high voltage pulsing level from generator circuit 37 is generated from an unregulated 12 volt input supply by a step-up switching regulator circuit. The switching frequency and duty cycle are controlled and set by the microcontroller loaded software.

The microcontroller is operated according to the specifications published by the manufacturer. A pulse width modulation (PWM) output at a designated pin is enabled by setting a designated bit of a special function register according to manufacturers specifications. A PWM frequency of 9.8 or 19.2 KHz can be selected. Similarly the PWM duty cycle is set from 0 to 100% by setting the PWM control bit(s) as stated in the manufacturer's specifications.

By setting the appropriate duty-cycle, a HV level from 15 up to 400 volts d.c. can be set. The actual scaled HV level is measured with the microcontroller's 10-bit A/D converter.

The high speed output (HSO) subsystem of the microcontroller triggers events at specific times with little software overhead. It consists of six output pins which are set/reset at programmed times relative to each other which implement the following events:
a. Pulse the HV supply 37;
b. Start the digital timer (counter) 29;
c. Enable ramp generation circuit 59;
d. Enable echo detection circuit 53;
e. Disable echo detection circuit 53 and initiate analog ramp voltage level measurement from ramp generator circuit 59;
f. Select calibration points on ramps, FIG. 4A; and
g. Initiate measurement of calibration points, FIG. 4A.

A memory map of the 64k address space of the microcontroller is provided by the manufacturer. The 87C196KB chip is an EPROM version. It contains 8k of its own code memory in the section from 2000H to 4000H in the address space. This memory contains the software.

The microcontroller CPU main components are a register file and a Register/Arithmetic Logic Unit (RALU). The RALU does not operate on an accumulator but directly on any of the 256 byte register files located in the address space. Locations 18H to FFH contain 232 bytes of internal data memory which is accessible to the user in bytes, words, or double words. Locations 00H to 17H are the Special Function Registers or SFR's through which all the I/O and peripherals of the microcontroller are controlled. All program variables are contained in the top 232 bytes of the register file.

After performing setup and initialization functions the software program controlling the microcontroller follows a looped path shown in FIG. 2.

In the two loop functions performed by the program, the program loads the correct echo detect start and end times and echo detection threshold values for the next "pulse-echo" sequence. Any high voltage level change requests or optimization requests are handled here. This routine sets the parameter values for the next pulse-echo sequence. The latter subroutine determines if any serial port interrupt servicing is required and provides the service if so.

At the initialization stages, a first microcontroller timer is setup to cause a periodic interrupt of the main program loop mentioned above. During the servicing of this timer interrupt, the primary function of the drive/sense module circuit is implemented, i.e. generation of high voltage pulses and measurement of the time to the return of an echo. This echo is usually the first echo, but it could be the second or third echo.

The hardware associated with high voltage level generation as described above. In software, the high voltage level is controlled in the routine. The actual high voltage level is monitored on a channel of the 8-channel A/D converter within the microcontroller structure. The measured value is compared with a target value contained in a register within the microcontroller. If the actual value is greater than or less then the desired value then the pulse width modulation register is decremented or incremented respectfully to alter the high voltage level in the appropriate direction. The actual level is then remeasured and compared with the target once again and the process is repeated until a level equal to the target level is attained.

The load on the high voltage supply is largely determined by the high voltage pulse rate. Because this main load is pulsed rather than continuous, the change in the high voltage level due to altering the pulse width modulation duty cycle is not truly reflected until a number of pulse-echo sequences later. The actual number of pulse-echo times necessary to wait before making the subsequent high voltage level measurement has been found to be dependent on both the high voltage power supply time constant and the high voltage pulse rate. Each time the program operates to establish the source/drive pulse level and the HV level routine is invoked, another routine is called to determine the number of pulse-echo times to wait between measurements. As a result, the amount of time necessary to change the HV level is variable and dependent on the pulse rate. The circuitry sends a message as soon as the desired level is attained.

For pulse-echo measurement, the relevant subroutines are called each time the timer interrupt is serviced. It loads the times at which the various hardware events are to occur. When an echo is received or the echo detect end time is cleared an interrupt is generated. The interrupt service routine loads and stores the current digital timer value, determines the timer LSB polarity and measures the appropriate ramp analog level. The digital and analog times are stored in work locations of the microprocessor for processing later. This routine is also used to measure the ramp levels during a ramp calibration routine. The decision as to whether a current execution is for pulse-echo timing or for calibration is made on the polarity of a designated bit of a program flow control register.

In the main program loop a subroutine checks if a pulse level optimization request has been received. If so that routine is called.

On receipt of an new HV level or optimization request by the serial interrupt service routine, designated bits of a microcontroller register are set. On entering the pulse level optimization routine, these bits are checked. If set the appropriate routines are called. Before initiating the level optimization routine the HV level equal to the maximum level for the type of bolt being tightened is set. Depending on the type of bolt, this parameter could change over a wide range. There is little point in pulsing a short bolt with the same voltage as a long bolt as the optimization procedure would simply take longer to complete.

On entering this routine the number of pulse-echo times to wait after changing the HV level is determined. On confirming that optimization is actually required, a byte is written into the microcontroller to set the echo detection threshold to 1 volt.

At this point the timer contains the coarse time measurement in units of 100 ns. Dividing the timer value by 16 yields a time measurement with a 1.6 microsecond resolution. By comparing the time-value/16 with the maximum window time, it can be determined if a valid echo was received. If no valid echo is received for pulsing at high voltage maximum settings or no bolt is present, the optimization routine terminates.

On the other hand, if an echo is detected then the pulse width modulation duty cycle is decremented and after a sufficient delay the comparison is made for an echo at the proper window time. This procedure is repeated until the echo is lost. The pulse width modulation duty cycle is then incremented once or twice and this level is then considered the 'optimum' high voltage pulse level for the particular bolt, i.e. the received echo has an amplitude of approximately 3.5 volts.

The first task in threshold optimization is to determine if the circuitry is operating in "pulse-echo" or "echo-echo" mode. In the latter case, threshold optimization must be done on each echo. The program routine for echo detection threshold optimization determines the current timing mode, loads the appropriate parameter values and initiates threshold optimization for one or both echoes.

Two word registers are specifically used by this routine. For each word register the low byte contains a count and the high byte contains a threshold value. The first register contains running values and the second register contains the 'current' biggest values. On entering the routine these registers are zeroed and the actual threshold level is set to a low value, approx.=0.9 volts.

The next stage involves increasing the threshold value until the echo is first encountered. The procedure involves HV pulsing and comparing the current threshold value loaded into the register with the allowed maximum value. If the threshold value held in this register is less than the maximum value it is compared with, then the threshold is increased and the pulse-echo time is measured again. When the echo is first detected the actual TOF is measured and divided by 16 and stored in a register, WINDOW. The threshold COUNT is incremented and the current threshold value is stored. The threshold is incremented and the TOF/16 is measured and compared with the time in WINDOW register. If the absolute difference is = <4 (4 counts=4×16 ×100 ps=6.4 ns) then this is taken as the same time as the measurement at the previous threshold value. Thereafter, the temporary threshold count value is incremented again. This process is repeated until the time difference recorded between threshold changes is greater than 4 counts. The same procedure is then repeated until the time between successive threshold values differs by more than four counts. The threshold level count values are then compared. If the temporary threshold value is the greater, it overwrites the stored max. threshold value for both count and threshold values. This procedure is repeated until the high threshold limit of approximately 4.1 volts is encountered. At this point the threshold register contains a threshold value T for which the TOF at that threshold and the count number of threshold values above are the same. This is the section of the echo upon which it is desired to make TOF readings throughout a tightening. The final task is to determine the midpoint of the band of threshold values and to set the threshold at this point. On exit from this routine the optimum threshold value is stored.

The basic TOF calculation is performed from the time of the high voltage pulse to the receipt of an echo. Echo-echo TOF's are determined by calculating pulse-echo times for both echoes and then subtracting. Calculating the TOF is broken into two operations: a digital and an analog measurement, which yield coarse and fine time information respectively. Put together these two measurement values provide a time measurement with a resolution of 100 ps.

On pulsing the high voltage supply, a 2.5 MHz clock is gated into the T2CLK input of the microcontrollrr and the asynchronous analog ramps are generated. On receipt of an echo both the clock and the ramps are stopped.

A microcontroller second timer (No. 2) counts both positive and negative clock transitions so its resolution at this point is 200 ns. Depending on the polarity of the LSB counted with a separate digital timing circuit 445 driven by the 10 MHz clock an analog measurement is made on either ramp No. 0 or ramp No. 1 and stored in a time register. The second timer (No. 2) value is then multiplied by 2 and the LSB is added to it to give the coarse time in units of 100 ns which is then stored in a word register.

If the current circuit mode is pulse-echo timing, the routine 'TOF' is called every cycle. But, if echo-echo timing is being performed, the second echo TOF must be measured before calling the TOF routine. Within 'TOF' a further routine is called for one or both echoes depending on the timing mode. This second routine performs the actual Time of Flight calculation from the high voltage pulse to a particular echo. If the circuitry is in echo-echo timing mode, this second routine performs the subtraction of the two pulse-echo times to give an echo-echo time.

The temporary time calculated is first multiplied by 1000 to convert it to units of 0.1 ns and is stored in long word register. By examining the polarity of the LSB of the temporary time of flight register a set of calibration values for ramp No. 0 or for ramp No. 1 are selected. The analog time is calculated according to the following formula:

$$T = (AD\_TIME - L)/(H - L) * 1000 \text{ E-10 Seconds}$$

where
H=High ramp calc. point
L=Low ramp calc. point

Since each ramp represents 0.1 us or 100 ns, a multiplying factor of 1000 converts it to units of 0.1 ns or 100 ps.

As tightening control decisions will be made based on the TOF information provided by the circuitry it is important that the circuitry software ensure that only valid data or an informative error message is transmitted over the serial interface. To this end the software both filters and averages the raw TOF data as determined by the TOF calculation routines.

The circuitry has the capability to transmit TOF information based on one or averaged over 2, 4, 8, 16, 32, 64, or 128 pulse-echo time calculations. Prior to permitting a pulse-echo time to be used by the averaging algorithm the data is subject to a software filter. On beginning an averaging cycle the first pulse-echo time is taken as a base value for the number to be averaged which is contained in an average value register. Each of the subsequent pulse-echo times is subject to the filtering algorithm until the number specified by the average value register has been validated, or if greater than four times this value is rejected, the process is aborted and then restarted.

The echo timing is performed on the echo zero-crossings. The time between two positive going or two negative going zero-crossings is approximately 100 ns. During a tightening, the pulse-echo time is expected to increase between successive samples but by nothing like the inter zero-crossing time interval. Thus, if a time difference between the base pulse-echo time and one of the next pulse-echo times is of the order of 100 ns or greater it is assumed an error has occurred and that particular reading is rejected. The acceptance window is defined as +/− 50 ns about the base pulse-echo time. If it is a subsequent pulse-echo time compared with the base time +/− 50 ns is outside this 'time' window, a 'discard' bit is set.

After filtering a pulse-echo time is processed by the main body of the averaging routine.

If the discard bit has been set then a discard counter is incremented. The discard counter is compared with AVG/4. If it is greater than or equal to AVG/4, then the current averaging cycle is abandoned and a new one begun. This procedure guards against the possibility of the base pulse-echo time being a bad measurement itself. If the current pulse-echo sample is not discarded then it is added to a stored running total. Also another routine determines its absolute deviation from the base time and adds that figure to a 'deviation' running total. The number of samples added to the running total is then checked. If this number is less than AVG then the routine is exited awaiting the next pulse-echo sequence. When the average (AVG) number of valid samples have been accumulated then the average deviation and the average TOF are calculated by dividing the accumulated values by AVG. If the average deviation is greater than a limit then the routine is exited otherwise the new average valid TOF is stored. The 'new valid TOF' bit is then set, the 'abort' bit is cleared, the 'new ref.' bit is set and all accumulator registers are cleared ready for the next averaging cycle.

Two anti-phase overlapping ramp signals are generated in sympathy with the 10 MHz clock. These ramps are used to resolve the 100 ns time interval between the clock transitions. By measuring the ramp levels at the clock edges the slope of the ramps can be determined. These points are called ramp calibration points. There are four calibration (calc.) points, one high and one low calc. point for each ramp. They are referred to as H0, L0, H1 and L1. On receipt of an echo the ramps are stopped. The height of the ramp in combination with the calc. points allow the time between clock edges to be resolved by the microcontroller's A/D converter. These calibration points must be measured before performing any TOF calculations. Because standard rather than precision components are used in the ramp generation hardware, the calculation points should be periodically recalculated to protect against ramp slope changes caused by changing ambient conditions or circuit warm-up. A recalibration of the ramps is available on request by serial command.

Dedicated hardware is provided to allow the ramps to be stopped at the calibration points but software must generate the I/O signals to rive the hardware. Because there are two points on each ramp to be measured, calibration is performed in two stages. First L0 and H1 are measured and then H0 and L1. For each stage, a routine loads the appropriate commands to start the ramps, selects the particular pair of calibration points, stops the ramps and generates the interrupt, which will record the analog values.

A routine performs the above measurements sixty four times, accumulates totals, divides by 64 to get average calibration values and stores the results.

Communication to and from the invention is via a serial interface. The microcontroller has a dedicated serial port which can operate at baud rates from 4800 bits per second (b.p.s.) up to 307,200 b.p.s. with a 10 MHz crystal. Data is written out to or read from the serial port by writing and reading a special function register. An interrupt is generated on reception of a byte or on the completion of the transmission of a byte. Using these interrupts, serial handler routines can be written which minimize the processing overhead.

The serial handler routine is on the front end of the serial processing software. It is the routine which receives bytes and places them in a receive buffer and under instruction transmits a multi-byte message from a transmit buffer until it comes across an end of transmission.

On entry the interrupt bit is checked. If set, framing and overrun error bits are checked. If there are no errors, the byte is stored in the next location in the receive buffer and the buffer pointer is incremented. A receive buffer pointer points to the next free location in the buffer memory area. The pointer value is compared with the buffer end address and if equal the buffer pointer is loaded with the address of the start of the that buffer. If a reception error is detected then a 'retransmit' message is sent.

A subroutine in the main program loop checks if any serial processing is required. Except for a two byte transmission on power-up/reset, all communication from the circuitry to outside peripherals is in response to a request from that peripheral. Such requests are in the form of one or two byte messages and are stored in the buffer transmission.

TABLE 1

```
CPUTEST MODULE MAIN, STACKSIZE (50)
$ INCLUDE (D:\ICE196\ASM96\8096.INC)
IOPORT3         EQU             1FFEH:BYTE              ;R/W
IOPORT4         EQU             1FFFH:BYTE              ;R/W
CR              EQU             0DH
LF              EQU             0AH
ETX             EQU             0FFH
PULSETIM        EQU             04H
TIMSTIM         EQU             02H
HITHLIM         EQU             0F0H
LOTHLIM         EQU             30H
STEP            EQU             01H
TIME            EQU             150H
TIME1           EQU             150H
TIME2           EQU             300H

;Register Definitions

RSEG AT 20H
AD_TIME:        DSL             1
AD_TIMER1:      DSL             1
AD_TIMER2:      DSL             1
TIMFLT:         DSL             1
TIMFLTR1:       DSL             1
TIMFLTR2:       DSL             1
ATIMFLT:        DSL             1
BTIMFLT:        DSL             1
CTIMFLT:        DSL             1
PTIMFLT:        DSL             1
XTIMFLT:        DSL             1
DIVREG:         DSL             1
DEV_SUM:        DSW             1
TPTR:           DSW             1
TPTRR1:         DSW             1
TPTRR2:         DSW             1
L0:             DSW             1
L1:             DSW             1
H0:             DSW             1
H1:             DSW             1
H0_L0:          DSW             1
H1_L1:          DSW             1
TEMP:           DSW             1
DLYCNT:         DSW             1
EDST:           DSW             1
EDET:           DSW             1
SERBITS:        DSW             1
SERTEMP:        DSW             1
TEMPTX_PTR:     DSW             1
XMIT_BUF_PTR:   DSW             1
RCV_BUF_PTR:    DSW             1
HVMAX:          DSW             1
ABOR_CTR:       DSW             1
```

```
DEV_SCAT:       DSW             1
WINDOW:         DSW             1
DIFF:           DSW             1
STEMP:          DSW             1
THRES:          DSW             1
HLEVEL:         DSW             1
PUL_RATE:       DSW             1
XPLIER:         DSW             1
EDST1:          DSB             1
EDST2:          DSB             1
PWMCON:         DSB             1
TEMPA:          DSB             1
SCOP:           DSB             1

CSEG AT 200AH
                DCW             SOFTIME_SVC
                DCW             SER_HANDLER

CSEG AT 2018H
CCR:            DCB             0FDH

CSEG AT 2080H
BGIN:           LDB             MODE,#01H
                LDB             AVG,#20H
                LDB             AVGCTR,AVG
RT:             BR              BEGIN

UNCOUPLD:       DCB             'UNCUPLD',CR,ETX
WT_NEW:         DCB             'WT_NEW',CR,ETX
WT_ABR:         DCB             'WT_ABRT',CR,ETX
SCATERR:        DCB             'SCATTER',CR,ETX
END_MSG:        DCB             CR,LF,ETX

CSEG    AT 2220H
```

;MAIN CODE

```
BEGIN:          LD      SP,#STACK
                DI
                CALL    SERINIT
                CALL    PULINIT
                EI
                CALL    CALHSO
                CALL    TIMINIT
                CALL    LOG
                CALL    SETHV
                CALL    DELAY
                CALL    FILTINIT
                ORB     INT_MASK,#40H
                LDB     TEMPB,#08H
                CALL    CONFIRM
HERE:           CALL    CONTROL
                CALL    CKRX
                BR      HERE

SOFTIME_SVC:    PUSHA
                ANDB    INT_MASK,#0DFH
                LDB     HSO_COMMAND,#38H
                ADD     HSO_TIME,TIMER1,PUL_RATE
                CALL    PULSE
                CALL    MODESET
                CMPB    XBITS,#00H
                BNE     NOCALC
                CALL    TOF
                CALL    AVER
NOCALC:         POPA
                RET

MODESET:        CLRC
                BBS     BITS,2,SETXBITS
                CMPB    MODE,#80H
                BE      RINGS
                CMPB    MODE,#81H
                BE      RINGS
                ANDB    XBITS,#0FEH
                BR      EXMODE
RINGS:          BBS     XBITS,0,LDR2
                LD      TPTRR1,TPTR
                LD      AD_TIMER1,AD_TIME
                BR      TOGLE
LDR2:           LD      TPTRR2,TPTR
                LD      AD_TIMER2,AD_TIME
TOGLE:          INCB    XBITS
                ANDB    XBITS,#01H
                BR      EXMODE
SETXBITS:       LDB     XBITS,#01H
EXMODE:         RET
```

```
FILTINIT:       ORB     BITS,#10H
                BBS     BITS,4,$
                CALL    TOF
                LD      PTIMFLT,TIMFLT
                LD      PTIMFLT+2,TIMFLT+2
                ORB     BITS,#02H
                CLRB    DISC_CNT

CLR     ABOR_CTR
                CLR     DEV_SUM
EXFILIN:        RET
DELAY:          LD      DLYCNT,#0500H
LPL:            DEC     DLYCNT
                BNE     LPL
EXDLY:          RET
PULSE_LEV:      CALL    CALCNOP
                BBS     MODE,0,EXPUL_LEV
                LDB     THRESHLD1,#036H
                LDB     IOPORT1,THRESHLD1
                ORB     BITS,#10H
                BBS     BITS,4,$
                CALL    CKRX
                DIVUB   TPTR,#10H
                CMPB    TPTR,EDET
                BE      GHY
                BH      GHY
RETRY:          ORB     BITS,#04H
                DECB    PWMCON
                CMPB    PWMCON,#00H
                BE      GHY
                LDB     PWM_CONTROL,PWMCON
                LDB     TEMPD,PCNT
LPT:            ORB     BITS,#10H
                BBS     BITS,4,$
                DJNZ    TEMPD,LPT
                DIVUB   TPTR,#10H
                CMPB    TPTR,EDET
                BE      STOPT
                BNH     RETRY
STOPT:          INCB    PWMCON
                INCB    PWMCON
                LDB     PWM_CONTROL,PWMCON
                CALL    DELAY
                CALL    THRES_SET
                LDB     TEMPB,#02H
                CALL    CONFIRM
                BR      EXPUL_LEV
GHY:            LDB     TEMPB,#03H
                CALL    CONFIRM
EXPUL_LEV:      RET
```

```
SETHV:      CALL    CALCNOP
            LDB     TEMPA,#03H
            CALL    ATOD
            CMP     TEMP,HLEVEL
            BH      DECREASE
INCREASE:   INCB    PWMCON
            CMPB    PWMCON,#9FH
            BH      EXSETHV
            BE      EXSETHV
            LDB     PWM_CONTROL,PWMCON
            LDB     TEMPD,PCNT
LPTA:       ORB     BITS,#10H
            BBS     BITS,4,$
            DJNZ    TEMPD,LPTA
            ORB     BITS,#10H
            BBS     BITS,4,$
            CALL    CKRX
            ORB     BITS,#10H
            BBS     BITS,4,$
            LDB     TEMPA,#03H
            CALL    ATOD
            CMP     TEMP,HLEVEL
            BNH     INCREASE
            DECB    PWMCON
            BR      EXSETHV
DECREASE:   DECB    PWMCON
            CMPB    PWMCON,#00H
            BNH     EXSETHV
            LDB     PWM_CONTROL,PWMCON
            LDB     TEMPD,PCNT
LPTB:       ORB     BITS,#10H
            BBS     BITS,4,$
            DJNZ    TEMPD,LPTB
            ORB     BITS,#10H
            BBS     BITS,4,$
            CALL    CKRX
            LDB     TEMPA,#03H
            CALL    ATOD
            CMP     TEMP,HLEVEL
            BH      DECREASE
            INCB    PWMCON
            ORB     BITS,#10H
            BBS     BITS,4,$
EXSETHV:    LDB     TEMPA,#03H
            CALL    ATOD
            LD      HLEVEL,TEMP
            RET
CALCNOP:    CMP     PUL_RATE,#012CH
            BNE     CKL1J
            LDB     PCNT,#0DH
            BR      EXCALP
CKL1J:      CMP     PUL_RATE,#0258H
            BNE     CKL2J
            LDB     PCNT,#0AH
            BR      EXCALP
```

```
CKL2J:          CMP     PUL_RATE,#04B0H
                BNE     CKL3J
                LDB     PCNT,#08H
                BR      EXCALP
CKL3J:          CMP     PUL_RATE,#0960H
                BNE     CKL4J
                LDB     PCNT,#05H
                BR      EXCALP
CKL4J:          CMP     PUL_RATE,#12C0H
                BNE     CKL5J
                LDB     PCNT,#03H
                BR      EXCALP
CKL5J:          CMP     PUL_RATE,#2580H
                BNE     CKL6J
                LDB     PCNT,#02H
                BR      EXCALP
CKL6J:          CMP     PUL_RATE,#4B00H
                BNE     CKL7J
                LDB     PCNT,#01H
                BR      EXCALP
CKL7J:          LDB     PCNT,#01H
EXCALP:         RET
CKCON:          LDB     TEMPD,#05H
                CLRB    BCNT
                CALL    DELAY
                CALL    DELAY
OPL:            ORB     BITS,#10H
                BBS     BITS,4,$
                DIVUB   TPTR,#10H
                CMPB    TPTR,EDET
                BE      NEXNOP
                BH      NEXNOP
SLOP:           BR      NOPL
NEXNOP:         INCB    BCNT
NOPL:           DJNZ    TEMPD,OPL
EXCKCON:        RET
AVER:           NOP
                CALL    FILT
                BBC     BITS,5,PROCEED
                INCB    DISC_CNT
                LDB     TEMPB,AVG
                SHRB    TEMPB,#02H
                CMPB    DISC_CNT,TEMPB
                BH       ABOR_RST
                BE      ABOR_RST
                BR      EXAVER
PROCEED:        CALL    SCATTER
                ADD     ATIMFLT+2,TIMFLT+2
                ADD     ATIMFLT,TIMFLT
                BNC     NOADJ
                INC     ATIMFLT+2
NOADJ:          DJNZ    AVGCTR,EXAVER
                CALL    DEV
CKSHF:          CMP     AVGLOG,#00H
```

```
                BE      NOSHIFT
                LDB     TEMPB,AVGLOG
SHIFAGAIN:      SHRL    ATIMFLT,#01H
                DJNZ    TEMPB,SHIFAGAIN
NOSHIFT:        NOP
                CMP     DEV_SCAT,#0FAH
                BH      ABOR_RST
                BE      ABOR_RST
                LD      CTIMFLT,ATIMFLT
                LD      CTIMFLT+2,ATIMFLT+2
                ANDB    TXBITS,#0BFH
                ORB     TXBITS,#80H
                BR      NOABOR
ABOR_RST:       INC     ABOR_CTR
                ORB     TXBITS,#40H
NOABOR:         CLR     ATIMFLT
                CLR     ATIMFLT+2
                LDB     AVGCTR,AVG
                ORB     BITS,#02H
                CLRB    DISC_CNT
                CLR     DEV_SUM
EXAVER:         RET
DEV:            CLR     TEMP
                LDB     TEMP,AVG
                DEC     TEMP
                BE      EXDEV
                CLR     DIVREG+2
                LD      DIVREG,DEV_SUM
                DIVU    DIVREG,TEMP
                LD      DEV_SCAT,DIVREG
EXDEV:          CLR     DEV_SUM
                CLRC
                RET
CONTROL:        NOP
                BBC     RXBITS,6,NRSHV
                CALL    SETHV
                LDB     TEMPB,#0EH
                CALL    CONFIRM
                ANDB    RXBITS,#0BFH
NRSHV:          BBC     RXBITS,7,NREOPT
                LD      HLEVEL,HVMAX
                CALL    SETHV
                CALL    PULSE_LEV
                ANDB    RXBITS,#7FH
NREOPT:         ORB     INT_MASK,#40H
                LDB     PWM_CONTROL,PWMCON
                CMPB    MODE,#80H
                BE      RINGWIN
                CMPB    MODE,#81H
                BE      RINGWIN
                LDB     EDST,EDST1
                ADDB    EDET,EDST1,CEDET
                LDB     IOPORT1,THRESHLD1
                BR      EXCON
```

```
RINGWIN:        BBS     XBITS,0,TIM_R2
                LDB     EDST,EDST1
                ADDB    EDET,EDST1,CEDET
                LDB     IOPORT1,THRESHLD1
                BR      EXCON
TIM_R2:         LDB     EDST,EDST2
                ADDB    EDET,EDST2,CEDET
                LDB     IOPORT1,THRESHLD2
EXCON:          RET
CONFIRM:        LD      TEMPTX_PTR,#BUF_TX
                STB     TEMPB,[TEMPTX_PTR]+
                LDB     TEMPB,#CR
                STB     TEMPB,[TEMPTX_PTR]+
                LDB     TEMPB,#ETX
                STB     TEMPB,[TEMPTX_PTR]+
                LD      XMIT_BUF_PTR,#BUF_TX
                ORB     SCOP,#20H
                CALL    SER_HANDLER
                RET
THRES_SET:      NOP
                BBS     MODE,0,EXTHRESSET
                CMPB    MODE,#80H
                BE      RINGTH
                LD      WINDOW,#TIME
                LDB     EDST,EDST1
                ADDB    EDET,EDST1,CEDET
                CALL    THRES_OPT
                LDB     THRESHLD1,THRESHLD
                BR      EXTHRESSET
RINGTH:         LD      WINDOW,#TIME1
                LDB     EDST,EDST1
                ADDB    EDET,EDST1,CEDET
                CALL    THRES_OPT
                LDB     THRESHLD1,THRESHLD
                LD      WINDOW,#TIME2
                LDB     EDST,EDST2
                ADDB    EDET,EDST2,CEDET
                CALL    THRES_OPT
                LDB     THRESHLD2,THRESHLD
EXTHRESSET:     ANDB    BITS,#0FBH
                RET
THRES_OPT:      LD      THRESTEMP,#00H
                LD      THRESBIG,#00H
                LDB     OFFST,#00H
                LD      THRES,#HITHLIM
DECTHRES:       DECB    THRES
                LDB     IOPORT1,THRES
                ORB     BITS,#10H
                BBS     BITS,4,$
                CMP     TPTR,WINDOW
                BH      DECTHRES
                CALL    TOFC
AX:             NOP
                SHRL    TIMFLT,#04H
                ST      TIMFLT,WINDOW
```

```
               INCB     THRESTEMP
               LDB      THRESTEMP+1,THRES
THRESDEC:      SUBB     THRES,#STEP
NOBLOCK:       CMP      THRES,#LOTHLIM
               BNH      EXTHRLOOP
               LDB      IOPORT1,THRES
               ORB      BITS,#10H
               BBS      BITS,4,$
               ORB      BITS,#10H
               BBS      BITS,4,$
               CALL     TOFC
               SHRL     TIMFLT,#04H
               CMP      TIMFLT,WINDOW
               BH       REVVARS
               SUB      DIFF,WINDOW,TIMFLT
               BR       JOBDON
REVVARS:       SUB      DIFF,TIMFLT,WINDOW
JOBDON:        CMP      DIFF,#04H
               BNH      NONEW
               BE       NONEW
               ST       TIMFLT,WINDOW
               CMPB     THRESTEMP,THRESBIG
               BNH      NONEWTO
               ST       THRESTEMP,THRESBIG
NONEWTO:       LD       THRESTEMP,#00H
NONEW:         INCB     THRESTEMP
               STB      THRES,THRESTEMP+1
               BR       THRESDEC
EXTHRLOOP:     LDB      OFFST,THRESBIG
               LDB      THRESHLD,THRESBIG+1
               SHRB     OFFST,#01H
GETOPT:        ADDB     THRESHLD,#STEP
               DJNZ     OFFST,GETOPT
PULINIT:       LDB      IOC2,#85H
               LDB      IOC1,#71H
               LDB      IOC0,#00H
               CALL     HSOINIT
               LDB      TEMPB,#0FFH
               STB      TEMPB,IOPORT3
               CMPB     MODE,#80H
               BE       RINGPULIN
               CMPB     MODE,#81H
               BE       RINGPULIN
               LDB      PWMCON,#25H
               LDB      PWM_CONTROL,#25H
               LDB      IOPORT1,#060H
               LDB      XBITS,#00H
               LDB      SCATLIM,#0AH
               LDB      THRESHLD1,#60H
               LDB      THRESHLD2,#60H
               LDB      CEDET,#08H
               LD       EDST,#000FH
               LDB      EDST1,#000FH
               LD       EDET,#0028H
               LD       HVMAX,#0320H
```

```
                    LD      HLEVEL,#02A0H
                    LD      PUL_RATE,#04B0H
                    LD      BTIMFLT,#0000H
                    LD      BTIMFLT+2,#0000H
                    LD      XPLIER,#01H
                    BR      EXPULINIT
RINGPULIN:          LDB     PWMCON,#30H
                    LDB     PWM_CONTROL,#30H
                    LDB     SCATLIM,#0AH
                    LDB     THRESHLD1,#80H
                    LDB     THRESHLD2,#80H
                    LDB     IOPORT1,#60H
                    LD      EDST,#000FH
                    LDB     CEDET,#08H
                    LDB     EDST1,#000FH
                    LDB     EDST2,#001DH
                    LD      EDET,#0028H
                    LD      HVMAX,#0320H
                    LD      HLEVEL,#02A0H
                    LD      BTIMFLT,#0000H
                    LD      BTIMFLT+2,#0000H
                    LD      XPLIER,#01H
                    LD      PUL_RATE,#04B0H
EXPULINIT:          CLRB    BITS
                    RET
HSOINIT:            LDB     WSR,#00FH
                    LDB     IOS0,#01H
                    LDB     WSR,#00H
                    RET
TIMINIT:            ORB     INT_MASK,#20H
                    LDB     HSO_COMMAND,#38H
                    ADD     HSO_TIME,TIMER1,PUL_RATE
                    RET
PULSE:              ORB     INT_MASK,#08H
                    ANDB    INT_MASK,#0BFH
                    ANDB    BITS,#56H
                    ORB     BITS,#40H
                    ORB     IOPORT2,#040H
                    ANDB    IOPORT2,#0BFH
                    DI
                    LDB     HSO_COMMAND,#6EH
                    ADD     HSO_TIME,TIMER2,#0000H
                    LD      TEMP,TIMER1
                    ADD     TEMP,#08H
;
                    LDB     HSO_COMMAND,#00H
                    LD      HSO_TIME,TEMP
;
                    LDB     HSO_COMMAND,#21H
                    ADD     HSO_TIME,TEMP,#00H
;
                    LDB     HSO_COMMAND,#22H
                    ADD     HSO_TIME,TEMP,EDST
;
                    LDB     HSO_COMMAND,#02H
                    ADD     HSO_TIME,TEMP,EDET
```

```
          ;
                    LDB     HSO_COMMAND,#11H
                    ADD     HSO_TIME,TEMP,EDET
          ;
                    LDB     HSO_COMMAND,#20H
                    ADD     HSO_TIME,TEMP,EDET
                    EI
                    BBS     BITS,6,$
                    ANDB    INT_MASK,#0F7H
                    ORB     INT_MASK,#40H
                    RET
AD_SVC:             PUSHA
                    BBC     BITS,6,CALRMPS
                    CLRB    TEMPC
                    LDB     TEMPB,#0FFH
                    STB     TEMPB,IOPORT3
                    LDB     TEMPC,IOPORT3
                    ANDB    TEMPC,#01H
                    BBS     TEMPC,0,RMP0
                    LDB     TEMPA,#01H
                    BR      TCAT
RMP0:               LDB     TEMPA,#00H
TCAT:               CALL    ATOD
                    LD      AD_TIME,TEMP
                    LD      TPTR,TIMER2
                    SHL     TPTR,#01H
                    CLRC
                    ADDB    TPTR,TEMPC
PEEK:               SJMP    EXADSVC
CALRMPS:            BBC     BITS,0,OTHERS
                    LDB     TEMPA,#01H
                    CALL    ATOD
                    ADD     H1,TEMP
                    LDB     TEMPA,#00H
                    CALL    ATOD
                    ADD     L0,TEMP
                    SJMP    EXADSVC
OTHERS:             LDB     TEMPA,#00H
                    CALL    ATOD
                    ADD     H0,TEMP
                    LDB     TEMPA,#01H
                    CALL    ATOD
                    ADD     L1,TEMP
EXADSVC:            ANDB    BITS,#06H
                    POPA
                    RET
CALHSO:             NOP
                    ANDB    INT_MASK,#0DFH
                    ORB     INT_MASK,#08H
                    LDB     CCONT,#040H
                    LD      H0,#00H
                    LD      H1,#00H
                    LD      L0,#00H
                    LD      L1,#00H
```

```
LP:         ANDB    IOPORT2,#0BFH
            CALL    HSOINIT
            ANDB    BITS,#06H
            ORB     BITS,#80H
            LDB     TEMPC,#25H
            CALL    CAL
            CALL    HSOINIT
            LDB     TEMPC,#24H
            ANDB    BITS,#06H
            ORB     BITS,#81H
            CALL    CAL
            ORB     IOPORT2,#40H
            DJNZ    CCONT,LP
            SHR     L0,#06H
            SHR     L1,#06H
            SHR     H0,#06H
            SHR     H1,#06H
            SUB     H0_L0,H0,L0
            SUB     H1_L1,H1,L1
            ANDB    INT_MASK,#0F7H
            ORB     INT_MASK,#20H
EXCAL:      RET
CAL:        NOP
            DI
            LD      VTEMP,TIMER1
            ADD     VTEMP,#08H
;
            LDB     HSO_COMMAND,#21H
            LD      HSO_TIME,VTEMP
;
            LDB     HSO_COMMAND,TEMPC
            ADD     HSO_TIME,VTEMP,#00H
;
            LDB     HSO_COMMAND,#33H
            ADD     HSO_TIME,VTEMP,#04H
;
            LDB     HSO_COMMAND,#01H
            ADD     HSO_TIME,VTEMP,#09H
;
            LDB     HSO_COMMAND,#03H
            ADD     HSO_TIME,VTEMP,#09H
            EI
            BBS     BITS,7,$
            RET
ATOD:       ADDB    AD_COMMAND,TEMPA,#0F8H
            NOP
            NOP
            NOP
            NOP
            NOP
            NOP
            BBS     AD_RESULT,3,$
            LD      TEMP,AD_RESULT
            SHR     TEMP,#06H
            RET
```

```
BINBCD:     NOP
            DI
            LD      TEMPTX_PTR,#BUF_TX
            CLR     VTEMP
            LDB     VTEMP,#30H
            STB     VTEMP,[TEMPTX_PTR]+
            DIVU    XTIMFLT,#2710H
            DIVUB   XTIMFLT,#0AH
            ADDB    XTIMFLT,#30H
            STB     XTIMFLT,[TEMPTX_PTR]+
            ADDB    XTIMFLT+1,#30H
            STB     XTIMFLT+1,[TEMPTX_PTR]+
            LD      DIVREG+2,XTIMFLT+2
            LD      VTEMP,#03E8H
            CALL    DIVSTOR
            LD      VTEMP,#0064H
            CALL    DIVSTOR
            LD      VTEMP,#000AH
            CALL    DIVSTOR
            ADDB    DIVREG+2,#30H
            STB     DIVREG+2,[TEMPTX_PTR]+
            CLR     VTEMP
            LDB     VTEMP,#CR
            STB     VTEMP,[TEMPTX_PTR]+
            LDB     VTEMP,#ETX
            STB     VTEMP,[TEMPTX_PTR]
            EI
            RET
DIVSTOR:    LD      DIVREG,DIVREG+2
            CLR     DIVREG+2
            DIVU    DIVREG,VTEMP
            ADDB    DIVREG,#30H
            STB     DIVREG,[TEMPTX_PTR]+
            RET
TOF:        CMPB    MODE,#80H
            BE      TOFRINGS
            CMPB    MODE,#81H
            BE      TOFRINGS
            CALL    TOFC
            BR      EXTOF
TOFRINGS:   LD      TPTR,TPTRR1
            LD      AD_TIME,AD_TIMER1
            CALL    TOFC
            LD      TIMFLTR1,TIMFLT
            LD      TIMFLTR1+2,TIMFLT+2
            LD      TPTR,TPTRR2
            LD      AD_TIME,AD_TIMER2
            CALL    TOFC
            LD      TIMFLTR2,TIMFLT
TT:         LD      TIMFLTR2+2,TIMFLT+2
            SUB     TIMFLT+2,TIMFLTR2+2,TIMFLTR1+2
            SUB     TIMFLT,TIMFLTR2,TIMFLTR1
            BC      EXTOF
            DEC     TIMFLT+2
EXTOF:      RET
```

```
TOFC:       MULU    TIMFLT,TPTR,#03E8H
            LD      VTEMP,TPTR
            SHR     VTEMP,#01H
            BNC     COMP
            ADD     AD_TIME,#32H
            SUB     AD_TIME,L0
            MULU    AD_TIME,#03E8H
            CLRC
            DIVU    AD_TIME,H0_L0
            LD      VTEMP,H0_L0
            BR      EXTOFC
COMP:       CLRC
            ADD     AD_TIME,#32H
            SUB     AD_TIME,L1
            MULU    AD_TIME,#03E8H
            CLRC
            DIVU    AD_TIME,H1_L1
            LD      VTEMP,H1_L1
EXTOFC:     CLRC
            ADD     TIMFLT,AD_TIME
            BNC     NOINC
            INC     TIMFLT+2
            CLRC
NOINC:      LD      DIVREG,#0C350H
            CLR     DIVREG+2
            DIVU    DIVREG,VTEMP
            SUB     TIMFLT,DIVREG
            BC      NODEC
            DEC     TIMFLT+2
NODEC:      RET
FILT:       NOP
            ANDB    BITS,#0DFH
            BBS     BITS,1,NEWPREV
            LD      DIVREG,PTIMFLT
            LD      DIVREG+2,PTIMFLT+2
            ADD     DIVREG,#01F4H
            BNC     NOINCUW
            INC     DIVREG+2
NOINCUW:    CMPL    TIMFLT,DIVREG
            BH      SUBST
            BE      SUBST
            LD      DIVREG,PTIMFLT
            LD      DIVREG+2,PTIMFLT+2
            SUB     DIVREG,#01F4H
            BC      NODECUW
            DEC     DIVREG+2
NODECUW:    CMPL    TIMFLT,DIVREG
            BH      EXFIL
SUBST:      ORB     BITS,#20H
            BR      EXFIL
NEWPREV:    LD      PTIMFLT,TIMFLT
            LD      PTIMFLT+2,TIMFLT+2
            CLRB    DISC_CNT
            CLR     DEV_SUM
            ANDB    BITS,#0DDH
EXFIL:      RET
```

```
SCATTER:    CMP     TIMFLT,PTIMFLT
            BLT     SWAP
            SUB     TEMP,TIMFLT,PTIMFLT
            BR      CALSUM
SWAP:       SUB     TEMP,PTIMFLT,TIMFLT
CALSUM:     ADD     DEV_SUM,TEMP
EXSCAT:     RET
CKRX:       CLR     STEMP
            LDB     OTHER,RXBITS
            ANDB    OTHER,#3FH
            ADDB    STEMP,RD_BUF_PTR,OTHER
            CMP     RCV_BUF_PTR,STEMP
            BE      EXCKRX
            CALL    COL_RCV_BUF
            CMPB    SERBITS,#01BH
            BNH     PROCRX
            ADDB    RD_BUF_PTR,#02H
            BR      BX
PROCRX:     MULUB   SERBITS,#06H
            CMPB    SERBITS,#00H
            BE      BX
            LD      STEMP,#RXROUTS
            ADD     STEMP,SERBITS
            BR      [STEMP]
BX:         CLR     STEMP
            CLR     SERBITS
            CMPB    RD_BUF_PTR,#BUF_RCV+8H
            BNE     EXCKRX
            LDB     RD_BUF_PTR,#BUF_RCV
EXCKRX:     RET
LOG:        LDB     TEMPB,AVG
            CLR     AVGLOG
SHAGAIN:    SHRB    TEMPB,#01H
            BC      EXLOG
            INCB    AVGLOG
            BR      SHAGAIN
EXLOG:      RET
RXROUTS:    LCALL   RCV_ERR
            LJMP    BX
            LCALL   RCV_R101
            LJMP    BX
            LCALL   RCV_POL02
            LJMP    BX
            LCALL   RCV_THR103
            LJMP    BX
            LCALL   RCV_GN04
            LJMP    BX
            LCALL   RCV_AVG05
            LJMP    BX
            LCALL   RCV_R206
            LJMP    BX
            LCALL   RCV_RST07
```

```
            LJMP    BX
            LCALL   RCV_BAUD0B
            LJMP    BX
            LCALL   RCV_?09
            LJMP    BX
            LCALL   RCV_THR20A
            LJMP    BX
            LCALL   RCV_ET0B
            LJMP    BX
            LCALL   RCV_SCAT0C
            LJMP    BX
            LCALL   RCV_RST0D
            LJMP    BX
            LCALL   RCV_HV0E
            LJMP    BX
            LCALL   RCV_PR0F
            LJMP    BX
            LCALL   RCV_RST10
            LJMP    BX
            LCALL   RCV_MUL11
            LJMP    BX
            LCALL   RCV_RST12
            LJMP    BX
            LCALL   RCV_RST13
            LJMP    BX
            LCALL   RCV_RST14
            LJMP    BX
            LCALL   RCV_RST15
            LJMP    BX
            LCALL   RCV_RST16
            LJMP    BX
            LCALL   RCV_Z017
            LJMP    BX
            LCALL   RCV_CAL18
            LJMP    BX
            LCALL   RCV_CAL19
            LJMP    BX
            LCALL   RCV_SCAT1A
            LJMP    BX
            LCALL   RCV_TOF1B
            LJMP    BX
SENMSG:     LD      XMIT_BUF_PTR,#BUF_TX
            CLR     VTEMP
CNT:        LDB     VTEMP,[TEMPTX_PTR]+
            STB     VTEMP,[XMIT_BUF_PTR]+
            CMPB    VTEMP,#ETX
            BNE     CNT
            RET
RCV_ERR:    NOP
            RET
RCV_R101:   LDB     EDST1,1[RD_BUF_PTR]
            DECB    EDST1
            ADDB    RD_BUF_PTR,#02H
            RET
```

```
RCV_POLO2:      LDB     MODE,1[RD_BUF_PTR]
                ADDB    RD_BUF_PTR,#02H
                CLR     BTIMFLT
                CLR     BTIMFLT+2
                ANDB    TXBITS,#0DFH
                ORB     RXBITS,#080H
                RET
RCV_THR103:     LDB     THRESHLD1,1[RD_BUF_PTR]
                ADDB    RD_BUF_PTR,#02H
                RET
RCV_GN04:       CLR     HLEVEL
                LDB     HLEVEL,1[RD_BUF_PTR]
                ADDB    RD_BUF_PTR,#02H
                SHL     HLEVEL,#02H
                CMP     HLEVEL,HVMAX
                BNH     NNELIM
                LD      HLEVEL,HVMAX
NNELIM:         ORB     RXBITS,#040H
                RET
RCV_AVG05:      LDB     AVG,1[RD_BUF_PTR]
                CMPB    AVG,#00H
                BNE     ALTER
                LDB     AVG,#01H
                BR      NOALTER
ALTER:          CALL    LOG
NOALTER:        ADDB    RD_BUF_PTR,#02H
                RET
RCV_R206:       LDB     EDST2,1[RD_BUF_PTR]
                ADDB    RD_BUF_PTR,#02H
                RET
RCV_RST07:      BR      BGIN
                RET
RCV_BAUD08:     LDB     TEMPB,1[RD_BUF_PTR]
                ADDB    RD_BUF_PTR,#02H
                CMPB    TEMPB,#00H
                BE      SET48
                CMPB    TEMPB,#01H
                BE      SET96
                CMPB    TEMPB,#02H
                BE      SET192
                CMPB    TEMPB,#03H
                BE      SET384
                CMPB    TEMPB,#04H
                BE      SET768
                CMPB    TEMPB,#05H
                BE      SET1536
                CMPB    TEMPB,#06H
                BE      SET3072
                BR      EXBAUD
SET48:          LDB     BAUD_RATE,#81H
                LDB     BAUD_RATE,#80H
```

```
               BR      EXBAUD
SET96:         LDB     BAUD_RATE,#40H
               LDB     BAUD_RATE,#80H
               BR      EXBAUD
SET192:        LDB     BAUD_RATE,#20H
               LDB     BAUD_RATE,#80H
               BR      EXBAUD
SET384:        LDB     BAUD_RATE,#0FH
               LDB     BAUD_RATE,#80H
               BR      EXBAUD
SET768:        LDB     BAUD_RATE,#07H
               LDB     BAUD_RATE,#80H
               BR      EXBAUD
SET1536:       LDB     BAUD_RATE,#03H
               LDB     BAUD_RATE,#80H
               BR      EXBAUD
SET3072:       LDB     BAUD_RATE,#01H
               LDB     BAUD_RATE,#80H
EXBAUD:        RET
RCV_?09:       LDB     TEMPB,1[RD_BUF_PTR]
               ADDB    RD_BUF_PTR,#02H
               CMPB    TEMPB,#01H
               BNE     CK03
               LDB     TEMPB,EDST1
               INCB    TEMPB
               BR      EXRCV?
CK03:          CMPB    TEMPB,#03H
               BNE     CK04
               LDB     TEMPB,THRESHLD1
               BR      EXRCV?
CK04:          CMPB    TEMPB,#04H
               BNE     CK05
               LDB     TEMPA,#03H
               CALL    ATOD
               LD      HLEVEL,TEMP
               DIVUB   HLEVEL,#04H
               LDB     TEMPB,HLEVEL
               MULUB   HLEVEL,#04H
               BR      EXRCV?
CK05:          CMPB    TEMPB,#05H
               BNE     CK06
               LDB     TEMPB,AVG
               BR      EXRCV?
CK06:          CMPB    TEMPB,#06H
               BNE     CKOA
               LDB     TEMPB,EDST2
               BR      EXRCV?
CKOA:          CMPB    TEMPB,#0AH
               BNE     CKOB
               LDB     TEMPB,THRESHLD2
               BR      EXRCV?
CKOB:          CMPB    TEMPB,#0BH
               BNE     CKOC
               LDB     TEMPB,CEDET
```

```
              DECB    TEMPB
              BR      EXRCV?
CK0C:         CMPB    TEMPB,#0CH
              BNE     CK0E
              LDB     TEMPB,SCATLIM
              BR      EXRCV?
CK0E:         CMPB    TEMPB,#0EH
              BNE     CK0F
              DIVUB   HVMAX,#04H
              LDB     TEMPB,HVMAX
              MULUB   HVMAX,#04H
              BR      EXRCV?
CK0F:         CMPB    TEMPB,#0FH
              BNE     CK10
              CMP     PUL_RATE,#012CH
              BNE     CKL1
              LDB     TEMPB,#00H
              BR      EXRCV?
CKL1:         CMP     PUL_RATE,#0258H
              BNE     CKL2
              LDB     TEMPB,#01H
              BR      EXRCV?
CKL2:         CMP     PUL_RATE,#04B0H
              BNE     CKL3
              LDB     TEMPB,#02H
              BR      EXRCV?
CKL3:         CMP     PUL_RATE,#0960H
              BNE     CKL4
              LDB     TEMPB,#03H
              BR      EXRCV?
CKL4:         CMP     PUL_RATE,#12C0H
              BNE     CKL5
              LDB     TEMPB,#04H
              BR      EXRCV?
CKL5:         CMP     PUL_RATE,#2580H
              BNE     CKL6
              LDB     TEMPB,#05H
              BR      EXRCV?
CKL6:         CMP     PUL_RATE,#4B00H
              BNE     CKL7
              LDB     TEMPB,#06H
              BR      EXRCV?
CKL7:         CMP     PUL_RATE,#9600H
              BNE     CKL8
              LDB     TEMPB,#07H
              BR      EXRCV?
CKL8:         LDB     TEMPB,#0FFH
              BR      EXRCV?
CK10:         CMPB    TEMPB,#10H
              BNE     CK11
              LDB     TEMPB,THRESBIG
```

```
                BR      EXRCV?
CK11:           CMPB    TEMPB,#11H
                BNE     EXRCV?
                LDB     TEMPB,XPLIER
EXRCV?:         CALL    CONFIRM
                RET
RCV_THR20A:     LDB     THRESHLD2,1[RD_BUF_PTR]
                ADDB    RD_BUF_PTR,#02H
                RET
RCV_ETOB:       LDB     CEDET,1[RD_BUF_PTR]
                INCB    CEDET
                ADDB    RD_BUF_PTR,#02H
                RET
RCV_SCATOC:     LDB     SCATLIM,1[RD_BUF_PTR]
                ADDB    RD_BUF_PTR,#02H
                RET
RCV_RSTOD:      RET
RCV_HVOE:       CLR     HVMAX
                LDB     HVMAX,1[RD_BUF_PTR]
                ADDB    RD_BUF_PTR,#02H
                CMP     HVMAX,#0C0H
                BLT     NOLIMHV
                LD      HVMAX,#0C0H
NOLIMHV:        CMP     HVMAX,#04H
                BH      NOBOT
                LD      HVMAX,#04H
NOBOT:          SHL     HVMAX,#02H
                ORB     RXBITS,#040H
                RET
RCV_PROF:       LDB     TEMPB,1[RD_BUF_PTR]
                ADDB    RD_BUF_PTR,#02H
                CMPB    TEMPB,#00H
                BE      SETP2048
                CMPB    TEMPB,#01H
                BE      SETP1024
                CMPB    TEMPB,#02H
                BE      SETP512
                CMPB    TEMPB,#03H
                BE      SETP256
                CMPB    TEMPB,#04H
                BE      SETP128
                CMPB    TEMPB,#05H
                BE      SETP64
                CMPB    TEMPB,#06H
                BE      SETP32
                CMPB    TEMPB,#07H
                BE      SETP16
                BR      EXPRSET
SETP2048:       LD      PUL_RATE,#012CH
                BR      EXPRSET
SETP1024:       LD      PUL_RATE,#0258H
                BR      EXPRSET
SETP512:        LD      PUL_RATE,#04B0H
```

```
                    BR      EXPRSET
SETP256:            LD      PUL_RATE,#0960H
                    BR      EXPRSET
SETP128:            LD      PUL_RATE,#12C0H
                    BR      EXPRSET
SETP64:             LD      PUL_RATE,#2580H
                    BR      EXPRSET
SETP32:             LD      PUL_RATE,#4B00H
                    BR      EXPRSET
SETP16:             LD      PUL_RATE,#9600H
EXPRSET:            RET
RCV_RST10:          RET
RCV_MUL11:          LDB     XPLIER,1[RD_BUF_PTR]
                    ADDB    RD_BUF_PTR,#02H
                    RET
RCV_RST12:          RET
RCV_RST13:          RET
RCV_RST14:          RET
RCV_RST15:          RET
RCV_RST16:          RET
RCV_RST17:          RET
RCV_Z017:           LD      BTIMFLT,CTIMFLT
                    LD      BTIMFLT+2,CTIMFLT+2
                    XORB    TXBITS,#10H
                    ORB     TXBITS,#20H
                    LDB     TEMPB,#17H
                    CALL    CONFIRM
                    RET
RCV_CAL18:          NOP
                    LD      XMIT_BUF_PTR,#BUF_TX
                    STB     L0,[XMIT_BUF_PTR]+
                    STB     L0+1,[XMIT_BUF_PTR]+
                    STB     L1,[XMIT_BUF_PTR]+
                    STB     L1+1,[XMIT_BUF_PTR]+
                    STB     H0,[XMIT_BUF_PTR]+
                    STB     H0+1,[XMIT_BUF_PTR]+
                    STB     H1,[XMIT_BUF_PTR]+
                    STB     H1+1,[XMIT_BUF_PTR]+
                    LDB     VTEMP,#CR
                    STB     VTEMP,[XMIT_BUF_PTR]+
                    LDB     VTEMP,#ETX
                    STB     VTEMP,[XMIT_BUF_PTR]
                    LD      XMIT_BUF_PTR,#BUF_TX
                    ORB     SCOP,#20H
                    CALL    SER_HANDLER
                    RET
RCV_CAL19:          NOP
                    CALL    CALHSO
                    LDB     TEMPB,#019H
                    CALL    CONFIRM
                    RET
```

```
RCV_SCAT1A:     NOP
                LD      SERTEMP,TPTR
                DIVUB   TPTR,#10H
                CMPB    TPTR,EDET
                BH      SUNCUPL
                BE      SUNCUPL
                CLR     XTIMFLT+2
                LD      XTIMFLT,DEV_SCAT
                CALL    BINBCD
                BR      XSCAT
SUNCUPL:        LD      TEMPTX_PTR,#UNCOUPLD
                CALL    SENMSG
XSCAT:          LD      XMIT_BUF_PTR,#BUF_TX
                ORB     SCOP,#20H
                CALL    SER_HANDLER
                RET
RCV_TOF1B:      NOP
                DI
                CLR     DIVREG+2
                LD      DIVREG,CTIMFLT
                LD      DIVREG+2,CTIMFLT+2
                DIVU    DIVREG,#3E80H
                EI
                CMP     DIVREG,EDET
                BE      UNCUPL
                BH      UNCUPL
                BBS     TXBITS,6,TXWTABR
                BBC     TXBITS,7,TXWTNEW
                CMPB    DEV_SCAT,SCATLIM
                BH      TXSCAT
                LD      XTIMFLT,CTIMFLT
T1:             LD      XTIMFLT+2,CTIMFLT+2
                BBC     TXBITS,4,NOSCAL
                SUB     XTIMFLT,BTIMFLT
                BC      NO_ADJ
                DEC     XTIMFLT+2
NO_ADJ:         SUB     XTIMFLT+2,BTIMFLT+2
                BC      NO_ADJ1
                CLR     XTIMFLT
                CLR     XTIMFLT+2
NO_ADJ1:        BBC     TXBITS,5,NOSCAL
                MULU    XTIMFLT,XPLIER
NOSCAL:         CALL    BINBCD
                ANDB    TXBITS,#7FH
                BR      XMSG
TXWTNEW:        LD      TEMPTX_PTR,#WT_NEW
                ANDB    TXBITS,#7FH
                CALL    SENMSG
                BR      XMSG
TXWTABR:        LD      TEMPTX_PTR,#WT_ABR
                ANDB    TXBITS,#7FH
                CALL    SENMSG
                BR      XMSG
TXSCAT:         LD      TEMPTX_PTR,#SCATERR
```

```
              ANDB      TXBITS,#7FH
              CALL      SENMSG
              BR        XMSG
UNCUPL:       BBC       TXBITS,7,TXWTNEW
              BBS       TXBITS,6,TXWTABR
              LD        TEMPTX_PTR,#UNCOUPLD
              ANDB      TXBITS,#7FH
              CALL      SENMSG
XMSG:         LD        XMIT_BUF_PTR,#BUF_TX
              ORB       SCOP,#20H
              CALL      SER_HANDLER
              RET
SERINIT:      LDB       SP_CON,#0AH
              LDB       SCOP,#00H
              LDB       BAUD_RATE,#0FH
              LDB       BAUD_RATE,#80H
              CLR       SERBITS
              CLRB      RXBITS
              CLRB      TXBITS
              LD        RCV_BUF_PTR,#BUF_RCV
              LD        RD_BUF_PTR,#BUF_RCV
              ORB       INT_MASK,#40H
              RET
SER_HANDLER:  PUSHA
              ORB       SCOP,SP_CON
              BBS       SCOP,6,RCV_HANDLER
              BBS       SCOP,7,RE_TX
              BBS       SCOP,4,RE_TX
              BBC       SCOP,2,CK_TX
RE_TX:        LDB       TEMPB,'R'
              CALL      CONFIRM
              BR        EXSERIAL
CK_TX:        BBC       SCOP,5,EXSERIAL
              LDB       SERTEMP,#ETX
              CMPB      SERTEMP,[XMIT_BUF_PTR]
              BNE       NEXTX
              ANDB      TXBITS,#0FEH
              BR        EXSERIAL
NEXTX:        ORB       SP_CON,#10H
              LDB       SBUF,[XMIT_BUF_PTR]+
EXSERIAL:     CLRB      SCOP
              POPA
              RET
RCV_HANDLER:  STB       SBUF,[RCV_BUF_PTR]+
              CMP       RCV_BUF_PTR,#BUF_RCV+8H
              BNE       NOWRAP
              LD        RCV_BUF_PTR,#BUF_RCV
NOWRAP:       BR        CK_TX
```

```
COL_RCV_BUF:    LDB     OTHER,RXBITS
                ANDB    OTHER,#3FH
                CMPB    OTHER,#00H
                BNE     WT_PKG
                CMPB    SBUF,#'?'
                BNE     CKS
                DEC     RCV_BUF_PTR
                BBS     TXBITS,0,IGNORE
                LDB     SERBITS,#01BH
                ORB     TXBITS,#01H
                BR      IGNORE
CKS:            CMPB    SBUF,#'+'
                BNE     CKCALRQ
                DEC     RCV_BUF_PTR
                BBS     TXBITS,0,IGNORE
                LDB     SERBITS,#01AH
                ORB     TXBITS,#01H
                BR      IGNORE
CKCALRQ:        CMPB    SBUF,#'#'
                BNE     CKRPT
                DEC     RCV_BUF_PTR
                BBS     TXBITS,0,IGNORE
                LDB     SERBITS,#019H
                ORB     TXBITS,#01H
                BR      IGNORE
CKRPT:          CMPB    SBUF,#'!'
                BNE     CKZERO
                DEC     RCV_BUF_PTR
                BBS     TXBITS,0,IGNORE
                LDB     SERBITS,#018H
                ORB     TXBITS,#01H
                BR      IGNORE
CKZERO:         CMPB    SBUF,#'$'
                BNE     WT_PKG
                DEC     RCV_BUF_PTR
                BBS     TXBITS,0,IGNORE
                LDB     SERBITS,#017H
                ORB     TXBITS,#01H
IGNORE:         RET
WT_PKG:         INCB    RXBITS
                LDB     OTHER,RXBITS
                ANDB    OTHER,#3FH
                CMPB    OTHER,#02H
                BE      EXPKT
                LDB     SERBITS,#00H
                RET
```

```
EXPKT:      ANDB    RXBITS,#0C0H
            LDB     SERBITS,[RD_BUF_PTR]
            RET

END
```

Changes can be made in the above-described invent and scope thereof. It is intended, therefore, that the embodiments disclosed above are to be interpreted as illustrative of the invention and not that the invention is to be limited thereto.

What is claimed is:

1. A drive/sense circuit for use with an ultrasonic transducer in contact with a load indicating member, said drive/sense circuit comprising:
    a controller circuit having computation means, data storage means and comparison means;
    a high voltage pulse drive circuit for generating high voltage drive pulses under control of signals from said controller circuit, said high voltage pulse drive circuit having an input connection from said controller circuit and output connection to said ultrasonic transducer;
    a tuned amplifier connected to said ultrasonic transducer for sensing and amplifying ultrasonic drive pulse signals and pulse echo signals, said tuned amplifier being adjusted in frequency to the resonant frequency of said ultrasonic transducer;
    an echo detection circuit connected to said tuned amplifier and to said controller circuit for detecting valid pulse echo signals received by said transducer; and
    a timing circuit connected to said echo detection circuit for measuring the time between a respective ultrasonic drive pulse and a respective pulse echo signal as time of flight and controlling said high voltage pulse drive circuit to predeterminedly vary the amplitude of said high voltage pulses to control the amplitude of said pulse echo signal.

2. The drive/sense circuit of claim 1 wherein said high voltage pulse drive circuit is optimally set according to said ultrasonic transducer individual performance characteristics to produce said pulse echo signal at a predetermined amplitude.

3. The drive/sense circuit of claim 1 wherein said controller circuit control signals to said high voltage supply circuit are pulse width modulation signals.

4. The drive/sense circuit of claim 1 wherein said load indicating member is a fastener.

5. A drive/sense circuit for use with an ultrasonic transducer in contact with a load indicating member, said drive/sense circuit comprising:
    a controller circuit having computation means, data storage means and comparison means;
    a high voltage pulse drive circuit for generating high voltage drive pulses under control of signals from said controller circuit, said high voltage pulse drive circuit having an input connection from said controller circuit and output connection to said ultrasonic transducer;
    a tuned amplifier connected to said ultrasonic transducer for sensing and amplifying ultrasonic drive pulse signals and pulse echo signals, said tuned amplifier being adjusted in frequency to the resonant frequency of said ultrasonic transducer;
    an echo detection circuit connected to said tuned amplifier and to said controller circuit for detecting valid pulse echo signals received by said transducer; and
    a timing circuit connected to said echo detection circuit for measuring the time between a respective ultrasonic drive pulse and a respective pulse echo signal as time of flight wherein said timing circuit performs digital counting and analog interpolation between digital counts, said analog interpolation being implemented by using two out of phase ramp signals such that at all times one of said ramp signals is used to provide a measure of the fraction of a said digital count period;
    wherein said timing circuitry generates artificial stop signals, said artificial stop signals used for calibration of said ramp signals.

6. The drive/sense circuit of claim 5 wherein said artificial stop signals are generated at precise intervals in time and wherein said ramp signals calibration is conducted on request.

7. The drive/sense circuit of claim 6 wherein said load indicating member is a fastener.

8. A drive/sense circuit for use with an ultrasonic transducer in contact with a load indicating member, said drive/sense circuit comprising:
    a controller circuit having computation means, data storage means and comparison means;
    a high voltage pulse drive circuit for generating high voltage drive pulses under control of signals from said controller circuit, said high voltage pulse drive circuit having an input connection from said controller circuit and output connection to said ultrasonic transducer;
    a tuned amplifier connected to said ultrasonic transducer for sensing and amplifying ultrasonic drive pulse signals and pulse echo signals, said tuned amplifier being adjusted in frequency to the resonant frequency of said ultrasonic transducer;

an echo detection circuit connected to said tuned amplifier and to said controller circuit for detecting valid pulse echo signals received from said transducer; and a timing circuit connected to said echo detection circuit for measuring the time between a respective ultrasonic drive pulse and a respective pulse echo signal as time of flight wherein said controller circuit establishes a timing period, said timing period having an end determined by a pulse echo signal zero crossing after said pulse echo signal exceeds a preset threshold value;

wherein said pulse echo signal zero crossing is the first zero crossing after said pulse echo signal exceeds said preset threshold value;

wherein said echo detection circuitry automatically detects and selects between the first positive going zero crossing after exceeding a negative threshold and the first negative going zero crossing after exceeding a positive threshold.

9. The drive/sense circuit of claim 8 wherein said load indicating member is a fastener.

10. A drive/sense circuit for use with an ultrasonic transducer in contact with a load indicating member, said drive/sense circuit comprising:

a controller circuit having computation means, data storage means and comparison means;

a high voltage pulse drive circuit for generating high voltage drive pulses under control of signals from said controller circuit, said high voltage pulse drive circuit having an input connection from said controller circuit and output connection to said ultrasonic transducer;

a tuned amplifier connected to said ultrasonic transducer for sensing and amplifying ultrasonic drive pulse signals and echo signals, said tuned amplifier being adjusted in frequency to the resonant frequency of said ultrasonic transducer;

an echo detection circuit connected to said tuned amplifier and to said controller circuit for detecting valid pulse echo signals received by said transducer; and a timing circuit connected to said echo detection circuit for measuring the time between a respective ultrasonic drive pulse and a respective pulse echo signal as time of flight, and wherein said echo detection circuit automatically establishes a threshold value against which said pulse echo signals are measured wherein said threshold values are selected to minimize errors, including means for identifying the amplitude of the largest face of exposure of each of said pulse echo signals and means connected thereto for establishing the signal level of the principal lobe (phase) of each of said pulse echo signals.

11. The drive/sense circuit of claim 10 wherein said threshold value used in said echo detection circuitry is automatically selected for said transducer in contact with said load indicating member using a threshold optimization technique to minimize errors due to signal level variations, said threshold optimization technique comprising the measuring of the time of flight with at least two threshold values.

12. The drive/sense circuit of claim 10 wherein said load indicating member is a fastener and said controller circuit computes the time of flight of said pulse echo signal with respect to the respective ultrasonic drive pulse, changes in time of flight values are calculated between successive values of said time of flight and said change is compared to stored data to determine the instantaneous tension in said fastener.

13. A drive/sense circuit for use with an ultrasonic transducer in contact with a load indicating member, said drive/sense circuit comprising:

a controller circuit having computation means, data storage means and comparison means;

a high voltage pulse drive circuit for generating high voltage drive pulses under control of signals from said controller circuit, said high voltage pulse drive circuit having an input connection from said controller circuit and output connection to said ultrasonic transducer;

a tuned amplifier connected to said ultrasonic transducer for sensing and amplifying ultrasonic drive pulse signals and echo signals, said tuned amplifier being adjusted in frequency to the resonant frequency of said ultrasonic transducer;

an echo detection circuit connected to said tuned amplifier and to said controller circuit for detecting valid pulse echo signals received by said transducer; and a timing circuit connected to said echo detection circuit for measuring the time between a respective ultrasonic drive pulse and a respective pulse echo signal as time of flight wherein said controller circuit operates to discard an invalid time of flight by a first data filtering technique comprising taking multiple time of flight measurements and discarding those outside of a time acceptance window, said time acceptance window being determined from previous time of flight measurements;

wherein said first data filtering technique is aborted if more than a preset percentage of said time of flight measurements are discarded;

wherein a scatter value is calculated for said plurality of time of flight measurements;

wherein said average of the plurality of the time of flight measurements is discarded if said scatter value exceeds a preset value.

14. The drive/sense circuit of claim 13 wherein the width of said time acceptance window is less than two periods of the waveform of an echo signal output from said tuned amplifier.

15. The drive/sense circuit of claim 14 wherein said controller circuit computes an average of a plurality of said time of flight measurements.

16. The drive/sense circuit of claim 15 wherein said controller circuit time of flight computation is based on averaging at least four time of flight measurements.

17. The drive/sense circuit of claim 13 wherein said load indicating member is a fastener.

18. A drive/sense circuit for use with an ultrasonic transducer in contact with a load indicating member, said drive/sense circuit comprising:

a controller circuit having computation means, data storage means and comparison means;

a high voltage pulse drive circuit for generating high voltage drive pulses under control of signals from said controller circuit, said high voltage pulse drive circuit having an input connection from said controller circuit and output connection to said ultrasonic transducer;

a tuned amplifier connected to said ultrasonic transducer for sensing and amplifying ultrasonic drive pulse signals and echo signals, said tuned amplifier being adjusted in frequency to the resonant frequency of said ultrasonic transducer;

an echo detection circuit connected to said tuned amplifier and to said controller circuit for detecting valid pulse echo signals received by said transducer; and a timing circuit connected to said echo detection circuit for measuring the time between a respective ultrasonic drive pulse and a respective pulse echo signal as time of flight wherein said controller selects an echo from a drive pulse for measurement and wherein successive drive pulses are generated to interleave their respective echoes between echoes of preceding drive pulses.

19. The drive/sense circuit of claim 18 wherein said load indicating member is a fastener.

20. A drive/sense circuit for use with an ultrasonic transducer in contact with a load indicating member, said drive/sense circuit comprising:

a controller circuit having computation means, data storage means and comparison means;

a high voltage pulse drive circuit for generating high voltage drive pulses under control of signals from said controller circuit, said high voltage pulse drive circuit having an input connection from said controller circuit and output connection to said ultrasonic transducer;

a tuned amplifier connected to said ultrasonic transducer for sensing and amplifying ultrasonic drive pulse signals and pulse echo signals, said tuned amplifier being adjusted in frequency to the resonant frequency of said ultrasonic transducer;

an echo detection circuit connected to said tuned amplifier and to said controller circuit for detecting valid pulse echo signals received by said transducer; and a timing circuit connected to said echo detection circuit for measuring the time between a respective ultrasonic drive pulse and a respective pulse echo signal as time of flight wherein said drive/sense circuit further comprises a means of timing from a first pulse echo signal to a second pulse echo signal, said means comprising means for: (a) timing from a first high voltage pulse to a first pulse echo signal using a first set of pulse drive and echo detection windows to provide a first time measurement, (b) timing from a second high voltage pulse to a second echo using a second set of pulse drive and echo detection windows to provide a second time measurement, and (c) subtracting said first time measurement from said second time measurement.

21. The drive/sense circuit of claim 20 wherein said load indicating member is a fastener.

22. An electronic drive/sense circuit for use in determining the time of flight of ultrasonic waves in a fastener, said fastener having an ultrasonic transducer in contact therewith for passing said ultrasonic waves along said fastener length and sensing reflected waves (pulse echo signals), comprising:

a software driven, microprocessor-based controller;

a memory connected to said microprocessor of said controller;

a pulse generating circuit for generating transducer drive pulses being connected to said transducer and supplying pulses thereto, said pulse generating circuit being controlled with pulse trigger signals received by a connection from said controller;

a comparator circuit connected via a tuned amplifier circuit to said pulse generating circuit output and to said transducer for receiving said drive pulses and said pulse echo signals, said comparator circuit having an echo detection enable signal connection from said controller and an echo trigger level signal connection from said controller;

a digital timer gating circuit connected to an output of said comparator circuit and a pulse trigger sync signal connection from said controller;

a time counter circuit connected to the output of said timer gating circuit and having its output connected to said controller; and an analog time resolver circuit connected to said digital timer gating circuit and having an output connected to said controller;

wherein said time counter circuit is resident within said controller and connected to said microprocessor therewithin;

wherein said pulse generating circuit includes a high voltage generator and a pulse drive circuit connected to said high voltage generator and wherein said high voltage generator output voltage level is adjustable from said controller to control the amplitude of the ultrasonic drive pulse and said pulse echo signal.

23. The electronic drive/sense circuit of claim 22 wherein said pulse trigger signals from said controller are pulse width modulation signals connected to said high voltage generator.

24. The electronic drive/sense circuit of claim 23 wherein said comparator circuit includes a tuned pulse amplifier connected to said pulse drive circuit output and to said transducer and an echo detection circuit connected to the output of said tuned pulse amplifier.

25. The electronic drive/sense circuit of claim 24 wherein said echo detection circuit has echo detection time window settings and echo threshold settings.

26. The electronic drive/sense circuit of claim 25 wherein said echo detection circuit time window settings and echo threshold settings are software established from said controller.

27. The electronic drive/sense circuit of claim 26 wherein said analog time resolver circuit output to said controller includes a first ramp signal connection and a second ramp signal connection.

28. The electronic drive/sense circuit of claim 27 wherein said first and second ramp signals are identical in shape and amplitude and approximately 180 degrees out of phase with one another.

29. A drive/sense circuit for use with an ultrasonic transducer in contact with a load indicating member, said drive/sense circuit comprising:

a controller circuit having computation means, data storage means and comparison means;

a high voltage pulse drive circuit for generating high voltage drive pulses under control of signals from said controller circuit, said high voltage pulse drive circuit having an input connection from said controller circuit and output connection to said ultrasonic transducer;

a tuned amplifier connected to said ultrasonic transducer for sensing and amplifying ultrasonic drive pulse signals and echo pulse signals, said tuned amplifier being adjusted in frequency to the resonant frequency of said ultrasonic transducer;

an echo detection circuit connected to said tuned amplifier and to said controller circuit for detecting valid pulse echo signals received by said transducer; and a timing circuit connected to said echo detection circuit for measuring the time between a respective ultrasonic drive pulse and a respective pulse echo signal as time of flight wherein said high voltage pulse drive circuit produces said high voltage pulse being predeterminedly variable to an amplitude;

wherein said high voltage pulse is predeterminedly variable under the operation of said controller circuit and wherein said controller circuit computation means includes:

a) means for setting an echo detection window in said echo detection circuit for an echo;
b) means for setting said high voltage drive circuit to peak level output;
c) means for setting a detection threshold and an average level in said echo detection circuit to approximately 1 volt;
d) means for waiting for a second pulse/echo cycle;
e) means for determining the presence of an echo and a time out;
f) means for generating a bad bolt signal upon a time out determination;
g) means for reducing said high voltage drive circuit signal level upon an echo determination;
h) means for waiting for a successive pulse/echo cycle;
i) means for again reducing said high voltage drive circuit signal level upon the determination of another echo;
j) means for increasing said high voltage drive circuit signal level upon the determination of another time out; and
k) means for storing the values of high voltage drive circuit signal levels.

30. A drive/sense circuit for use with an ultrasonic transducer in contact with a load indicating member, said drive/sense circuit comprising:

a controller circuit having computation means, data storage means and comparison means;

a high voltage pulse drive circuit for generating high voltage drive pulses under control of signals from said controller circuit, said high voltage pulse drive circuit having an input connection from said controller circuit and output connection to said ultrasonic transducer;

a tuned amplifier connected to said ultrasonic transducer for sensing and amplifying ultrasonic drive pulse signals and pulse echo signals, said tuned amplifier being adjusted in frequency to the resonant frequency of said ultrasonic transducer;

an echo detection circuit connected to said tuned amplifier and to said controller circuit for detecting valid pulse echo signals received by said transducer; and a timing circuit connected to said echo detection circuit for measuring the time between a respective ultrasonic drive pulse and a respective pulse echo signal as time of flight wherein said timing circuit performs digital counting and analog interpolation between digital counts, said analog interpolation being implemented by using two out of phase ramp signals such that at all times one of said ramp signals can be used to provide a measure of the fraction of a said digital count period;

wherein said digital counting and analog interpolation is computed by said controller circuit and wherein said controller circuit computation means operates upon A, H, L, H0, L0, H1, L1, LBS signals, and wherein said controller circuit computation mean includes:

a) means for measuring a ramp level equal to A;
b) means for determining said timing circuit LBS polarity;
c) means for setting H=H0,, L=L0 and H−L=H0−L0 upon said LBS polarity being "0";
d) means for setting H=H1, L=L1 and H−L=H1−L1 upon said LBS polarity being "1";
e) means for calculating analog time, "T" as a function of the 100 ns digital count resolution, T=(A−L)/(H−L);
f) means for scaling "T" so that one (1) count=0.1 ns, T (0.1 ns)=(A−L)/(H−L)×(1000); and
g) mean for storing this analog time for use by the circuit.

31. A drive/sense circuit for use with an ultrasonic transducer in contact with a load indicating member, said drive/sense circuit comprising:

a controller circuit having computation means, data storage means and comparison means;

a high voltage pulse drive circuit for generating high voltage drive pulses under control of signals from said controller circuit, said high voltage pulse drive circuit having an input connection from said controller circuit and output connection to said ultrasonic transducer;

a tuned amplifier connected to said ultrasonic transducer for sensing and amplifying ultrasonic drive pulse signals and echo signals, said tuned amplifier being adjusted in frequency to the resonant frequency of said ultrasonic transducer;

an echo detection circuit connected to said tuned amplifier and to said controller circuit for detecting valid pulse echo signals received from said transducer; and a timing circuit connected to said echo detection circuit for measuring the time between a respective ultrasonic drive pulse and a respective pulse echo signal as time of flight, and wherein said echo detection circuit automatically establishes a threshold value against which said pulse echo signals are measured wherein said threshold values are selected to minimize errors;

wherein said controller circuit computes said threshold value and wherein said controller circuit computation means includes:

a) means for setting an echo detection window for a required echo;
b) means for setting a low threshold value, at approximately 1 volt, and for establishing a zero counter and a maximum value counter;
c) means for waiting for a next pulse/echo cycle;
d) means for measuring an echo time of flight (TOF);
e) means for storing TOF in a TOF counter and for storing current threshold value in a current threshold value counter and incrementing said zero and maximum value counters;
f) means for incrementing the threshold value;
g) means for establishing a high limit, and for determining when the threshold value exceeds the high limit, and then for calculating optimum threshold equal to maximum value minus the threshold plus the maximum value minus the counter value, this all being divided by two;

h) means for determining when the threshold value is less than the high limit, and for waiting for the next pulse echo cycle and for measuring TOF;

i) means for determining when the new TOF has not changed, and for incrementing the zero and maximum value counters and for incrementing the threshold value counter;

j) means for determining the TOF has changed, and for storing the TOF counter value and threshold counter value;

k) means for determining the TOF counter value is less than the maximum value stored in the maximum counter, and for zeroing the TOF counter and for waiting for the next pulse echo cycle; and l) means for determining the TOF counter value is greater than the maximum counter value, for storing the TOF counter value in the maximum counter and for storing the current threshold counter value in the maximum threshold counter, and for zeroing the TOF counter and for waiting for the next pulse/echo cycle.

32. A drive/sense circuit for use with an ultrasonic transducer in contact with a load indicating member, said drive/sense circuit comprising:

a controller circuit having computation means, data storage means and comparison means;

a high voltage pulse drive circuit for generating high voltage drive pulses under control of signals from said controller circuit, said high voltage pulse drive circuit having an input connection from said controller circuit and output connection to said ultrasonic transducer;

a tuned amplifier connected to said ultrasonic transducer for sensing and amplifying ultrasonic drive pulse signals and pulse echo signals, said drive pulse signals having an interval time there between, said pulse echo signals having an interval time there between said tuned amplifier being adjusted in frequency to the resonant frequency of said ultrasonic transducer;

an echo detection circuit connected to said tuned amplifier and to said controller circuit for detecting valid pulse echo signals received from said transducer; and a timing circuit connected to said echo detection circuit for measuring the time between a respective ultrasonic drive pulse and a respective pulse echo signal as time of flight (TOF) wherein said controller circuit operates to discard an invalid time of flight by a first data filtering technique comprising taking multiple time of flight measurements and discarding those outside of a time acceptance window, said time acceptance window being determined from previous time of flight measurements;

wherein said controller circuit controls said timing circuit to perform said filtering technique and wherein said controller circuit computation means includes:

a) means for determining if a TOF value is the first sample of a set and if it is for establishing the TOF value as the first sample and for waiting for more TOF value samples;

b) means for determining if the current TOF value is within 50 ns of the pulse interval time and if it is not then establishing and incrementing a discard counter;

c) means for determining if the discard number held in the discard counter is not equal to or greater than 4 and for waiting for another TOF value;

d) means for determining when the discard number held in the discard counter is equal to or is greater than 4, and then for establishing an "abort" counter and for incrementing the "abort" counter, for clearing the present discard counter and for setting a flag for a new cycle;

e) means for determining when the current TOF value is within 50 ns of the pulse interval time, and then measuring the absolute difference between pulse interval times and then for adding this absolute difference value to a running total of differences thereof established;

f) means for adding the current TOF value to the running total of differences and for then determining the current number of TOF value samples and for determining when the current number of samples is equal to the number of samples needed to average;

g) means for waiting for the next cycle when the current number of TOF value samples is less than the number needed to average;

h) means for calculating the average absolute deviation of the TOF value samples when the current number of TOF value samples is the number needed to average;

i) means for dividing the running total of differences by the number of TOF value samples and for setting the quotient equal to an average value;

j) means for determining when the average value for deviation exceeds a preset limit, and then for incrementing the abort counter, for clearing the discard counter and for setting a flag for a new cycle; and k) means for determining when the average value for deviation is less than a preset limit, and then for storing the new TOF value, for setting a flag indicating a valid TOF and for setting a new cycle.

* * * * *